(12) United States Patent
Shen et al.

(10) Patent No.: US 11,325,929 B2
(45) Date of Patent: May 10, 2022

(54) PHOSPHORUS-CONTAINING COMPOUND AND PREPARATION AND USE THEREOF

(71) Applicant: VivaVisionShanghaiLtd, Shanghai (CN)

(72) Inventors: Wang Shen, Shanghai (CN); Yue Ding, Shanghai (CN); Hao Jiang, Shanghai (CN); Fu li Chen, Shanghai (CN); Jiangfeng Wang, Shanghai (CN); Xinglong Wu, Shanghai (CN); Cunfei Li, Shanghai (CN); Liguo Yang, Shanghai (CN); Biao Hu, Shanghai (CN); Qiyang Jiang, Shanghai (CN); Zhixing An, Shanghai (CN); Kuifeng Dang, Shanghai (CN)

(73) Assignee: VivaVisionShanghaiLtd, Shanghai (CN)

( * ) Notice: Subject to any disclaimer, the term of this patent is extended or adjusted under 35 U.S.C. 154(b) by 0 days.

(21) Appl. No.: 16/606,774

(22) PCT Filed: May 21, 2018

(86) PCT No.: PCT/CN2018/087629
§ 371 (c)(1),
(2) Date: Oct. 21, 2019

(87) PCT Pub. No.: WO2019/001171
PCT Pub. Date: Jan. 3, 2019

(65) Prior Publication Data
US 2020/0131206 A1   Apr. 30, 2020

(30) Foreign Application Priority Data
Jun. 27, 2017 (CN) .......................... 201710502653.3
Apr. 3, 2018 (CN) .......................... 201810291023.0

(51) Int. Cl.
*C07F 9/32* (2006.01)
*A61K 9/00* (2006.01)
*A61K 9/08* (2006.01)
*C07F 9/53* (2006.01)

(52) U.S. Cl.
CPC .......... *C07F 9/3241* (2013.01); *A61K 9/0048* (2013.01); *A61K 9/08* (2013.01); *C07F 9/3229* (2013.01); *C07F 9/5329* (2013.01)

(58) Field of Classification Search
None
See application file for complete search history.

(56) References Cited

U.S. PATENT DOCUMENTS

2014/0256684 A1   9/2014   Beard et al.
2016/0083342 A1   3/2016   Yuan et al.

FOREIGN PATENT DOCUMENTS

| CN | 1700923 | 11/2005 |
|---|---|---|
| EP | 2987491 A1 | 2/2016 |
| JP | 2005-526741 A | 9/2005 |
| JP | 2008-545656 A | 12/2008 |

OTHER PUBLICATIONS

"International Search Report (Form PCT/ISA/210) of PCT/CN2018/087629," dated Jul. 4, 2018, with English translation thereof, pp. 1-6.
Zahra Rezaei et al.,"Design and one-pot synthesis of new α-aminophosphonates and antimicrobial activity", Journal of Pharmaceutical Negative Results, vol. 2, Dec. 2011, pp. 1-10.
Donnenfeld et al., Lifitegrast for the treatment of dry eye disease in adults, Expert Opinion on Pharmacotherapy, Sep. 2017, vol. 18, No. 14, p. 1517-1524.
New drug for the treatment of dry eye disease—Lifitegrast, Herald of Medicine, Feb. 2017, vol. 36, No. 2, and its English abstract, 7 pages.

*Primary Examiner* — Joseph R Kosack
(74) *Attorney, Agent, or Firm* — Bret E. Field; Bozicevic, Field & Francis LLP

(57) ABSTRACT

The present invention provides a phosphorus-containing compound characterized by being a compound represented by the following structure:

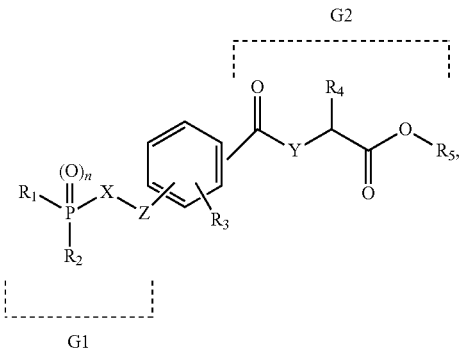

the compound is a novel immune cell migration inhibitor. The compound has good hydrophilicity and can be developed into eye drops. The compound has a strong inhibitory ability to immune cell migration and can relieve the symptoms of most dry-eye patients.

13 Claims, No Drawings

PHOSPHORUS-CONTAINING COMPOUND AND PREPARATION AND USE THEREOF

CROSS-REFERENCE TO RELATED APPLICATION

This application is a 371 application of International PCT application serial no. PCT/CN2018/087629, filed on May 21, 2018, which claims the priority benefit of Chinese application no. 201710502653.3, filed on Jun. 27, 2017, and Chinese application no. 201810291023.0, filed on Apr. 3, 2018. The entirety of each of the abovementioned patent applications is hereby incorporated by reference herein and made a part of this specification.

BACKGROUND

Technical Field

The present invention relates to the field of pharmaceuticals, and in particular to phosphorus-containing compound, preparation method thereof, and use for treating dry eye.

Description of Related Art

Tears provide long-lasting moisturization and lubrication to the eyes, which is the key to maintaining vision and eye comfort. Tears are composed of water, lipids, mucus, antibodies, and specific proteins with anti-infective properties. These components are secreted by specific glands located around the eyes. When there is an imbalance in the tear system, people will feel dry eyes.

Dry eye syndrome is a common ocular surface inflammatory disease. People with dry eye may experience eye pain, photosensitivity, itching, redness and blurred vision. Dry eye syndrome is caused by multiple inducing factors, including age, gender, environment, medicine, surgery, and systemic diseases such as autoimmune diseases, diabetes, thyroid disease, and lymphoma. If dry eye disease is not diagnosed and treated properly, it may lead to further complications such as infection, keratinization of the ocular surface, corneal ulceration and conjunctiva squamatization.

Therefore, dry eye syndrome is a very serious disease that affects 5-10% of the population, especially those who work long hours in front of computer and those after the middle age. More than 30% patients in today's ophthalmologist clinics are dry eye patients. Despite the large number of patients with dry eye syndrome in China, there is no drug approved for the treatment of dry eye syndrome. The patient can only have temporary relief from artificial tears. Therefore, there is an urgent need for drugs for treating dry eye syndrome.

The incidence of dry eye syndrome is directly proportional to the age, about 20% of people over 50 years old have different degrees of dry eye syndrome; gender also affects dry eye syndrome, and women, especially older women, have a much higher percentage of dry eye syndrome than men, which may be related to the secretion of sex hormones; white-collar workers stay for a long time in the air-conditioned environment, and the long-term use of the screen also causes a high incidence of dry eye syndrome in this population. Dry eye syndrome is a continuous pathological process in which the condition progresses from light to severe, and there is no obvious boundary between light, medium and severe. Despite the complex etiology of dry eye syndrome, studies find that the pathology of dry eye caused by various causes is similar: immune cells invade the surface tissue of the eyes and trigger chronic inflammation, causing ocular surface damage. Currently, two drugs are approved in the European and American markets: (1) cyclosporin A (as a suspension, or as a nanoparticle solution). This medicine is a very powerful immune system inhibitor, so it may cause damage to the immune system. At the same time, because it is a suspension, there are problems concerning long-term storage stability, and the eye irritation in the patients using the drug; (2) Lifitegrast, the drug was approved by the US FDA in December 2016, which is an immune cell migration inhibitor, and achieves the therapeutic effect by blocking the immune cells from entering into the site of inflammation; however, the drug is highly lipophilic and has no clinical effect on >50% of patients.

SUMMARY

The invention is related to a new immune cell migration inhibitor. It has good hydrophilicity and can be developed into eye drops. It has a strong inhibitory effect on immune cell migration and can alleviate the symptoms of most dry eye patients.

The invention provides a series of phosphorus-containing compounds, the particular features are represented by the following structure:

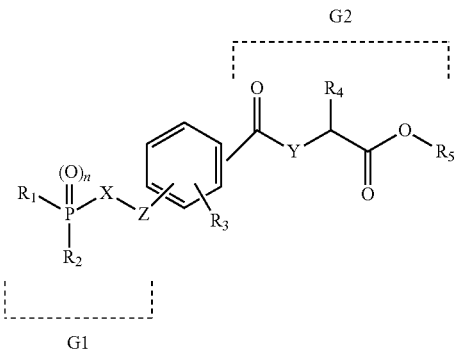

$R_1$ is selected from the group consisting of alkyl, aryl, benzyl and derivatives thereof;

the alkyl group in $R_1$ is selected from straight chain, branched chain or cyclo-$C_{1-12}$alkyl, such as, methyl, ethyl, propyl, isopropyl, butyl, isobutyl, pentyl, cyclopentyl, hexyl, cyclohexyl, and the like;

the aryl group is selected from phenyl, naphthyl, quinolyl, or phenyl with one or more carbons on the benzene ring substituted by $C_{1-3}$ alkyl/phenyl/halogen/nitro/amino/sulfonyl/hydroxy/$C_{1-3}$ alkoxy;

the benzyl group is selected from, benzyl with one or more carbons on the benzene ring substituted by $C_{1-3}$ alkyl/phenyl/halogen/nitro/amino/sulfonyl/amino/$C_{1-3}$ alkylbenzyl;

$R_2$ is selected from hydroxy, alkyl, hydrogen, alkoxy, amine, and alkylamine;

the alkyl group in $R_2$ is selected from straight chain, branched chain or cyclo-$C_{1-12}$alkyl, such as, methyl, ethyl, propyl, isopropyl, butyl, isobutyl, pentyl, cyclopentyl, hexyl, cyclohexyl, and the like;

the alkoxy group is selected from straight chain, branched chain or cycloalkyloxy having 1 to 12 carbon atoms, such as, methoxy, ethoxy and the like;

n is selected from 0 or 1;

X is selected from carbon, oxygen, and nitrogen;

In some embodiments, when X is carbon, it may be (—CH$_2$—), or (—C(R1R2)-, wherein, R1, R2 may be the same or different arbitrary substituents, such as hydrogen, alkyl such as methyl, ethyl and the like, aromatic group such as phenyl, benzyl and the like; hydroxy, alkoxy, halogen, and the like);

In some embodiments, when X is nitrogen, it may be (—NH—), or (—N(R$_N$)—, wherein R$_N$ may be any substituent group, for example, alkyl such as methyl, ethyl and the like, aromatic group such as phenyl, benzyl and the like;

Z is selected from carbon, oxygen, sulfur, and nitrogen;

In some embodiments, when Z is carbon, it may be a carbonyl group (—(C=O)—), an alkylene group (—C$_n$H$_{2n}$—, wherein, n is a natural number of 10 or less), or (—C(R1R2)-, branched alkylene, wherein, R1 and R2 may be the same or different arbitrary substituent group, for example, hydrogen, alkyl group such as methyl, ethyl and the like, aromatic group such as phenyl, benzyl and the like, hydroxy, alkoxy, halogen, and the like);

In some embodiments, when Z is nitrogen, it may be (—NH—), or (—N(R$_N$)—, wherein, R$_N$ may be any substituent group, for example, alkyl such as methyl, ethyl and the like, aromatic group such as phenyl, benzyl and the like);

R$_3$ is one or more substituents on the benzene ring independently selected from hydrogen, alkyl, alkoxy, halogen, amino, cyano, hydroxy, nitro and aryl;

Y is selected from carbon, oxygen, and nitrogen;

In some embodiments, when Y is carbon, it may be (—CH$_2$—), or (—C(R1R2)-, wherein, R1, R2 may be the same or different arbitrary substituent group, such as hydrogen, alkyl such as methyl, ethyl and the like, aromatic group such as phenyl, benzyl and the like, halogen, and the like;

In some embodiments, when Y is nitrogen, it may be (—NH—), or (—N(R$_N$)—, wherein R$_N$ may be any substituent groups, e.g. alkyl such as methyl, ethyl and the like, aromatic group such as phenyl, benzyl and the like);

R$_4$ is selected from alkyl, alkoxy, aryl, benzyl and derivatives thereof;

R$_5$ is selected from hydrogen, alkyl, aryl, benzyl and derivatives thereof;

the substituent groups represented by G1 and G2 are disposed on the benzene ring in meta, para or ortho position.

In the preferred embodiments, the invention provides a phosphorus-containing compound which is further characterized in that the above aryl group is selected from phenyl group and derivatives thereof, naphthyl group and derivatives thereof, N or O containing heteroaryl group and derivatives thereof, N or O containing heterocyclic naphthyl group and derivatives thereof;

wherein, the above derivatives refer to the aromatic ring having one or more independently substituted hydrogen, alkyl, alkoxy, halogen, amino, cyano, hydroxy, nitro, aryl, alkylsulfonyl or phenylsulfonyl thereon.

Further, the invention provides a phosphorus-containing compound which is further characterized in that X is selected from imino (—NH—) and amine (—N(R3)-);

the above Y is selected from (—NH—), amine (—N(R$_N$)—), and ammonium (—N$^+$(R4R5)-, wherein R$_N$ may be any substituent group, such as: alkyl such as methyl, ethyl and the like, aromatic group such as phenyl, benzyl and the like, R4 and R5 can be the same or different arbitrary substituent groups, e.g. alkyl group such as methyl, ethyl and the like, aromatic group such as phenyl, benzyl and the like, the anion coordinated to N$^+$ may be selected from halogen.

Further, the invention provides a phosphorus-containing compound characterized in that:

the above R$_4$ is selected from the group consisting of the following structures:

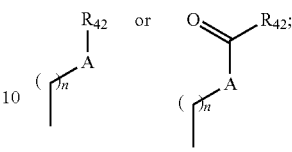

n is selected from an integer from 0 to 5;

the above A is selected from sulfur, carbon, nitrogen, and oxygen;

the above R$_{42}$ is selected from aryl, alkyl, alkylamino, alkylsulfonylamino, cycloalkyl, substituted cycloalkyl, heterocycloalkyl, substituted heterocycloalkyl;

wherein the above aryl group is selected from 6-12 membered aromatic groups and derivatives thereof, heteroaryl with one or more carbon atoms on the 5-12 membered aromatic ring substituted by oxygen, nitrogen or sulfur;

wherein, the above derivatives refer to the aromatic ring group having one or more substituted hydrogen, alkyl, alkoxy, halogen, amino, cyano, hydroxy, nitro, sulfonyl, alkylsulfonyl or phenylsulfonyl thereon.

The above heteroaryl group may further have a structure of —N—R$_{422}$ on it;

the above R$_{422}$ is sulfonyl, alkylsulfonyl, alkyl, or hydroxy;

the above cycloalkyl group is a 3-12 membered cycloalkyl group;

the substituted cycloalkyl group refers to the ring group having one or more independently substituted sulfonyl, alkylsulfonyl, alkyl, alkoxy, hydroxy, amino, nitro;

the heterocycloalkyl group is a 3-12 membered heterocycloalkyl group having one or more carbon atoms substituted by oxygen, nitrogen and sulfur;

the carbon atoms on the heterocycloalkyl can also be substituted by C=O and/or SO and/or SO$_2$;

the substituted heterocycloalkyl group is aza-, oxa- or thiacycloalkyl having a four, five, six or seven membered ring, by which the ring is independently substituted by one or more substituted sulfonyl, alkylsulfonyl, alkyl, alkoxy, hydroxy, amino, nitro and carbonyl;

the substituted heterocycloalkyl group may further have a structure of —N—R$_{422}$ on it;

the above R$_{422}$ is sulfonyl, alkylsulfonyl, alkyl, or hydroxy;

the above R$_{42}$ may also be selected from the groups of the following structures:

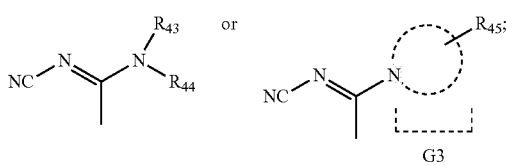

the above R$_{43}$ and R$_{44}$ are the same or different alkyl, hydroxy or hydroxy substituted alkyl having not more than 5 carbon atoms;

G3 is a 3-12 membered ring;

the carbon atom on the ring of G3 may also be partially replaced by oxygen, sulfur, nitrogen, C=O or SO$_2$;

the above R$_{45}$ is one or more substituents on G3 ring selected from alkyl, hydroxy, alkoxy and amino;

In the preferred embodiments, the invention provides a phosphorus-containing compound characterized in that the compound represented by the following structure:

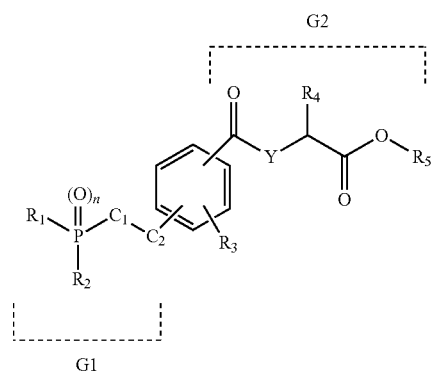

wherein, the above C$_1$ and C$_2$ are both carbon atoms, and the bond in-between is single bond, double bond or triple bond.

In the more preferred embodiments, the invention provides a phosphorus-containing compound characterized in that the compound represented by the following structure:

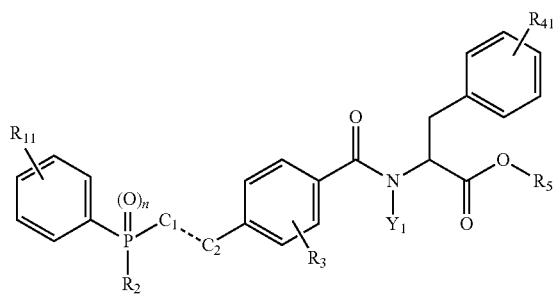

R$_{11}$ is one or more substituents on the benzene ring independently selected from hydrogen, alkyl, alkoxy, halogen, amino, cyano, hydroxy, nitro;

R$_2$ is selected from hydroxy, alkyl, alkoxy and halogen;

R$_3$ is one or more substituents on the benzene ring independently selected from hydrogen, alkyl, alkoxy, halogen, amino, cyano, hydroxy, nitro and aryl;

Y$_1$ is selected from hydrogen, alkyl and aryl;

R$_{41}$ is one or more substituents on the benzene ring independently selected from hydrogen, alkyl, alkoxy, alkylsulfonyl, arylsulfonyl, halogen, amino, cyano, hydroxy, nitro;

R$_5$ is selected from hydrogen, alkyl, aryl, benzyl and derivatives thereof.

In the even more preferred embodiments, the invention provides a phosphorus-containing compound characterized in that the compound represented by the following structure:

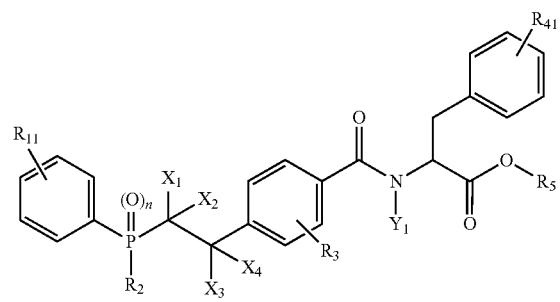

wherein X$_1$, X$_2$, X$_3$, and X$_4$ are selected from hydrogen, alkyl, halogen, and hydroxy.

Further, the invention provides a phosphorus-containing compound characterized in that the phosphorus-containing compound selected from the following:

(2s)-2-(2,6-dichloro-4-(2-(hydroxy(phenyl)phosphoryl) ethyl)benzamido)-3-(3-(methylsulfonyl)phenyl)propionic acid;

(2s)-2-(2,6-dichloro-4-((hydroxy(3-hydroxyphenyl)phosphoryl)ethynyl)benzamido)-3-(3-(methylsulfonyl)phenyl)propionic acid;

(2s)-2-(2,6-dichloro-4-(2-(hydroxy(m-hydroxyphenyl) phosphoryl)ethyl)benzamido)-3-(3-(methylsulfonyl)phenyl)propionic acid;

(2s)-2-(2,6-dichloro-4-(2-(methoxy(phenyl)phosphoryl) ethyl)benzamido)-3-(3-(methylsulfonyl)phenyl)propionic acid;

(2s)-2-(2,6-dichloro-4-(methoxy(phenyl)phosphoryl)ethynyl)benzamido)-3-(3-(methylsulfonyl)phenyl)propionic acid;

(2s)-2-(2,6-dichloro-4-(2-(ethoxy(m-hydroxyphenyl)phosphoryl)ethyl)benzamido)-3-(3-(methylsulfonyl)phenyl) propionic acid;

(2s)-2-(2,6-dichloro-4-((methoxy(3-hydroxyphenyl)phosphoryl)ethynyl)benzamido)-3-(3-(methylsulfonyl)phenyl)propionic acid;

(2s)-2-(2,6-dichloro-4-(2-(methoxy(3-hydroxyphenyl)phosphoryl)ethyl)benzamido)-3-(3-(methylsulfonyl)phenyl) propionic acid;

(2s)-2-(2,6-dichloro-4-(methyl(phenyl)phosphoryl)ethynyl) benzamido)-3-(3-(methylsulfonyl)phenyl)propanoic acid;

(2s)-2-(2,6-dichloro-4-(2-(methyl(phenyl)phosphoryl)ethyl) benzamido)-3-(3-(methylsulfonyl)phenyl)propionic acid;

(2s)-2-(2,6-dichloro-4-((methyl(3-hydroxyphenyl)phosphoryl)ethynyl)benzamido)-3-(3-(methylsulfonyl)phenyl) propionic acid;

(2s)-2-(2,6-dichloro-4-((methoxy(3-methoxyphenyl)phosphoryl)ethynyl)benzamido)-3-(3-(methylsulfonyl)phenyl)propionic acid;

(2s)-2-(2,6-dichloro-4-((hydroxy(3-methoxyphenyl)phosphoryl)ethynyl)benzamido)-3-(3-(methylsulfonyl)phenyl)propionic acid.

In addition, the present invention also provides a method for preparing the above phosphorus-containing compound, which is characterized in that:

it is obtained by reacting Compound A and Compound C with the active sites on Compound B in sequence;

wherein the above compound A is a compound represented by the following structure:

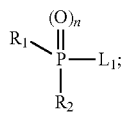

the above compound C is a compound represented by the following structure:

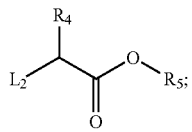

the above compound B is a compound represented by the following structure:

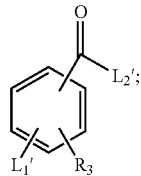

wherein, L1 and L1' as well as L2 and L2' are respectively a pair of active groups which can react with each other, and during the reaction, the target product was obtained through the reaction between $L_1$ and $L_1$', and the reaction between $L_2$ and $L_2$';

$R_1$ is selected from alkyl, aryl, benzyl and derivatives thereof;

$R_2$ is selected from hydroxy, alkyl, alkoxy and halogen;

n is selected from a natural number of 1-3;

$R_3$ is one or more substituents on the benzene ring independently selected from hydrogen, alkyl, alkoxy, halogen, amino, cyano, hydroxy, nitro, aryl;

$R_4$ is selected from alkyl, alkoxy, aryl, benzyl and derivatives thereof;

$R_5$ is selected from hydrogen, alkyl, aryl, benzyl and derivatives thereof.

Further, the method for preparing a phosphorus-containing compound provided by the invention has the characteristics that the substitution reaction, the addition reaction, the elimination reaction or the replacement reaction, can be carried out between the above L1 and L1' as well as between L2 and L2', and connection bonds between L1 and L' as well as between L2 and L2' are formed.

Further, the method for preparing a phosphorus-containing compound provided by the invention further has the characteristic that the above $L_1$ is selected from halogen, amino, cyano, thio, hydroxy and alkoxyl;

the above $L_1$' is selected from halogen, alkynyl, carboxyl, amino, cyano, ester, alkoxyl, sulfonamide, alkoxysulfonyl;

the above $L_2$ is selected from halogen, carboxyl, amino, cyano, ester, alkoxyl, sulfonamide, alkoxysulfonyl;

the above $L_2$' is selected from halogen, amino, thio, hydroxy and alkoxyl.

Further, the method for preparing a phosphorus-containing compound provided by the invention is characterized in that the molar ratio of the above compound A to the compound C is 1:0.1-10;

the molar ratio of the above compound C to the compound B is 1:0.1-10.

Further, the method for preparing a phosphorus-containing compound provided by the invention is further characterized in that, the specific process steps are as follows:

Step 1, adding the halogenating reagent to the phosphodiester derivative, reacting at a temperature of 50-100° C. for 1-5 hours, and evaporated to dryness to obtain the substrate 1;

in this step, it is intended to prepare a substrate having an active reactive group from a phosphodiester derivative, and if the compound A having a reactive group L1 is directly selected, the first step can be omitted.

In the present invention, the phosphodiester derivative is a compound represented by the following structure:

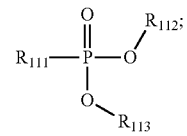

$R_{111}$, $R_{112}$, and $R_{113}$ are selected from aryl (for example, aromatic group such as phenyl, naphthyl, and quinolyl), and alkyl (for example, alkyl such as methyl, ethyl, propyl, isopropyl, cyclohexyl, and cyclopentyl);

the halogenating reagent is generally selected from reagents for providing halogen, such as, thionyl chloride, phosgene or bromine;

the reaction is preferably carried out under the protection of a shielding gas such as nitrogen, argon or helium.

In the reaction, the amount of the added halogenating agent is 0.5 to 4 ml per 100 mg of the phosphodiester derivative.

Step 2: Sequentially adding Grignard reagent and substrate 1 to the derivative of methyl ethynylbenzoate at a temperature below 0° C., reacting for 0.1-2 hours, quenching the reaction with an acidic solution, extracting the organic phase and evaporate to obtain the intermediate product 1;

in the invention, the derivative of methyl ethynylbenzoate is a compound represented by the following structure:

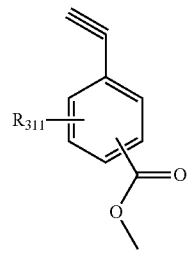

wherein $R_{311}$ is one or more substituents independently selected from halogen, nitro, aryl (for example, aromatic group such as phenyl, naphthyl and quinolyl and the like), alkyl (for example, alkyl group such as methyl, ethyl, propyl, isopropyl, cyclohexyl and cyclopentyl) and the like;

the ethynyl and methyl formate groups may be in the para, ortho or meta position;

the mass ratio of the derivative of methyl ethynylbenzoate to Grignard reagent and substrate 1 is 1:0.01-10:1:–10;

the reaction is preferably carried out under the protection of a shielding gas such as nitrogen, argon or helium;

the reaction is preferably carried out in the ether solvent;

the acid used for quenching the reaction is preferably a mineral acid, the concentration of the acid is preferably from 0.5 to 1.5 mol/L, and the amount of the acid is preferably from 0.01 to 10 times the total amount of the reactant;

the reagent for extraction is preferably an ester solvent.

Step 3, the intermediate product 1 and the de-esterification reagent, react at a temperature of 100-150° C. for 2-5 hours, quenched with the acidic solution, the organic phase from extraction evaporated to dryness, to give the intermediate product 2;

the mass ratio of the intermediate product 1 and the deesterification reagent is 1:0.5-3;

the reaction is preferably carried out under the atmosphere of a protective gas such as nitrogen, argon and helium;

the acid used for the quenching reaction is preferably a mineral acid, the concentration of the acid is preferably from 0.5 to 1.5 mol/L, and the amount of the acid is preferably from 0.01 to 10 times the total amount of the reactant;

the reagent for extraction is preferably the ester solvent.

Step 4, in the intermediate product 2, sequentially adding compound C in which $L_2$ is amino, and the basic catalyst, reacting at a temperature of 20-50° C. for 1-10 hours, quenching the reaction with an acid solution, and the extracted organic phase was evaporated to dryness to give a phosphorus-containing compound containing alkynyl group.

The molar ratio of the intermediate product 2, the compound C and the basic catalyst is 1:1-5:5-20;

the acid used for quenching the reaction is preferably a mineral acid, the concentration of the acid is preferably from 0.5 to 1.5 mol/L, and the amount of the acid is preferably from 0.01 to 10 times the total amount of the reactant;

the reagent for extraction is preferably the ester solvent.

The above reaction procedures are all applicable to the scheme in which the next step is carried out without purification, and the yield in each step is about 50 to 95%, and the total yield is about 50 to 80%.

The specific equations for the above process are as follows:

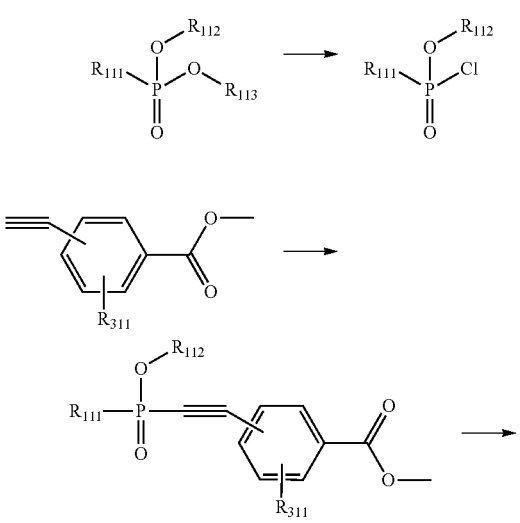

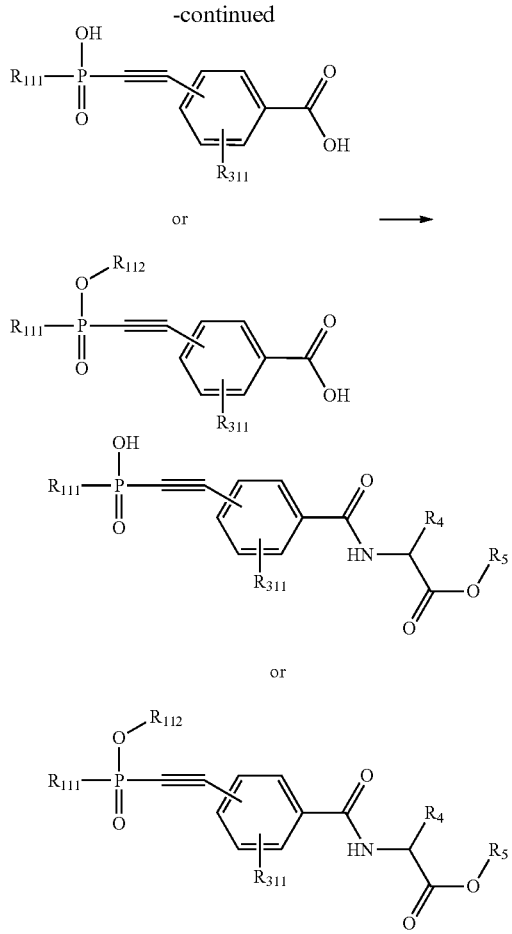

Further, the method for preparing a phosphorus-containing compound provided by the invention is further characterized in that, the above alkynyl-containing phosphorus-containing compound undergoes one or more reactions selected from reduction reaction, esterification reaction, amidation reaction, substitution reaction and addition reaction, and the corresponding phosphorus-containing product can be obtained.

Further, the invention provides the application of the above phosphorus-containing compound, in particular, that it can be used as an immune cell migration inhibitor.

Further, the invention provides the application of the above phosphorus-containing compound, in particular, that the eye drops containing the above phosphorus-containing compound can be used for alleviating and treating dry eye syndrome.

The method for preparing the eye drop preparation can be any conventional preparation method.

For example, the above compound is added to 10-200 times by weight of the sterile physiological saline, 0.01-1 times of alkali solution is added, stirring to a transparent solution; and the buffer solution is added to the above obtained solution until the pH of the solution is between 6.5-7.5; and then the sterile physiological saline is added into the obtained aqueous solution until the total volume reaches 1.5-20 times of the original volume. The above solution is then purged with nitrogen, bubbling for 0.5-10 hours, and the resulting solution is sealed and stored at 5° C. under exclusion of light. The solution is dispensed into a disposable eye drop vessel for use. Among them, the above saturated aqueous solution of sodium hydroxide and $NaH_2PO_4$ can be replaced by other buffer solutions.

Action and Effect of the Invention

In the invention, a new class of phosphorus-containing compounds is synthesized, which is a novel immune cell migration inhibitor. It has good hydrophilicity, is easy to develop into eye drops, has a strong inhibitory effect on immune cell migration, and it may alleviate the symptoms of most dry eye patients.

DESCRIPTION OF THE EMBODIMENTS

Example 1

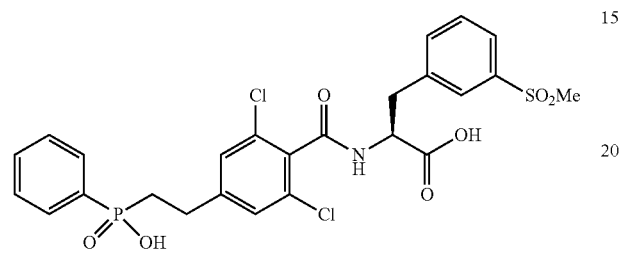

(2s)-2-(2,6-dichloro-4-(2-(hydroxy(phenyl)phosphoryl)ethyl)benzamido)-3-(3-(methylsulfonyl)phenyl)propionic Acid The specific reaction equation is as follows:

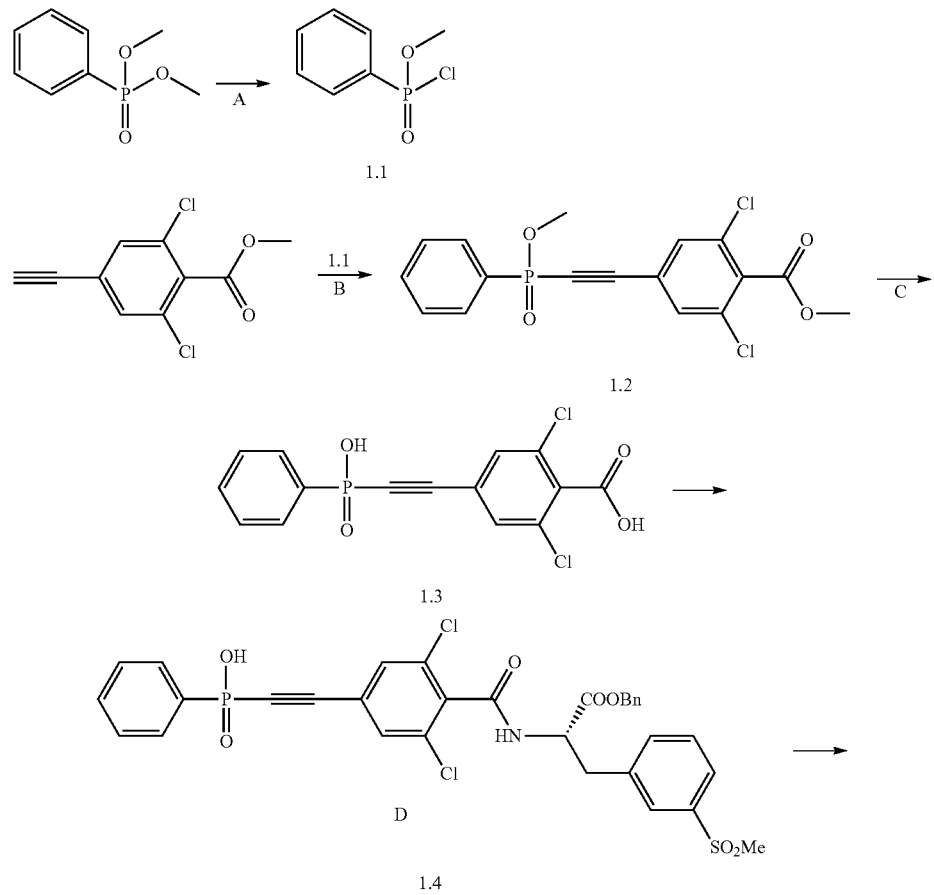

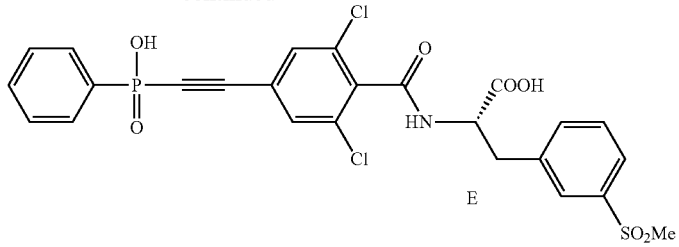

1

Step A: methoxyphenylphosphoryl chloride (Compound 1.1)

150 mg of dimethyl phenyl phosphate was weighed, 4 ml of thionyl chloride was added, protected with nitrogen, they react at 75° C. for 2 hours, and were directly spun-dried.

Step B: Methyl 2,6-dichloro-4-((phenyl(methoxy)phosphoryl)ethynyl)benzoate (Compound 1.2)

50 mg of methyl 2,6-dichloro-4-ethynylbenzoate was dissolved in 1 ml of tetrahydrofuran, protected with nitrogen, and 0.2 ml of isopropylmagnesium chloride (2 mol/L) was added at 0° C., and stirred for 20 minutes; Compound 1.1 was dissolved in 0.5 ml of tetrahydrofuran and added, reacted for 20 minutes. The reaction was quenched by 1 mol/L dilute HCl solution, and was extracted three times with 30 mL ethyl acetate, the organic phases were combined, spun-dried, and purified to obtain the product (50 mg, 60%).
LCMS ESI (+) m/z: 382.6 (M+1).

Step C: 2,6-dichloro-4-((hydroxy(phenyl)phosphoryl)ethynyl)benzoic Acid (Compound 1.3)

Compound 1.2 (50 mg) and lithium iodide (50 mg) were dissolved in 1 ml of pyridine, protected with nitrogen, stirred at 120° C. for 3 hours, cooled and spun-dried, and 10 ml of 1 mol/L dilute HCl solution was added. Extraction was carried out three times with 30 ml of ethyl acetate, and the organic phases were combined and spun-dried without further purification.
LCMS ESI (+) m/z: 354.6 (M+1).

Step D: (2s)-2-(2,6-dichloro-4-((hydroxy(phenyl)phosphoryl)ethynyl)benzamido)-3-(3-(methylsulfonyl)phenyl)benzyl propionate (Compound 1.4)

Compound 1.3 was dissolved in DMF, benzyl (2s)-2-amino-3-(3-(methylsulfonyl)phenyl)propionate hydrochloride (2 eq) was added, then followed by DIPEA (10 eq), HATU (2.5 eq). After stirring at normal temperature for 4 h, 10 ml of dilute HCl solution was added, extracted three times with EA, the organic phases were combined and spun-dried. Purification was prepared with the reverse phase, spun-dried at 45° C. under reduced pressure to obtain 40 mg of the target product.
LCMS ESI (+) m/z: 669.5 (M+1).

Step E: (2s)-2-(2,6-dichloro-4-(2-(hydroxy(phenyl)phosphoryl)ethyl)benzamido)-3-(3-(methylsulfonyl)phenyl)propionic Acid (Compound 1)

Compound 1.4 was dissolved in 1 ml of methanol, Pd/C (10%, 0.1 eq) was added, and then hydrogenated under normal pressure for 1 h, filtered, spun-dried, prepared by reverse phase, and 10 mg of lyophilized product was obtained. LCMS ESI (+) m/z: 583.6 (M+1); $^1$H-NMR (400 MHz, DMSO) δ 9.02 (d, J=8 Hz, 1H), 7.86 (s, 1H), 7.77 (m, 3H), 7.66 (m, 1H), 7.55 (m, 2H) 7.51 (m, 2H), 7.29 (s, 2H), 4.75 (m, 1H), 3.29 (dd, J=15 Hz, J=4.4 Hz, 1H), 3.15 (s, 3H), 3.03 (dd, J=15.5 Hz, J=10.4 Hz, 1H), 2.70 (m, 2H), 2.11 (m, 2H).

Example 2

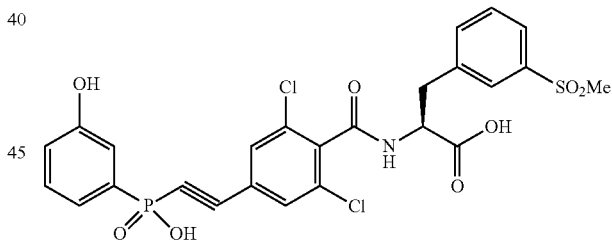

(2s)-2-(2,6-dichloro-4-((hydroxy(3-hydroxyphenyl)phosphoryl)ethynyl)benzylamino)-3-(3-(methylsulfonyl)phenyl)propionic Acid The specific reaction equation is as follows:

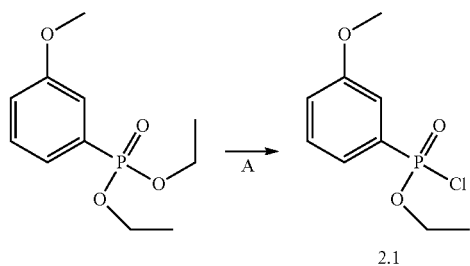

2.1

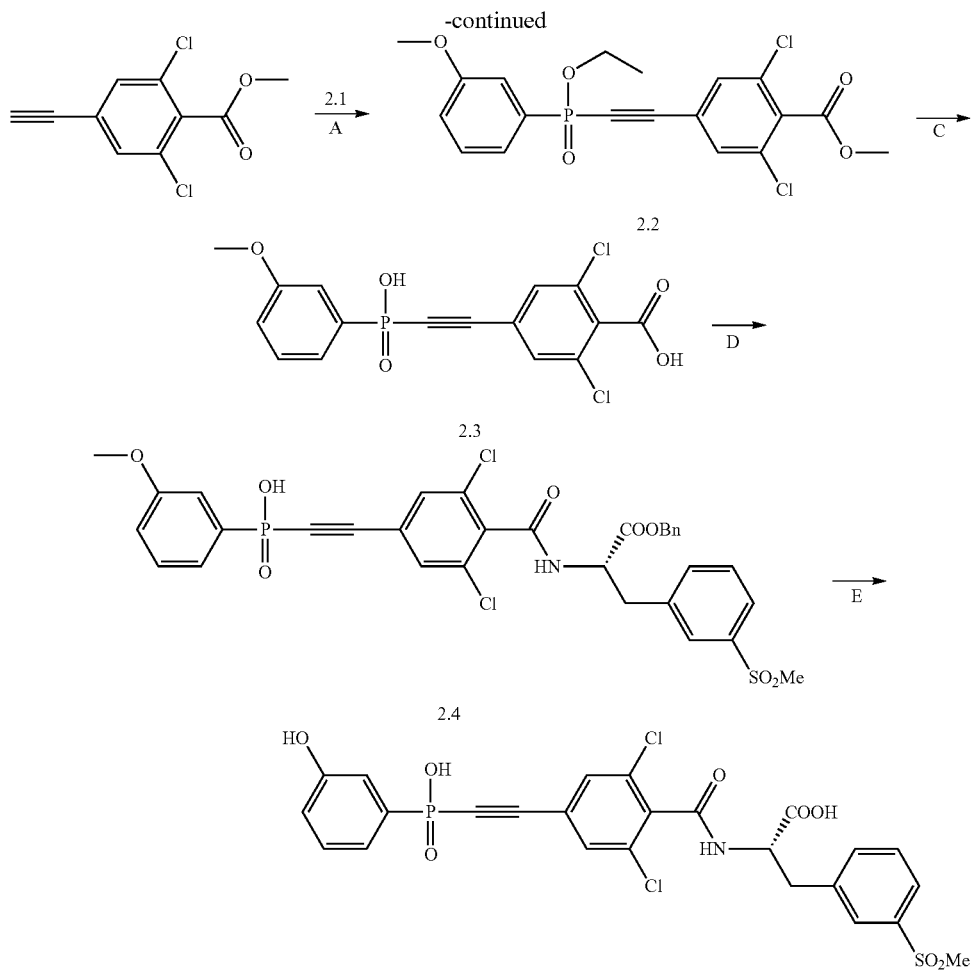

Step A: (m-methoxyphenyl)ethoxyphosphoryl chloride (Compound 2.1)

200 mg of diethyl m-methoxyphenyl phosphate was weighed, and 4 ml of thionyl chloride was added, protected with nitrogen, and reacted at 75° C. for 12 hours, and then directly spun-dried.

Step B: methyl 2,6-dichloro-4-(((m-methoxyphenyl)(ethoxy)phosphoryl)ethynyl)benzoate (Compound 2.2)

100 mg of methyl 2,6-dichloro-4-ethynylbenzoate was dissolved in 1.5 ml of tetrahydrofuran, protected with nitrogen, and 0.7 ml of 2 mol/L of isopropyl magnesium chloride was added at 0° C., and stirred for 20 minutes; Compound 2.1 was dissolved in 0.5 ml of tetrahydrofuran and reacted for 20 minutes. The reaction was quenched with 1 mol/L dilute HCl solution, and extracted three times with 30 mL ethyl acetate, the organic phases are combined, spun-dried, and purified to obtain the product (100 mg, 60%).

LCMS ESI (+) m/z: 426.6 (M+1).

Step C: 2,6-dichloro-4-((hydroxy(m-methoxyphenyl)phosphoryl)ethynyl)benzoic Acid (Compound 2.3)

Compound 2.2 (100 mg) and lithium iodide (100 mg) were dissolved in 2 ml of pyridine, protected with nitrogen, stirred at 120° C. for 3 hours, cooled and spun-dried, and 10 ml of 1 mol/L dilute HCl solution was added. Extraction was carried out three times with 30 ml of ethyl acetate, the organic phases were combined and spun-dried without further purification.

LCMS ESI (+) m/z: 384.6 (M+1).

Step D: benzyl (2s)-2-(2,6-dichloro-4-((hydroxy(m-methoxyphenyl)phosphoryl)ethynyl)benzamido)-3-(3-(methylsulfonyl)phenyl)propionate (Compound 2.4)

Compound 2.3 was dissolved in DMF, and benzyl (2s)-2-amino-3-(3-(methylsulfonyl)phenyl)propionate hydrochloride (2 eq) was added, then followed by DIPEA (10 eq), and HATU (2.5 eq). After stirring at normal temperature for 4 h, 10 ml of dilute HCl solution was added. Extraction was carried out three times with EA, and the organic phases were combined and spun-dried. Purification was prepared by reverse phase, spun-dried at 45° C. under reduced pressure to give the target product, 80 mg.

LCMS ESI (+) m/z: 699.5 (M+1).

Step E: (2s)-2-(2,6-dichloro-4-((hydroxy(3-hydroxy-phenyl)phosphoryl)ethynyl)benzylamino)-3-(3-(methylsulfonyl)phenyl)propionic Acid (Compound 2)

Compound 2.4 (40 mg) was dissolved in 1 ml of DCM, protected with nitrogen, and 0.2 ml of boron tribromide (1 mol/L) was added at −40° C., and then stirred at 0° C. for 30 minutes. The reaction was quenched by adding water at −40°, extracted with 30 mL of EA, dried over anhydrous sodium sulfate, spun-dried and purified to obtain 15 mg of product.

LCMS ESI (+) m/z: 595.5 (M+1).

$^1$H-NMR (400 MHz, DMSO), δ9.16 (d, J=8.4 Hz, 1H), 7.86 (s, 1H), 7.76 (d, J=7.6 Hz, 1H), 7.67 (d, J=7.6 Hz, 1H), 7.56 (dd, J=8 Hz, J=7.6 Hz, 1H), 7.44 (s, 2H), 7.28 (m, 1H), 7.16 (m, 2H), 6.77 (m, 1H), 4.78 (m, 1H), 3.29 (m, 1H), 3.14 (s, 3H), 3.01 (dd, J=14, J=10.4, 1H).

Example 3

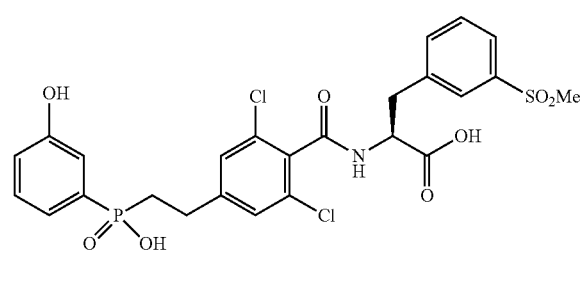 [SMILES: CS(=O)(=O)c1cccc(C[C@H](NC(=O)c2c(Cl)cc(CCP(=O)(O)c3cccc(O)c3)cc2Cl)C(=O)O)c1]

(2s)-2-(2,6-dichloro-4-(2-(hydroxy(m-hydroxyphenyl)phosphoryl)ethyl)benzamido)-3-(3-(methylsulfonyl)phenyl)propionic Acid The specific reaction equation is as follows:

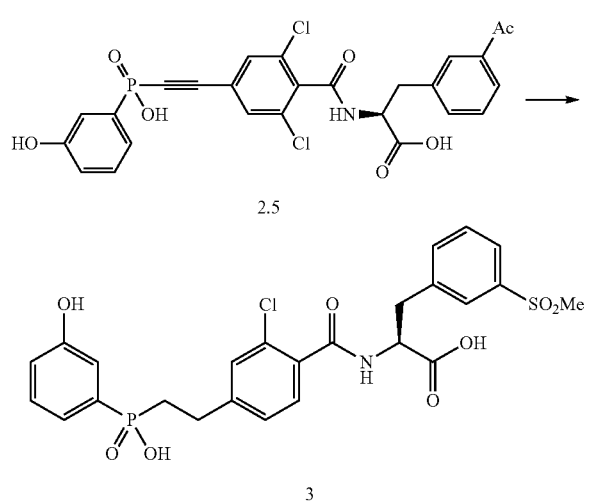

Compound 2.5 (10 mg) was dissolved in 1 ml of methanol, and 1 mg of Pd/C (10%) was added, and hydrogenated at normal pressure for 1.5 h, then filtered. The product was spun-dried and purified to give 3 mg of product.

LCMS ESI (+) m/z: 599.6 (M+1). $^1$H-NMR (400 MHz, DMSO), δ9.72 (s, 1H), 9.04 (d, J=8.4 Hz, 1H), 7.86 (s, 1H), 7.77 (d, J=8 Hz, 1H), 7.67 (d, J=7.6 Hz, 1H), 7.56 (t, J=7.6 Hz, 1H), 7.33 (m, 1H), 7.28 (s, 2H), 7.15 (m, 2H), 6.93 (m, 1H), 4.75 (m, 1H), 3.30 (m, 1H), 3.15 (s, 3H), 3.01 (dd, J=10.8 Hz, J=9.6 Hz, 1H), 2.69 (m, 2H), 2.04 (m, 2H).

Example 4

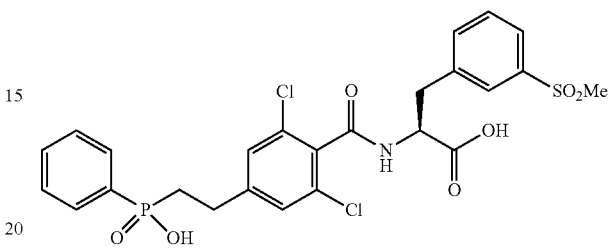

(2s)-2-(2,6-dichloro-4-(2-(methoxy(phenyl)phosphoryl)ethyl)benzamido)-3-(3-(methylsulfonyl)phenyl)propionic Acid The specific reaction equation is as follows:

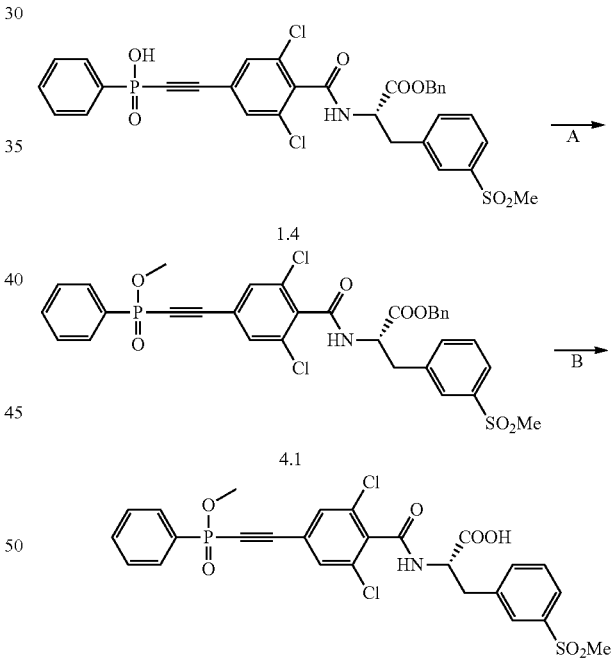

Step A: benzyl (2s)-2-(2,6-dichloro-4-((methoxy(phenyl)phosphoryl)ethynyl)benzamido)-3-(3-(methylsulfonyl)phenyl)propionate (Compound 4.1)

Compound 1.4 (20 mg) was dissolved in 0.5 ml of methanol, trimethylsilyldiazomethane (3 eq) was added, and stirred at room temperature for 30 minutes. The reaction was quenched with an appropriate amount of acetic acid, spun-dried, and 5 ml of dilute HCl solution was added. The extraction was carried out three times with EA, and the organic phases were combined, and spun-dried. LCMS ESI (+) m/z: 683.6 (M+1).

Step B: (2s)-2-(2,6-dichloro-4-(2-(methoxy(phenyl) phosphoryl)ethyl)benzamido)-3-(3-(methylsulfonyl) phenyl)propionic Acid (Compound 4)

Compound 4.1 was dissolved in methanol (1 ml), and 1 mg of Pd/C (10%) was added thereto, and the mixture was hydrogenated at normal pressure for 1 hour, filtered, spun-dried and purified to obtain the target product.
LCMS ESI (+) m/z: 597.6 (M+1).
$^1$H-NMR (400 MHz, DMSO) δ9.03 (d, J=8.4 Hz, 1H), 7.86 (s, 1H), 7.75 (m, 3H), 7.66 (m, 2H), 7.56 (m, 3H), 7.32 (s, 2H), 4.75 (m, 1H), 3.51 (d, J=11.2 Hz, 3H), 3.28 (dd, J=14.4 Hz, J=3.6 Hz, 1H), 3.15 (s, 3H), 3.01 (dd, J=14.4 Hz, J=10.8 Hz, 1H), 2.72 (m, 2H), 2.34 (m, 2H).

Example 5

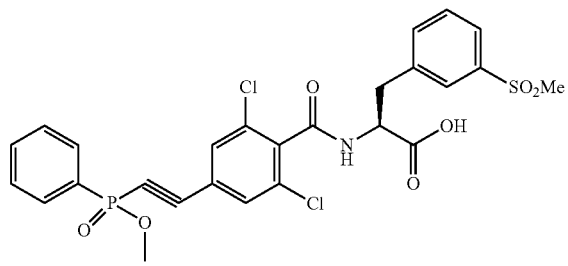 [SMILES: COP(=O)(C#Cc1cc(Cl)c(C(=O)N[C@@H](Cc2cccc(S(C)(=O)=O)c2)C(=O)O)c(Cl)c1)c1ccccc1]

(2s)-2-(2,6-dichloro-4-(methoxy(phenyl)phosphoryl) ethynyl)benzamido)-3-(3-(methylsulfonyl)phenyl) propanoic Acid The specific reaction equation is as follows:

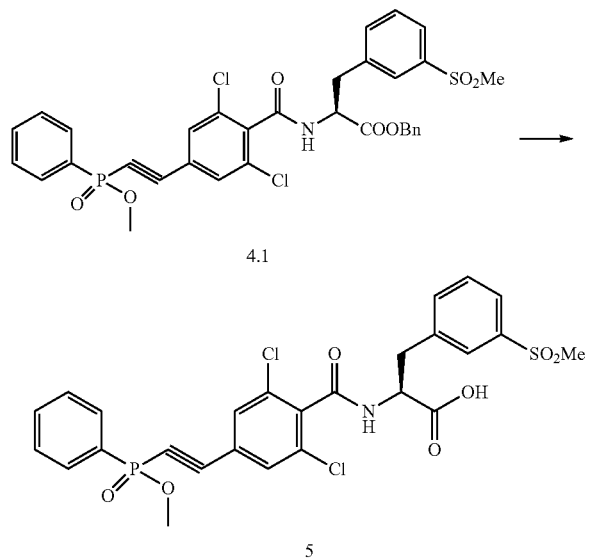

Compound 4.1 was dissolved in DCM, and 1 mol/L of boron tribromide (10 eq) was added at −40° C., stirred at 0° C. for 30 minutes and then the reaction was quenched with water at −40° C. The reaction was extracted 3 times with EA, and the organic phases were combined, spun-dried and purified to give the target product. LCMS ESI (+) m/z: 593.6 (M+1).
1H-NMR (400 MHz, DMSO) δ9.21 (d, J=8.4 Hz, 1H), 7.88 (m, 5H), 7.77 (m, 1H), 7.72 (m, 1H), 7.67 (m, 1H), 7.63 (m, 2H), 7.57 (m, 1H), 3.83 (d, J=12.4 Hz, 3H), 3.30 (m, 1H), 3.15 (s, 3H), 3.03 (dd, J=13.6 Hz, J=10.4 Hz, 1H).

Example 6

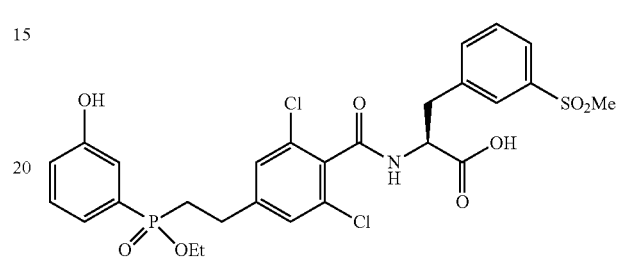

(2s)-2-(2,6-dichloro-4-(2-(ethoxy(m-hydroxyphenyl) phosphoryl)ethyl)benzamido)-3-(3-(methylsulfonyl) phenyl)propionic Acid The specific reaction equation is as follows:

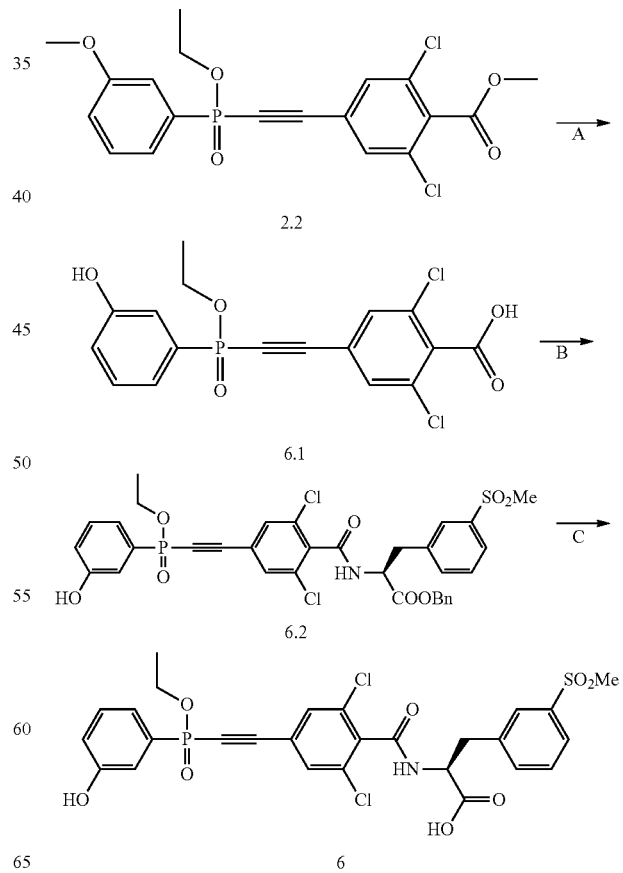

Step A: 2,6-dichloro-4-(((m-hydroxyphenyl)(ethoxy)phosphoryl)ethynyl)benzoic Acid (Compound 6.1)

Compound 2.2 was dissolved in DCM, and 1 mol/L of boron tribromide (10 eq) was added at low temperature, and stirred at 0° C. for 30 minutes, then the reaction was quenched at −40° C., extracted with EA three times, and the organic phases were combined, and spun-dried.

LCMS ESI (+) m/z: 398.6 (M+1).

Step B: benzyl (2s)-2-(2,6-dichloro-4-((ethoxy(m-hydroxyphenyl)phosphoryl)ethynyl)benzamido)-3-(3-(methylsulfonyl)phenyl)propionate (Compound 6.2)

Compound 6.1 was dissolved in DMF, and benzyl (2s)-2-amino-3-(3-(methylsulfonyl)phenyl)propionate hydrochloride (2 eq) was added, followed by DIPEA (10 eq), and HATU (2.5 eq). After stirring at normal temperature for 4 h, and 10 ml of dilute HCl solution was added, extracted with EA three times, and the organic phases were combined and spun-dried. Purification was prepared by reverse phase, spun-dried at 45° C. under reduced pressure to give the target product.

LCMS ESI (+) m/z: 713.5 (M+1).

Step C: (2s)-2-(2,6-dichloro-4-(2-(ethoxy(m-hydroxyphenyl)phosphoryl)ethyl)benzamido)-3-(3-(methylsulfonyl)phenyl)propionic Acid (Compound 6)

Compound 6.2 was dissolved in 1 ml of methanol, and Pd/C (10%, 0.1 eq) was added, and the mixture was hydrogenated under normal pressure for 1 h, filtered, spun-dried and purified to give the product.

LCMS ESI (+) m/z: 627.5 (M+1).

$^1$H-NMR (400 MHz, DMSO) δ9.85 (s, 1H), 9.05 (d, J=5.6 Hz, 1H), 7.86 (s, 1H), 7.76 (d, J=4.8 Hz, 1H), 7.66 (d, J=4.8 Hz, 1H), 7.57 (dd, J=5.2 Hz, J=5.2 Hz, 1H), 7.35 (m, 1H), 7.33 (s, 2H), 7.16 (m, 2H), 6.98 (m, 1H), 4.75 (m, 1H), 3.91 (m, 1H), 3.78 (m, 1H), 3.30 (m, 1H), 3.15 (s, 3H), 3.01 (m, 1H), 2.70 (m, 2H), 2.25 (m, 2H) 1.19 (t, J=4.8 Hz, 3H).

Example 7

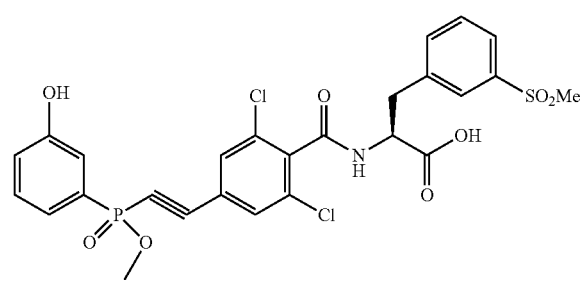 [SMILES: COP(=O)(C#Cc1cc(Cl)c(C(=O)N[C@@H](Cc2cccc(S(C)(=O)=O)c2)C(=O)O)c(Cl)c1)c1cccc(O)c1]

(2s)-2-(2,6-dichloro-4-((methoxy(3-hydroxyphenyl)phosphoryl)ethynyl)benzylamino)-3-(3-(methylsulfonyl)phenyl)propionic Acid The specific reaction equation is as follows:

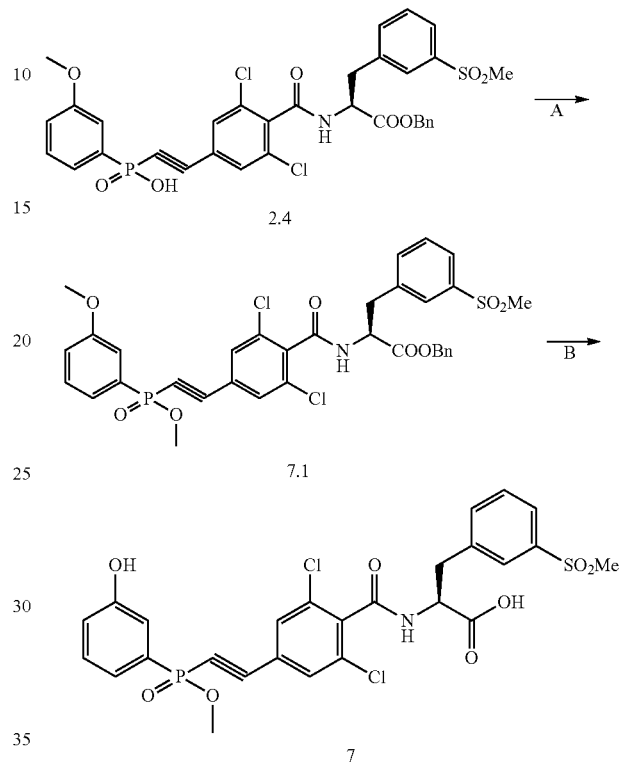

Step A: benzyl (2s)-2-(2,6-dichloro-4-((methoxy(3-hydroxyphenyl)phosphoryl)ethynyl)benzylamino)-3-(3-(methylsulfonyl)phenyl)propanoate (Compound 7.1)

Compound 2.4 (40 mg) was dissolved in 1 ml of methanol, and trimethylsilyldiazomethane (3 eq) was added, and the mixture was stirred at room temperature for 30 minutes. The reaction was quenched with an appropriate amount of acetic acid, spun-dried, and 5 ml of dilute HCl solution was added. It was extracted 3 times with EA, and the organic phases were combined and spun-dried.

LCMS ESI (+) m/z: 713.5 (M+1).

Step B: (2s)-2-(2,6-dichloro-4-((methoxy(3-hydroxyphenyl)phosphoryl)ethynyl)benzylamino)-3-(3-(methylsulfonyl)phenyl)propionic Acid (Compound 7)

Compound 7.1 (30 mg) was dissolved in DCM, and 1 mol/L of boron tribromide (10 eq) was added at −40° C., stirred at 0° C. for 30 minutes and then the reaction was quenched with water at −40° C. It was extracted 3 times with EA, and the organic phases were combined, dried and spun-dried to give 15 mg of the target product.

LCMS ESI (+) m/z: 609.5 (M+1).

$^1$H-NMR (400 MHz, DMSO) δ 10.05 (s, 1H), 7.85 (s, 3H), 7.76 (d, J=8 Hz, 1H), 7.67 (d, J=7.6 Hz, 1H), 7.56 (dd, J=8 Hz, J=7.6 Hz, 1H), 7.42 (m, 1H), 7.29 (m, 1H), 7.25 (m,

1H), 7.07 (m, 1H), 4.75 (m, 1H), 3.80 (d, J=12.4 Hz, 3H), 3.30 (m, 1H), 3.15 (s, 3H), 3.04 (m, 1H).

Example 8

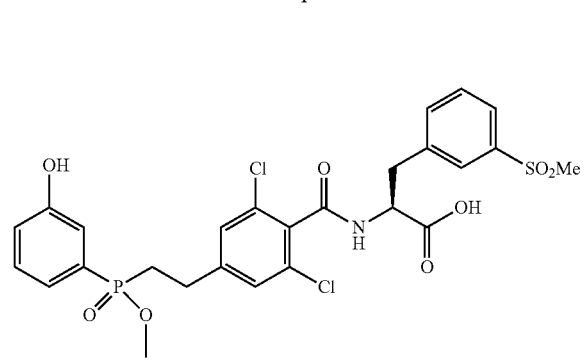

(2s)-2-(2,6-dichloro-4-(2-(methoxy(3-hydroxyphenyl)phosphoryl)ethyl)benzylamido)-3-(3-(methylsulfonyl)phenyl)propionic Acid The specific reaction equation is as follows:

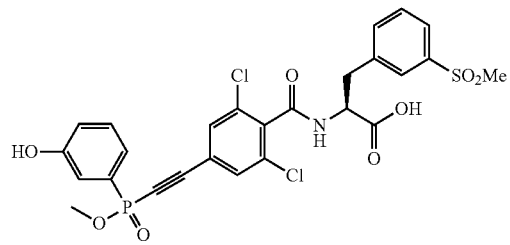

Compound 7.2 (10 mg) was dissolved in methanol (1 ml), 1 mg of Pd/C (10%) was added, the mixture was hydrogenated under normal pressure for 1 hour, filtered and spun-dried, purified to give 4 mg of target product.

LCMS ESI (+) m/z: 613.6 (M+1).

$^1$H-NMR (400 MHz, DMSO) δ 9.87 (s, 1H), 9.04 (d, J=8.4 Hz, 1H), 7.86 (s, 1H), 7.77 (d, J=8 Hz, 1H), 7.67 (d, J=7.6 Hz, 1H), 7.56 (dd, J=8 Hz, J=7.6 Hz, 1H), 7.37 (m, 1H), 7.34 (s, 2H), 7.15 (m, 2H), 7.00 (m, 1H), 4.75 (m, 1H), 3.50 (d, J=11.6 Hz, 3H), 3.27 (m, 1H), 3.15 (s, 3H), 3.01 (m, 1H), 2.72 (m, 2H), 2.30 (m, 2H).

Example 9

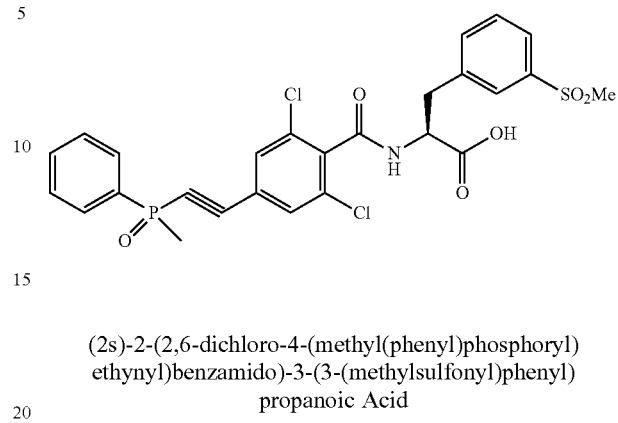

(2s)-2-(2,6-dichloro-4-(methyl(phenyl)phosphoryl)ethynyl)benzamido)-3-(3-(methylsulfonyl)phenyl)propanoic Acid The specific reaction equation is as follows:

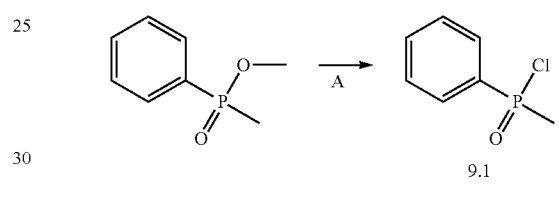

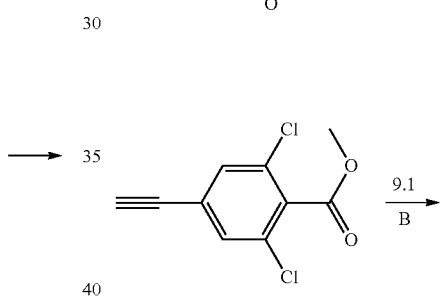

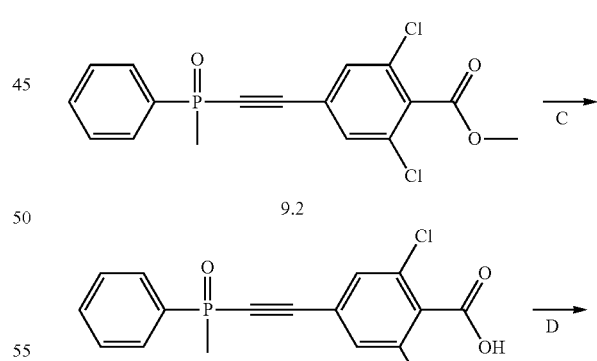

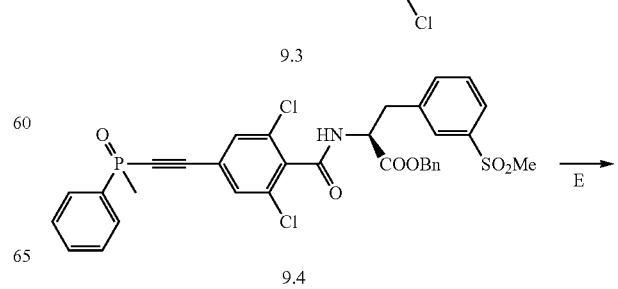

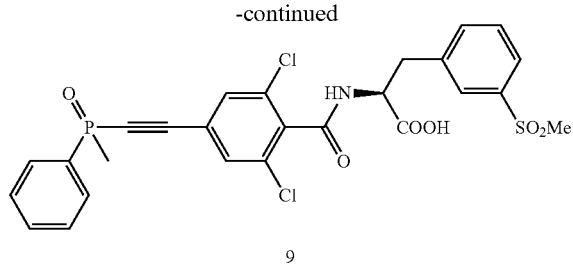

9

Step A: Methylphenylphosphoryl Chloride (Compound 9.1)

500 mg of methyl methylphenyl phosphate was weighed, and 10 ml of thionyl chloride was added, protected with nitrogen. The reaction was performed at 75° C. for 2 hours, and then spun-dried directly.

Step B: methyl 2,6-dichloro-4-((phenyl(methyl)phosphoryl)ethynyl)benzoate (Compound 9.2)

200 mg of methyl 2,6-dichloro-4-ethynylbenzoate was dissolved in 2 ml of tetrahydrofuran, protected with nitrogen, and 0.66 ml of 2 mol/L isopropyl magnesium chloride was added at 0° C., and stirred for 20 minutes; Compound 9.1 was dissolved in 0.5 ml of tetrahydrofuran and added, the reaction was performed for 20 minutes. The reaction was quenched with 1 mol/L dilute HCl solution, extracted three times with 30 mL ethyl acetate, the organic phases were combined, spun-dried and purified to obtain the product (200 mg, 60%).
LCMS ESI (+) m/z: 366.6 (M+1).

Step C: 2,6-dichloro-4-((methyl(phenyl)phosphoryl)ethynyl)benzoic Acid (Compound 9.3)

Compound 9.2 (200 mg) and lithium iodide (200 mg) were dissolved in 2 ml of pyridine, protected with nitrogen, stirred at 120° C. for 3 hours, cooled and spun-dried, and 10 ml of 1 mol/L dilute HCl solution was added. It was extracted three times with 40 mL of ethyl acetate, and the organic phases were combined, spun-dried without purification (150 mg). LCMS ESI (+) m/z: 352.6 (M+1).

Step D: benzyl (2s)-2-(2,6-dichloro-4-((methyl(phenyl)phosphoryl)ethynyl)benzamido)-3-(3-(methylsulfonyl)phenyl)propionate (Compound 9.4)

Compound 9.3 was dissolved in DMF, and benzyl (2s)-2-amino-3-(3-(methylsulfonyl)phenyl)propanoic acid hydrochloride (2 eq) was added, followed by DIPEA (10 eq), and HATU (2.5 eq). After stirring at normal temperature for 4 h, 10 ml of dilute hydrochloric acid solution was added. It was extracted three times with EA, and the organic phases were combined, spun-dried, and purified to give 150 mg of the target product. LCMS ESI (+) m/z: 667.5 (M+1).

Step E: (2s)-2-(2,6-dichloro-4-((methyl(phenyl)phosphoryl)ethynyl)benzamido)-3-(3-(methylsulfonyl)phenyl)propionic Acid (Compound 9)

Compound 9.4 (20 mg) was dissolved in DCM and 1 mol/L boron tribromide (10 eq) was added at low temperature, stirred at 0° C. for 30 minutes, then the reaction was quenched at −40° C., extracted three times with EA, and the organic phases were combined, spun-dried, and purified to give 10 mg of the target product. LCMS ESI (+) m/z: 577.6 (M+1).
$^{1}$H-NMR (400 MHz, DMSO) δ 9.21 (d, J=8.4 Hz, 1H), 7.91 (m, 2H), 7.86 (s, 1H), 7.80 (s, 2H), 7.77 (d, J=4.4 Hz, 1H), 7.67 (m, 2H), 7.62 (m, 2H), 7.57 (m, 1H), 4.80 (m, 1H), 3.29 (m, 1H), 3.15 (s, 3H), 3.03 (m, 1H), 2.02 (d, J=14.8 Hz, 3H), 2.11 (m, 2H).

Example 10

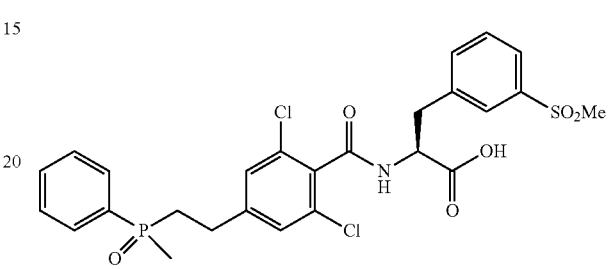

(2s)-2-(2,6-dichloro-4-(2-(methyl(phenyl)phosphoryl)ethyl)benzamide)-3-(3-(methylsulfonyl)phenyl) propionic Acid The specific reaction equation is as follows:

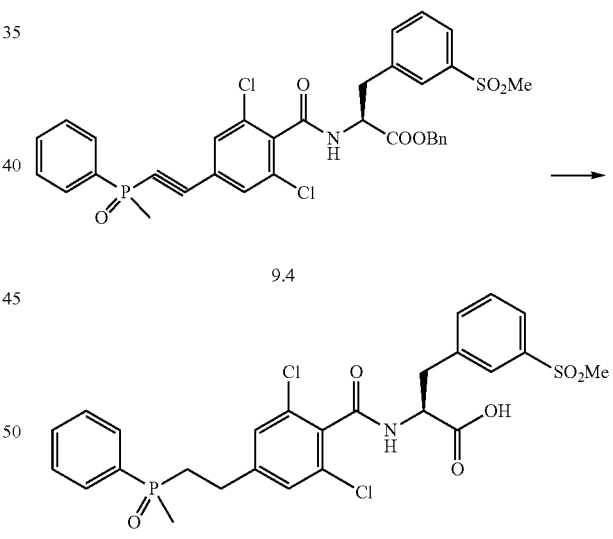

Compound 9.4 (10 mg) was dissolved in methanol (1 ml), and 1 mg of Pd/C (10%) was added, the mixture was hydrogenated under normal pressure for 1 hour, filtered and spun-dried, purified to give 3 mg of the target product. LCMS ESI (+) m/z: 581.6 (M+1).
$^{1}$H-NMR (400 MHz, DMSO) δ 9.04 (d, J=8.4 Hz, 1H), 7.86 (s, 1H), 7.78 (m, 3H), 7.67 (d, J=7.6 Hz, 1H), 7.56 (m, 4H), 7.31 (s, 2H), 4.75 (m, 1H), 3.27 (m, 1H), 3.15 (s, 3H), 3.01 (dd, J=14 Hz, 10.4 Hz, 1H), 2.79 (m, 2H), 2.29 (m, 2H), 1.67 (d, J=13.4 Hz, 3H).

Example 11

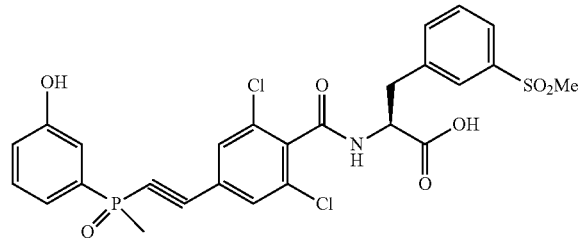 [SMILES: CP(=O)(C#Cc1cc(Cl)c(C(=O)N[C@@H](Cc2cccc(S(C)(=O)=O)c2)C(=O)O)c(Cl)c1)c1cccc(O)c1]

(2s)-2-(2,6-dichloro-4-((methyl(3-hydroxyphenyl)phosphoryl)ethynyl)benzylamino)-3-(3-(methylsulfonyl)phenyl)propionic Acid The specific reaction equation is as follows:

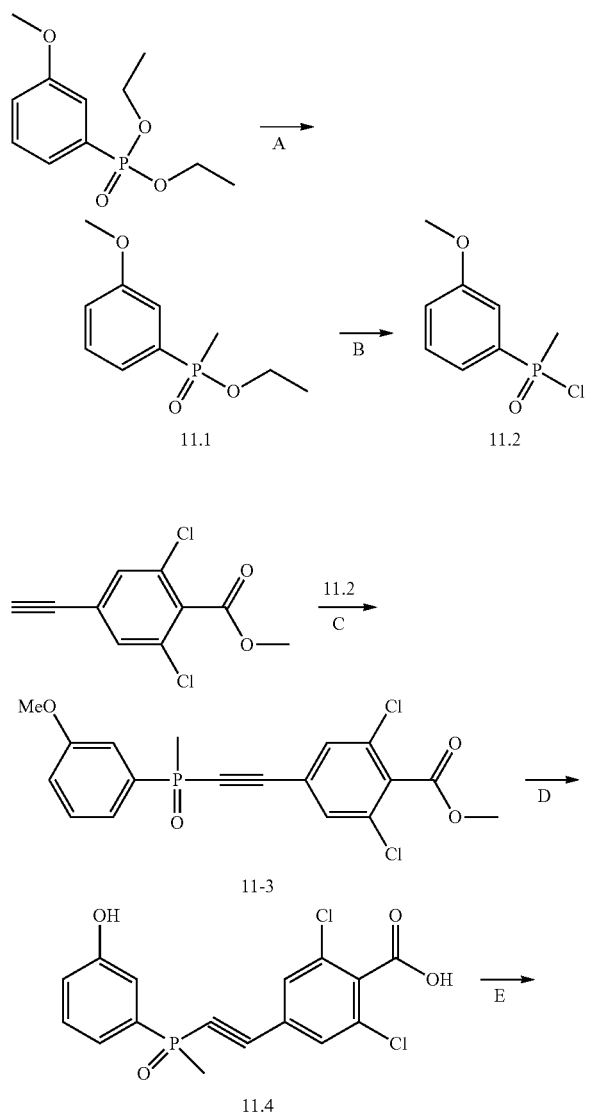

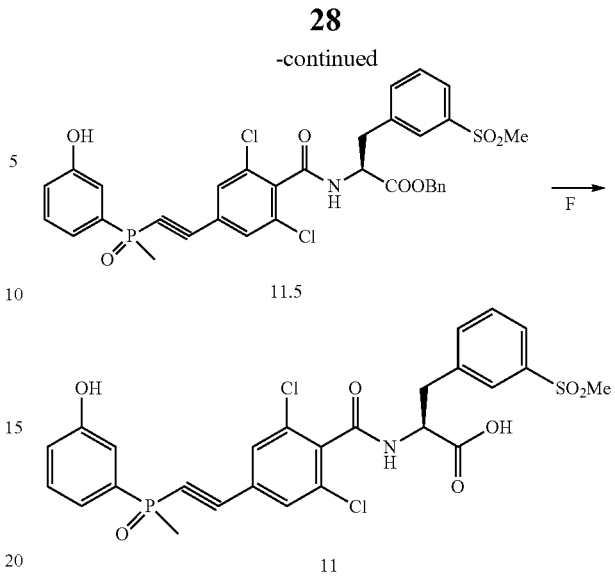

Step A: ethyl (m-methoxyphenyl)methyl phosphate (Compound 11.1)

Thionyl chloride (10 ml) was added to the compound diethyl m-methoxy phosphate (2 g), and the mixture was stirred at 75° C. overnight. After spinning dry, 3 mol/L methyl magnesium chloride (5 ml) was added at 0° C., stirred for 30 minutes, then the reaction was quenched with dilute HCl solution, extracted with EA, dried and spun-dried, purified to give the target product (1.2 g, 68%). LCMS ESI (+) m/z: 214.6 (M+1).

Step B: (m-methoxyphenyl)methylphosphoryl chloride (Compound 11.2)

To Compound 11.1 (150 mg), thionyl chloride was added, the mixture was stirred at 70° C. for 3 hours, and spun-dried to give the target product.

Step C: methyl 2,6-dichloro-4-(((m-methoxyphenyl)(methyl)phosphoryl)ethynyl)benzoate (Compound 11.3)

100 mg of methyl 2,6-dichloro-4-ethynylbenzoate was dissolved in 1.5 ml of tetrahydrofuran, protected with nitrogen, 0.7 ml of 2 mol/L of isopropyl magnesium chloride was added at 0° C., and stirred for 20 minutes; Compound 11.2 was dissolved in 0.5 ml of tetrahydrofuran and added, the reaction lasted for 20 minutes. The reaction was quenched with 1 mol/L dilute HCl solution and extracted three times with 30 mL of ethyl acetate. The organic phases were combined, spun-dried, and purified to give the target product (90 mg, 60%). LCMS ESI (+) m/z: 396.6 (M+1).

Step D: 2,6-dichloro-4-((methyl(m-hydroxyphenyl)phosphoryl)ethynyl)benzoic Acid (Compound 11.4)

Compound 11.3 (90 mg) was dissolved in 2 ml of DCM, protected with nitrogen, and 0.4 ml of boron tribromide (1 mol/L) was added at −40° C., and then stirred at 0° C. for 30 minutes. The reaction was quenched at −40° C., extracted three times with 30 mL of ethyl acetate, dried over anhydrous sodium sulfate and spun-dried. 80 mg of the target product was obtained. ESI (+) m/z: 368.6 (M+1).

Step E: benzyl (2s)-2-(2,6-dichloro-4-((methyl(3-hydroxyphenyl)phosphoryl)ethynyl)benzylamino)-3-(3-(methylsulfonyl)phenyl)propionate (Compound 11.5)

Compound 11.4 was dissolved in DMF and benzyl (2s)-2-amino-3-(3-(methylsulfonyl)phenyl)propanoic acid hydrochloride (2 eq) was added, then followed by DIPEA (10 eq) and HATU (2.5 Eq). After stirring at normal temperature for 4 h, 10 ml of dilute HCl solution was added, extracted three times with EA, and the organic phases were combined, spun-dried. Purification was prepared with the reverse phase, and spun-dried at under reduced pressure at 45° C. to give 70 mg of the target product. LCMS ESI (+) m/z: 683.5 (M+1).

Step F: (2s)-2-(2,6-dichloro-4-((methyl(3-hydroxyphenyl)phosphoryl)ethynyl)benzylamino)-3-(3-(methylsulfonyl)phenyl)propionic Acid (Compound 11)

Compound 11.5 (20 mg) was dissolved in 1 ml of DCM, protected with nitrogen, and 0.5 ml of boron tribromide (1 mol/L) was added at −40° C., and then stirred at 0° C. for 30 minutes. The reaction was quenched by adding water at −40° C., extracted with 30 mL EA, dried over anhydrous sodium sulfate, spun-dried, and purified to give 8 mg of product.

LCMS ESI (+) m/z: 593.5 (M+1).

$^1$H-NMR (400 MHz, DMSO), δ 9.98 (s, 1H), 9.22 (d, J=8.4 Hz, 1H), 7.86 (s, 1H), 7.79 (s, 2H), 7.77 (m, 1H), 7.67 (d, J=8 Hz, 1H), 7.58 (dd, J=8 Hz, J=7.6 Hz, 1H), 7.40 (m, 1H), 7.31 (m, 1H), 7.26 (m, 1H), 7.02 (m, 1H), 4.80 (m, 1H), 3.32 (m, 1H), 3.15 (s, 3H), 3.03 (dd, J=14, J=10.8, 1H), 1.97 (d, J=14.8 Hz, 3H).

Example 12

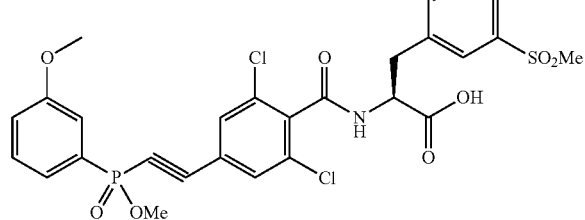

(2s)-2-(2,6-dichloro-4-((methoxy(3-methoxyphenyl)phosphoryl)ethynyl)benzylamino)-3-(3-(methylsulfonyl)phenyl)propionic Acid The specific reaction equation is as follows:

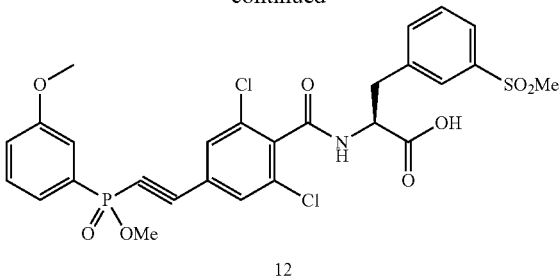

12

Compound 7.1 (10 mg) was dissolved in 1 ml of DCM, protected with nitrogen, and 0.5 ml of boron tribromide (1 mol/L) was added at −40° C., stirred for 30 minutes, then quenched with water, extracted with 30 ml of EA, dried over anhydrous sodium sulfate, spun-dried and purified to give 3 mg of the product.

LCMS ESI (+) m/z: 623.5 (M+1).

1H-NMR (400 MHz, DMSO) δ 9.20 (d, J=7.6 Hz, 1H), 7.87 (s, 2H), 7.86 (s, 1H), 7.77 (d, J=8 Hz, 1H), 7.67 (d, J=7.6 Hz, 1H), 7.55 (m, 2H), 7.44 (m, 1H), 7.30 (m, 2H), 4.80 (m, 1H), 3.84 (d, J=12.4 Hz, 3H), 3.83 (s, 3H), 3.30 (m, 1H), 3.15 (s, 3H), 3.03 (dd, J=14, J=9.4, 1H).

Example 13

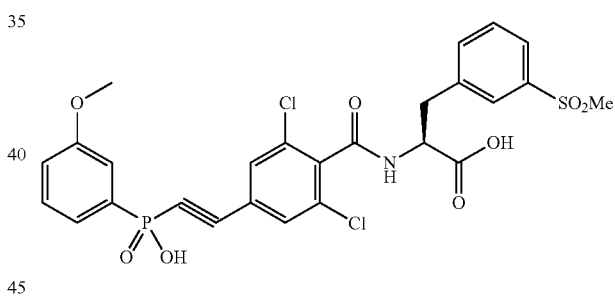

(2s)-2-(2,6-dichloro-4-((hydroxy(3-methoxyphenyl)phosphoryl)ethynyl)benzylamino)-3-(3-(methylsulfonyl)phenyl)propionic Acid The specific reaction equation is as follows:

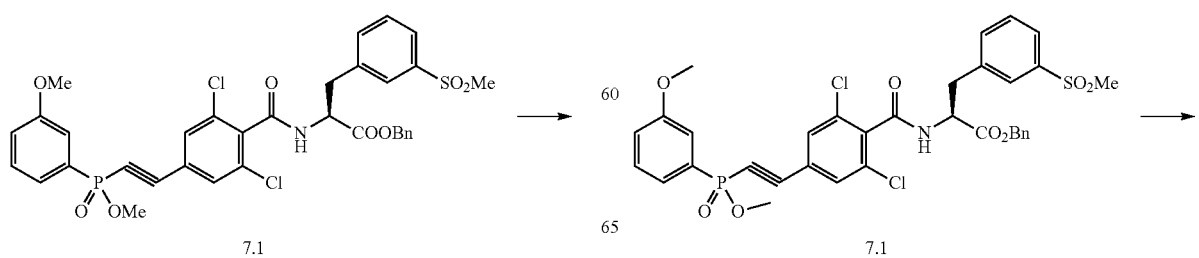

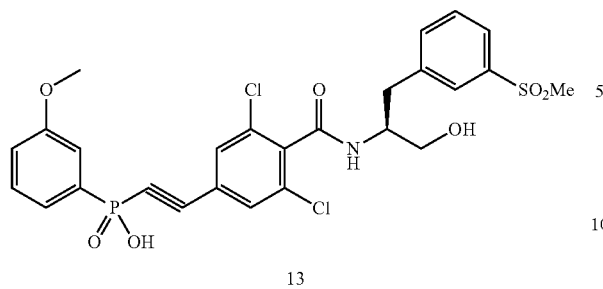

13

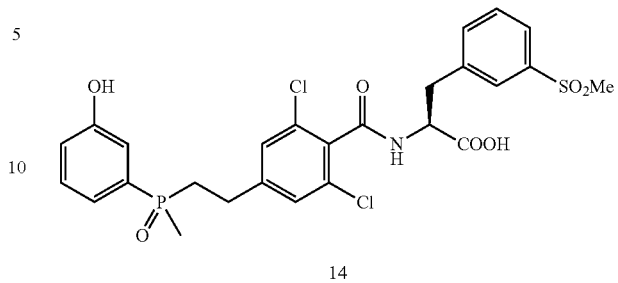

14

Compound 7.1 (10 mg) was dissolved in 1 ml of THF, and lithium hydroxide (20 mg) was taken and dissolved in 0.5 ml of water, stirred at room temperature for 5 minutes. PH=1 was adjusted with concentrated hydrochloric acid, spun-dried, and purified to give 4 mg of product.

LCMS ESI (+) m/z: 609.6 (M+1).

$^1$H-NMR (400 MHz, DMSO) δ 9.20 (d, J=8.4 Hz, 1H), 7.85 (s, 1H), 7.77 (d, J=8 Hz, 1H), 7.66 (d, J=9.4 Hz, 1H), 7.65 (s, 2H), 7.57 (dd, J=8 Hz, J=7.6 Hz, 1H), 7.43 (m, 1H), 7.38 (m, 1H), 7.28 (m, 1H), 7.14 (m, 1H), 4.79 (m, 1H), 3.30 (dd, J=14.8 Hz, J=4.8 Hz, 1H), 3.15 (s, 3H), 3.03 (dd, J=14.4, J=10.8, 1H).

Compound 11.5 (10 mg) was dissolved in methanol (1 ml), and 1 mg of Pd/C (10%) was added, the mixture was hydrogenated at normal pressure for 1 hour, filtered and spun-dried, purified to give 3 mg of the target product. LCMS ESI (+) m/z: 597.6 (M+1).

$^1$H-NMR (400 MHz, DMSO) δ 9.79 (s, 1H), 9.05 (d, J=8 Hz, 1H), 7.86 (s, 1H), 7.77 (d, J=8 Hz, 1H), 7.67 (d, J=8 Hz, 1H), 7.56 (t, J=7.6 Hz, 1H), 7.34 (s, 2H), 7.33 (m, 1H), 7.17 (m, 2H), 6.93 (d, J=7.6 Hz, 1H), 4.75 (m, 1H), 3.29 (dd, J=14 Hz, J=4.4 Hz, 1H), 3.15 (s, 3H), 3.00 (dd, J=14 Hz, 10.4 Hz, 1H), 2.78 (m, 2H), 2.23 (m, 2H), 1.97 (d, J=13.2 Hz, 3H).

Example 14

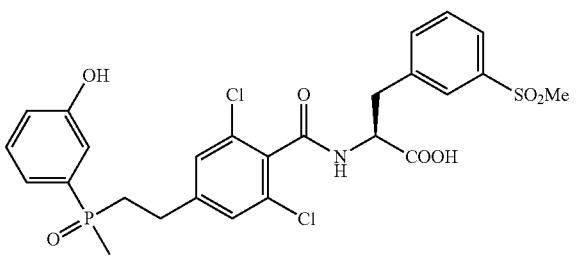 [SMILES: CP(=O)(CCc1cc(Cl)c(C(=O)N[C@@H](Cc2cccc(S(C)(=O)=O)c2)C(=O)O)c(Cl)c1)c1cccc(O)c1]

(2s)-2-(2,6-dichloro-4-(2-(methyl(3-hydroxyphenyl)phosphoryl)ethyl)benzylamino)-3-(3-(methylsulfonyl)phenyl)propionic Acid Example 15

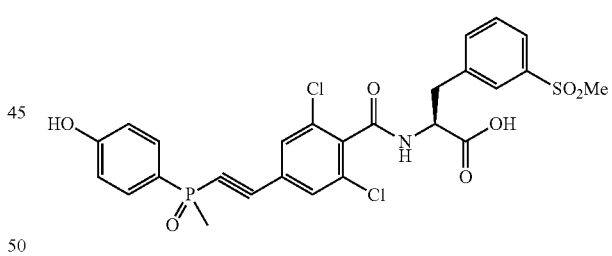

(2s)-2-(2,6-dichloro-4-((methyl(4-hydroxyphenyl)phosphoryl)ethynyl)benzylamino)-3-(3-(methylsulfonyl)phenyl)propionic Acid the same procedure as in Example 11 was carried out except that "diethyl m-methoxy phosphate" was replaced with "diethyl p-methoxy phosphate". LCMS ESI (+) m/z: 594.1 (M+1).

$^1$H-NMR (400 MHz, DMSO) δ 10.39 (s, 1H), 9.21 (d, J=8 Hz, 1H), 7.86 (s, 1H), 7.77 (s, 2H), 7.71-7.66 (m, 3H), 7.57 (t, J=8 Hz, 1H), 6.94 (d, J=7.6 Hz, 2H), 4.79 (m, 1H), 3.29 (dd, J=14 Hz, J=4.4 Hz, 1H), 3.15 (s, 3H), 3.02 (dd, J=14 Hz, 10.4 Hz, 1H), 1.94 (d, J=13.2 Hz, 3H).

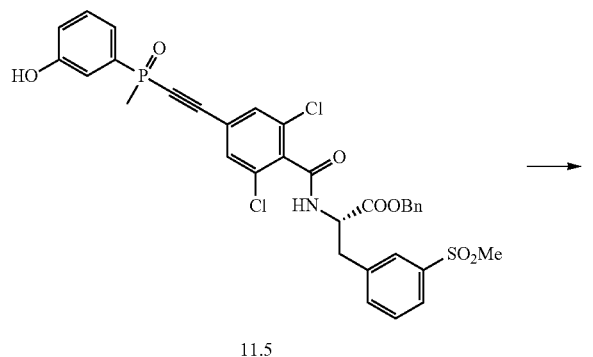

11.5

Example 16

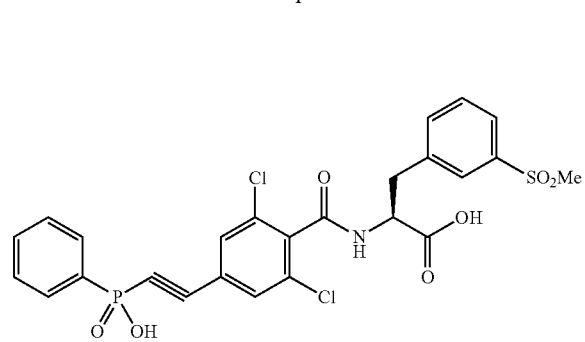

benzyl (2s)-2-(2,6-dichloro-4-((hydroxy(phenyl) phosphoryl)ethynyl)benzamide)-3-(3-(methylsulfonyl)phenyl)propionate the same procedure as in Example 13 was carried out except that "Compound 7.1" was replaced with "Compound 1.4".

LCMS ESI (+) m/z: 580.1 (M+1).

$^1$H-NMR (400 MHz, DMSO) δ9.16 (d, J=8 Hz, 1H), 7.84 (s, 1H), 7.81-7.76 (m, 3H), 7.66 (d, J=8 Hz, 1H), 7.59 (s, 2H), 7.57-7.47 (m, 5H), 4.80 (m, 1H), 3.29 (dd, J=14 Hz, J=4.4 Hz, 1H), 3.14 (s, 3H), 3.02 (dd, J=14 Hz, 10.4 Hz, 1H).

Example 17

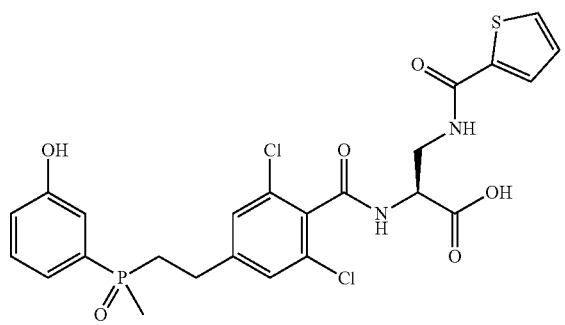 [SMILES: CP(=O)(CCc1cc(Cl)c(C(=O)N[C@@H](CNC(=O)c2cccs2)C(=O)O)c(Cl)c1)c1cccc(O)c1]

(2s)-2-(2,6-dichloro-4-(2-(methyl(3-hydroxyphenyl) phosphoryl)ethyl)benzamido)-3-(2-thenoylamide) propyl Acid The specific reaction equation is as follows:

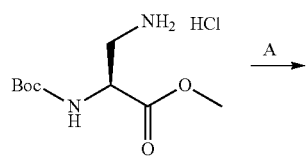

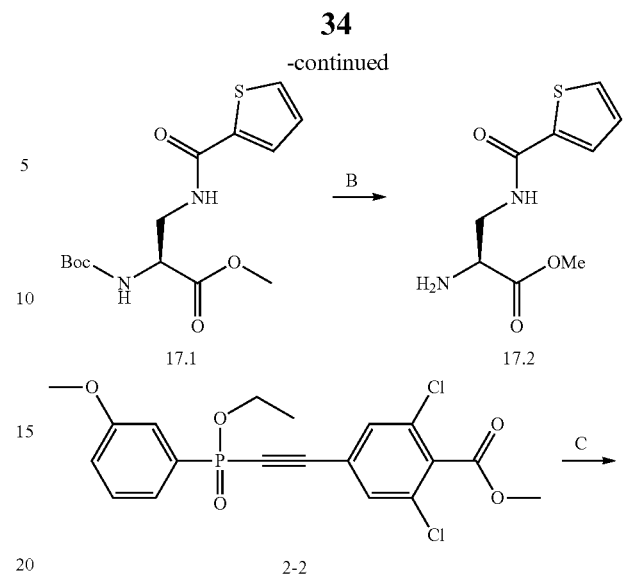

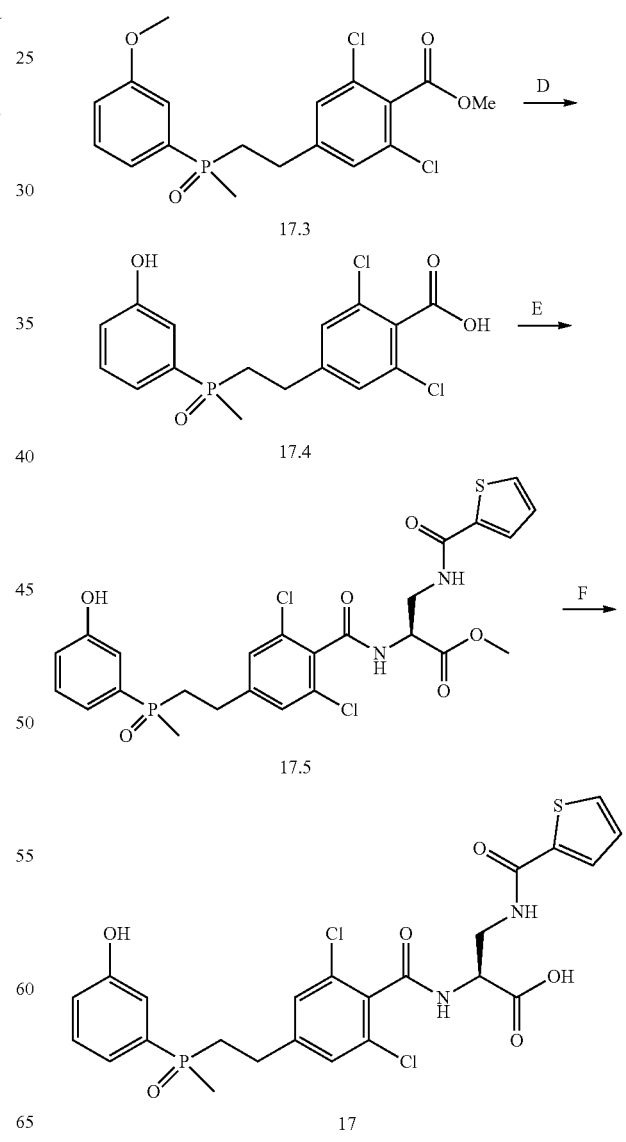

Step A: methyl 3-(2-thenoylamide)-N-[(1,1-dimethylethoxy)carbonyl]-L-alanine (Compound 17.1)

Methyl ((S)-3-amino-2-((1,1-dimethylethoxy)amide)propanoate, HCl salt (2.55 g, 10 mmol) were dissolved in water (30 mL), placed on the ice bath and stirred. THF (20 mL), NaOH (1.0 M aqueous solution, 25 mL) and 2-Thiophenecarbonyl chloride (11 mmol) were added to the resulting solution. After the reaction was stirred for 10 min., EtOAc (100 mL) was added therein, and the aqueous layer was separated and discarded. The organic layer was rinsed with water (25 mL) and saturated NaCl solution, and then dried over anhydrous MgSO4, filtered, spun-dried to give the pure Compound 17.1 (3.3 g, 100%). LCMS ESI (+) m/z: 329 (M+1).

Step B: methyl (S)-2-amino-3-(2-thenoylamide) propionic Acid (Compound 17.2)

Compound 17.1 (1.0 g) was dissolved in DCM (20 mL), HCl-dioxane solution (4.0 M, 5 mL) was added, stirred for 2 h, spun-dried, and the obtained product (hydrochloride) was directly used for the next reaction. LCMS ESI (+) m/z: 229 (M+1).

Step C: methyl 2,6-dichloro-4-(((m-methoxyphenyl)(ethoxy)phosphoryl)ethyl)benzoate (Compound 17.3)

Compound 2.2 (2.0 g) was dissolved in methanol (20 ml), and 100 mg of Pd/C (5%) was added, hydrogenated under normal pressure for 2 hours, filtered and spun-dried to give 2.0 g of the target product.
LCMS ESI (+) m/z: 401.1 (M+1).

Step D: methyl 2,6-dichloro-4-(((m-hydroxyphenyl)(ethoxy)phosphoryl)ethyl)benzoate (Compound 17.4)

Compound 11.3 (500 mg) was dissolved in 10 ml of DCM, protected with nitrogen, and 3.0 ml of boron tribromide (1 mol/L) was added at −40° C., and then stirred at 0° C. for 30 minutes. The reaction was quenched by adding water at −40° C., extracted three times with 30 mL of EA, dried over anhydrous sodium sulfate, and spun-dried, to give 450 mg of the target product. ESI (+) m/z: 373 (M+1).

Step E: methyl (2s)-2-(2,6-dichloro-4-(2-(methyl(3-hydroxyphenyl)phosphoryl)ethyl)benzamido)-3-(2-thenoylamide)propionate (Compound 17.5)

Compound 17.4 (100 mg) was dissolved in DMF (3 mL). Compound 17.4 (2 eq) was then added, followed by DIPEA (10 eq) and HATU (2.5 eq). After stirring at normal temperature for 4 h, 10 ml of dilute HCl solution was added, extracted three times with EA, and the organic phases were combined, spun-dried. Purification was prepared with the reverse phase, and spun-dried under reduced pressure at 45° C. to yield 70 mg of the target product. LCMS ESI (+) m/z: 583 (M+1).

Step F: (2s)-2-(2,6-dichloro-4-(2-(methyl(3-hydroxyphenyl)phosphoryl)ethyl)benzamido)-3-(2-thenoylamide)propionic Acid (Compound 17)

Compound 17.5 (10 mg) was dissolved in 1 ml of THF, and lithium hydroxide (20 mg) was dissolved in 0.5 ml of water, mixed, and stirred at room temperature for 5 minutes. PH=1 was adjusted with concentrated hydrochloric acid, spun-dried, and purified by high pressure liquid phases to give 5.2 mg of product.

LCMS ESI (+) m/z: 569 (M+1).

1H NMR (400 MHz, CD3OD): δ 7.69-7.67 (m, 2H), 7.42-7.37 (m, 1H), 7.26 (s, 2H), 7.23-7.12 (m, 3H), 7.03 (m, J=8.4 Hz, 1H), 4.98 (m, 1H), 3.88-3.84 (m, 2H), 2.93-2.86 (m, 1H), 2.77-2.73 (m, 1H), 2.42-2.32 (m, 2H), 1.78 (m, J=13.2 Hz, 3H).

Example 18

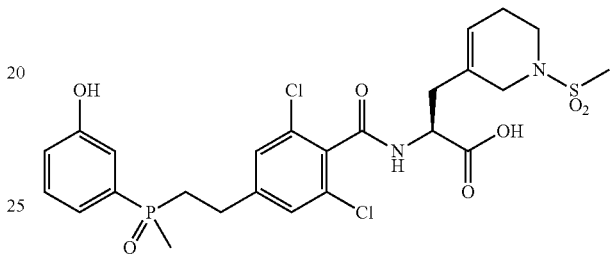

(2s)-2-(2,6-dichloro-4-(2-(methyl(3-hydroxyphenyl)phosphoryl)ethyl)benzamido)-3-(1-(methylsulfonamide)-1,2,5,6-tetrahydropyridin-3-yl)propionic Acid The specific reaction equation is as follows:

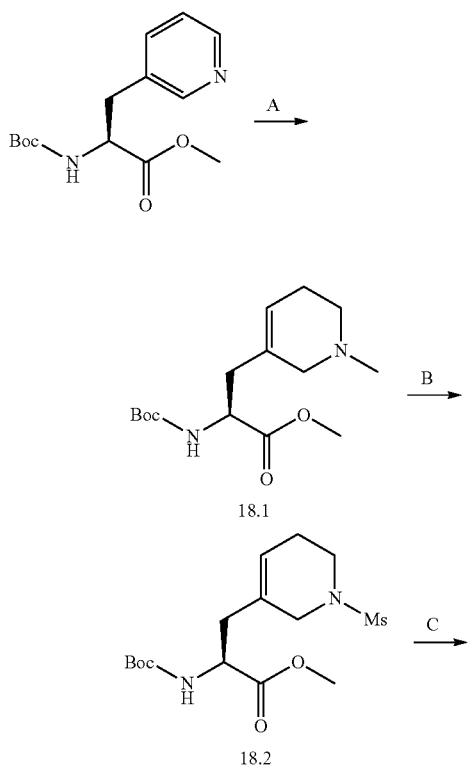

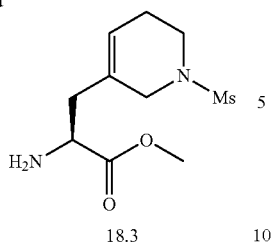

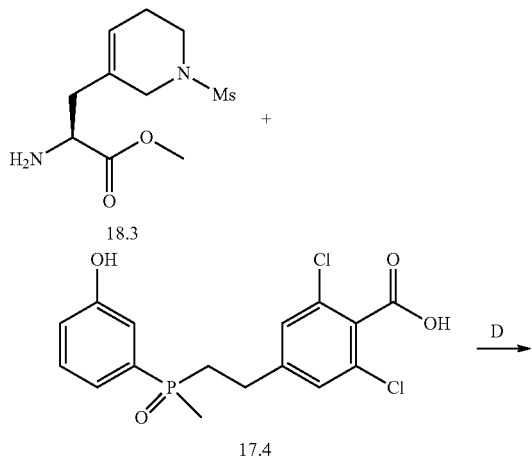

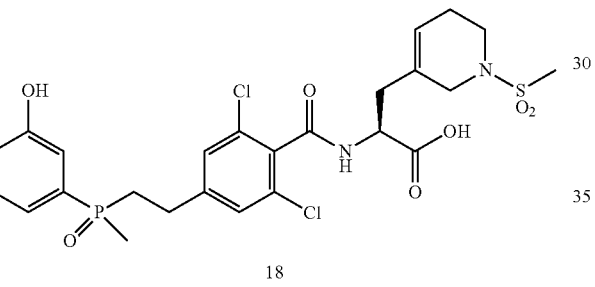

Step A: methyl (S)-2-((tert-butyloxycarbonyl)amino)-3-(1-methyl-1,2,5,6-tetrahydropyridin-3-yl)propionate) (Compound 18.1)

Compound: methyl Boc-3-(3-pyridyl)-L-alaninate (2.8 g, 10 mmol) was dissolved in ethanol (40 mL), and methyl iodide (2 mL) was added to the solution, and the reaction was stirred at 40° C. until the reaction was completed. The reaction temperature was lowered to 0° C., and sodium borohydride (2 g) was added to the solution in portions. After the reaction was stirred for 1 hour, 5 ml of acetone was added to the reaction, and EtOAc (100 mL) was added. The resulting organic solution was washed with saturated NH4Cl solution (20 mL), water (30 mL) and saturated salt solution, dried over anhydrous MgSO4, filtered and spun-dried. The crude product obtained was purified by silica gel column (0-10% MeOH/DCM) to yield Compound 18.1.

Step B: methyl (S)-2-((tertbutyloxycarbonyl)amino)-3-(1-(methylsulfonylamide)-1,2,5,6-tetrahydropyridin-3-yl)propionate (Compound 18.2)

Compound 18.1 (1.5 g, 5 mmol) was dissolved in DCE (20 mL). 1-chloroethyl chloroformate (7.5 mmol) was added, and the reaction was heated to 40° C., kept for 2 hours and spun-dried. Dry methanol (20 mL) was added, and the mixture was refluxed for 1 hour and then spun-dried. DCM (20 ml) and TEA (15 mmol) were added to the obtained intermediate product, and the mixture was cooled to 0° C., and methanesulfonyl chloride (7.5 mmol) was added to the reaction. After stirring for 1 hour, the reaction was diluted with EtOA (80 ml), washed twice with water, dried, filtered and spun-dried to yield Compound 18.2.

Step C: methyl (S)-2-amino-3-(1-(methylsulfonylamide)-1,2,5,6-tetrahydropyridin-3-yl)propionate (Compound 18.3)

Compound 18.2 (100 mg) was dissolved in DCM (5 mL). HCl-dioxane solution (4.0 M, 1 mL) was added, the reaction was stirred for 2 hours and spun-dried, the obtained product (hydrochloride) is ready for direct use in the further reaction. LCMS ESI (+) m/z: 229 (M+1).

Step D: (2s)-2-(2,6-dichloro-4-(2-(methyl(3-hydroxyphenyl)phosphoryl)ethyl)benzamido)-3-(1-(methylsulfonylamide)-1,2,5,6-tetrahydropyridin-3-yl)propionic Acid (Compound 18)

The same procedure for preparing Compound 17 from Compound 17.4 was used to prepare Compound 18 from 17.4, wherein Compound 17.3 was replaced by Compound 18.2.

Example 19

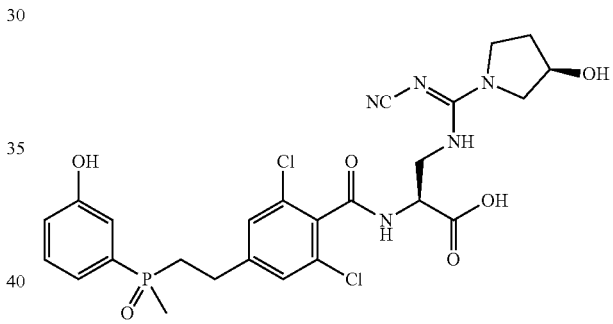

(2s)-3-((R)—N'-cyano-3-hydroxytetrahydropyrrol-1-formamidino)-2-(2,6-dichloro-4-(2-(methyl(3-hydroxyphenyl)phosphoryl)ethyl)benzamido)propionic Acid The specific reaction equation is as follows:

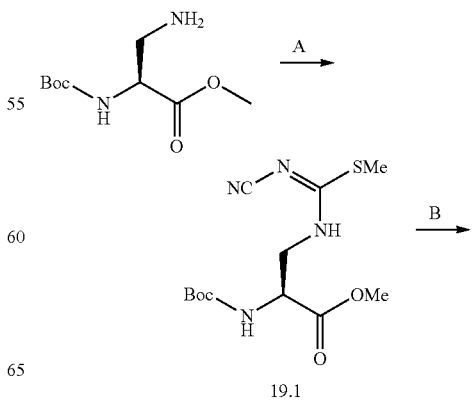

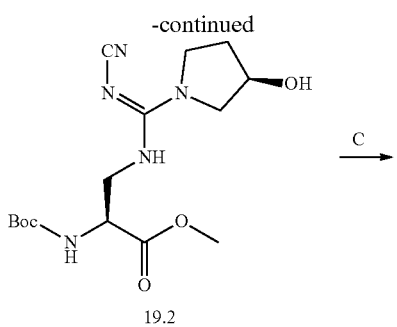

19.2

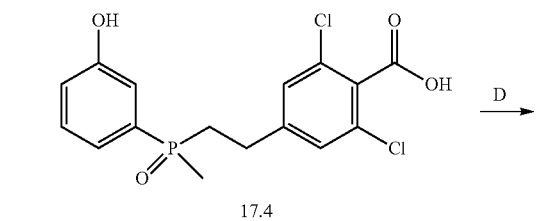

19.3

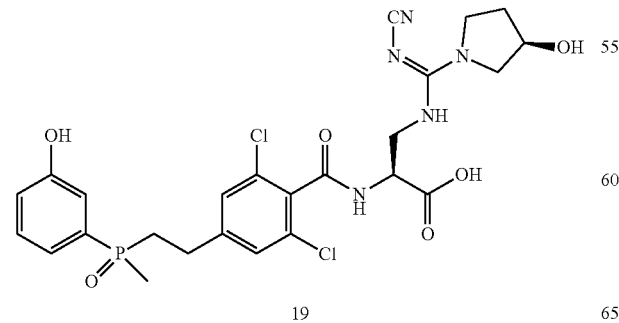

19

Step A: methyl 1-cyano-9,9-dimethyl-2-(methyl-thio)-7-carbonyl-8-oxy-1,3,6-triazadecane-1-ene-5-carboxylate (Compound 19.1)

methyl 3-amino-N-tert-butoxycarbonyl-L-alaninate, HCl salt (2.55 g, 10 mmol) were dissolved in ethanol (30 mL), and dimethyl N-cyanoimino-S,S-dithiocarbonate (10 mmol) and DIPEA (3 mL) were added. The reaction was stirred for 6 hours, and EtOAc (100 mL) was added thereto. The mixture was washed with water (25 mL) and saturated NaCl solution, then dried over anhydrous $MgSO_4$, filtered, and spun-dried to yield the pure Compound 18.1, which is ready for direct use in the further reaction.

Step B: methyl 1-cyano-2-((R)-3-hydroxytetrahydropyrrol-1-yl)-9,9-dimethyl-7-carbonyl-8-oxy-1,3,6-triazadodecane-1-ene-5-carboxylate The obtained Compound 19.1 was dissolved in acetonitrile (20 ml), and (R)-pyrrolidin-3-ol (20 mmol) and silver nitrate (20 mmol) were added. The reaction was refluxed for 8 hours, filtered over silica gel and spun-dried. The crude product was separated on a silica gel column, and separated with 100/5/1 DCM/MeOH/EtOAc to yield the product.

Step C: (2s)-2-amino-3-((R)—N'-cyano-3-hydroxytetrahydropyrrol-1-formamidino)benzamido)propanoic Acid (Compound 19.3)

Compound 19.2 (100 mg) was dissolved in DCM (5 mL), HCl-dioxane solution (4.0 M, 1 mL) was added, and the reaction was stirred for 2 hours, and spun-dried. The obtained product (hydrochloride) is ready for direct use in the further reaction.

Step D: (2s)-3-((R)—N'-cyano-3-hydroxytetrahydropyrrol-1-formamidino)-2-(2,6-dichloro-4-(2-(methyl(3-hydroxyphenyl)phosphoryl)ethyl)benzamido)propionic Acid (Compound 19)

The same procedure for preparing Compound 17 from Compound 17.4 was used to prepare Compound 19 from 17.4, wherein Compound 17.3 was replaced by Compound 19.3. LC-MS: m/z 595.7 (M+H)+.

$^1$H NMR (400 MHz, CD3OD): δ 7.40-7.35 (m, 1H), 7.28-7.27 (m, 2H), 7.21-7.12 (m, 2H), 7.05-7.02 (m, 1H), 4.80-4.86 (m, 1H), 4.60-4.29 (m, 4H), 3.45-3.41 (m, 1H), 3.27-3.24 (m, 1H), 3.15-2.71 (m, 3H), 2.44-2.32 (m, 2H), 2.05-1.74 (m, 5H).

Example 20

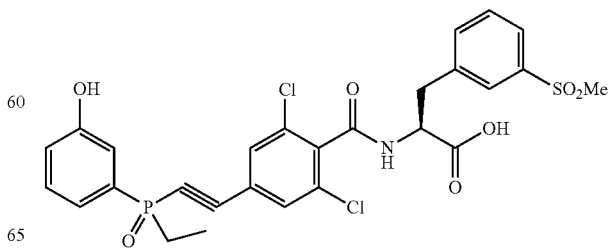

(2s)-2-(2,6-dichloro-4-(ethyl(3-hydroxyphenyl)phosphoryl)ethynyl)benzamido)-3-(3-(methylsulfonylamide)phenyl)propionic Acid The specific reaction equation is as follows:

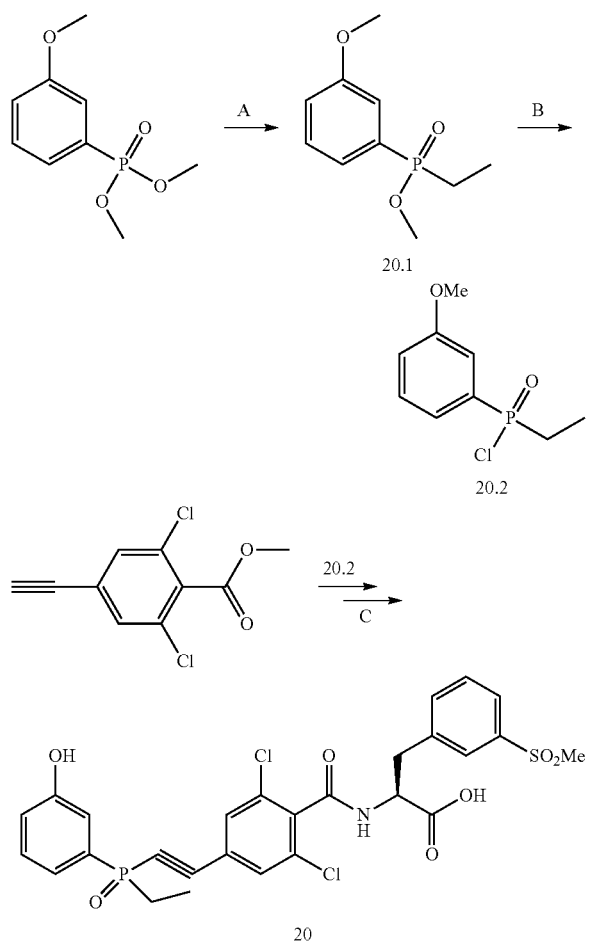

Step A: methyl ethyl(3-methoxyphenyl)phosphate (Compound 20.1)

dimethyl (3-methoxyphenyl)phosphate (2.16 g, 10 mmol) was dissolved in anhydrous THF (30 mL). The solution was cooled to −78° C., and EtMgBr (1.0 M, 10.5 ml) was added. The reaction was gradually warmed to room temperature (temperature rising process lasted for about 2 hours), the reaction was quenched with saturated aqueous NH4Cl solution, and EtOAc (100 mL) was added. The reaction was washed with water, dried over anhydrous MgSO4, filtered and spun-dried. The crude product was isolated on a silica gel column to give the target product.

Step B: Ethyl(3-methoxyphenyl)phosphoryl chloride (Compound 20.2)

Compound 20.1 was dissolved in DCE (10 mL), oxalyl chloride (5 ml) was added, and the resulting solution was refluxed for 5 hours, and the reaction solution was spun-dried to give the target product ready for direct use in the further step.

Step C: (2s)-2-(2,6-dichloro-4-(ethyl(3-hydroxyphenyl)phosphoryl)ethynyl)benzamido)-3-(3-(methylsulfonyl)phenyl)propionic Acid (Compound 20)

The exact same procedure for preparing Compound 2 was carried out for preparing Compound 20, wherein Compound 20.2 was used to replace Compound 2.1.

Example 21

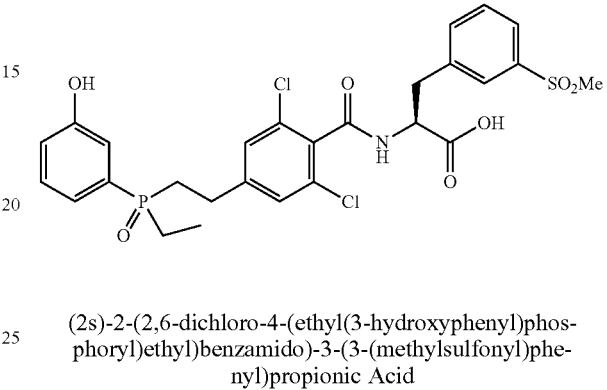

(2s)-2-(2,6-dichloro-4-(ethyl(3-hydroxyphenyl)phosphoryl)ethyl)benzamido)-3-(3-(methylsulfonyl)phenyl)propionic Acid The exact same procedure for preparing Example 3 was carried out for preparing Example 21, wherein Compound 2 was replaced by Compound 20. LCMS ESI (+) m/z: 612.1. (M+1).

$^1$H-NMR (400 MHz, DMSO) δ9.75 (s, 1H), 9.03 (d, J=8 Hz, 1H), 7.85 (s, 1H), 7.78 (d, J=8 Hz, 1H), 7.67 (d, J=8 Hz, 1H), 7.56 (t, J=7.6 Hz, 1H), 7.43 (m, 1H), 7.41 (s, 2H), 7.16-7.12 (m, 2H), 6.93 (d, J=7.6 Hz, 1H), 4.75 (m, 1H), 3.29 (dd, J=14 Hz, J=4.4 Hz, 1H), 3.15 (s, 3H), 3.00 (dd, J=14 Hz, 10.4 Hz, 1H), 2.78-2.50 (m, 2H), 2.26 (m, 2H), 1.86 (m, 2H), 0.93 (dt, J=13.0 Hz, 7.2 Hz, 3H).

Example 22

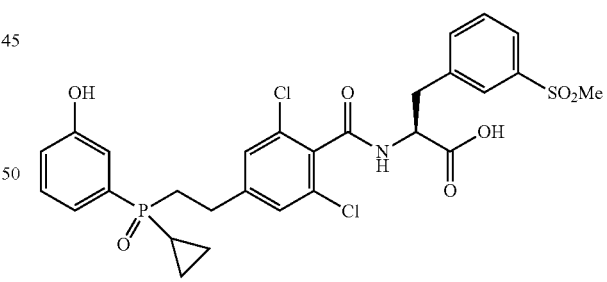

(2s)-2-(2,6-dichloro-4-(cyclopropyl(3-hydroxyphenyl)phosphoryl)ethyl)benzamido)-3-(3-(methylsulfonyl)phenyl)propionic Acid The exact same procedure for preparing Example 21 was used for preparing Example 22, wherein the ethyl Grignard reagent was replaced by the cyclopropyl Grignard reagent. LCMS ESI (+) m/z: 624.1 (M+1).

$^1$H-NMR (400 MHz, DMSO) δ 9.80 (s, 1H), 9.03 (d, J=8 Hz, 1H), 7.85 (s, 1H), 7.78 (d, J=8 Hz, 1H), 7.67 (d, J=8 Hz, 1H), 7.56 (t, J=7.6 Hz, 1H), 7.41 (s, 2H), 7.40 (m, 1H), 7.18-7.23 (m, 2H), 6.93 (d, J=7.6 Hz, 1H), 4.75 (m, 1H), 3.29 (dd, J=14 Hz, J=4.4 Hz, 1H), 3.15 (s, 3H), 3.02 (dd, J=14 Hz, 10.4 Hz, 1H), 2.80 (m, 1H), 2.60 (m, 1H), 2.26 (m, 2H), 1.22 (m, 1H), 0.82 (m, 2H), 0.71 (m, 1H), 0.52 (m, 1H).

Example 23

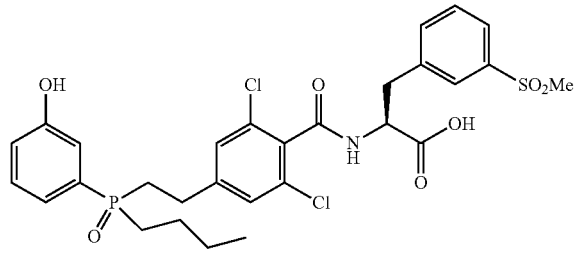 [SMILES: CCCCP(=O)(CCc1cc(Cl)c(C(=O)N[C@@H](Cc2cccc(S(C)(=O)=O)c2)C(=O)O)c(Cl)c1)c1cccc(O)c1]

(2s)-2-(2,6-dichloro-4-(butyl(3-hydroxyphenyl)phosphoryl)ethyl)benzamido)-3-(3-(methylsulfonyl)phenyl)propionic Acid The exact same procedure for preparing Example 21 was used to prepare Example 23, wherein the ethyl Grignard reagent was replaced by the butyl Grignard reagent. LCMS ESI (+) m/z: 630.1 (M+1).

¹H-NMR (400 MHz, DMSO) δ 9.75 (s, 1H), 9.03 (d, J=8 Hz, 1H), 7.85 (s, 1H), 7.78 (d, J=8 Hz, 1H), 7.67 (d, J=8 Hz, 1H), 7.56 (t, J=7.6 Hz, 1H), 7.42 (m, 1H), 7.41 (s, 2H), 7.18-7.12 (m, 2H), 6.93 (d, J=7.6 Hz, 1H), 4.75 (m, 1H), 3.29 (dd, J=14 Hz, J=4.4 Hz, 1H), 3.15 (s, 3H), 3.00 (dd, J=14 Hz, 10.4 Hz, 1H), 2.78 (m, 1H), 2.52 (m, 1H), 2.26 (m, 2H), 1.83 (m, 2H), 1.45 (m, 2H), 1.24-1.20 (m, 3H), 0.80 (t, J=7.2 Hz, 3H).

Example 24

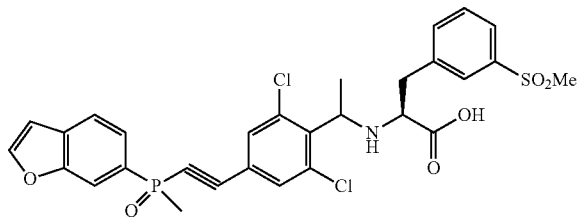 [SMILES: CC(N[C@@H](Cc1cccc(S(C)(=O)=O)c1)C(=O)O)c1c(Cl)cc(C#CP(C)(=O)c2ccc3ccoc3c2)cc1Cl]

(2s)-2-(2,6-dichloro-4-((methyl(benzofuran-6-yl)phosphoryl)ethynyl)benzylamino)-3-(3-(methylsulfonyl)phenyl)propionic acid The specific reaction equation is as follows:

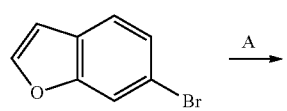

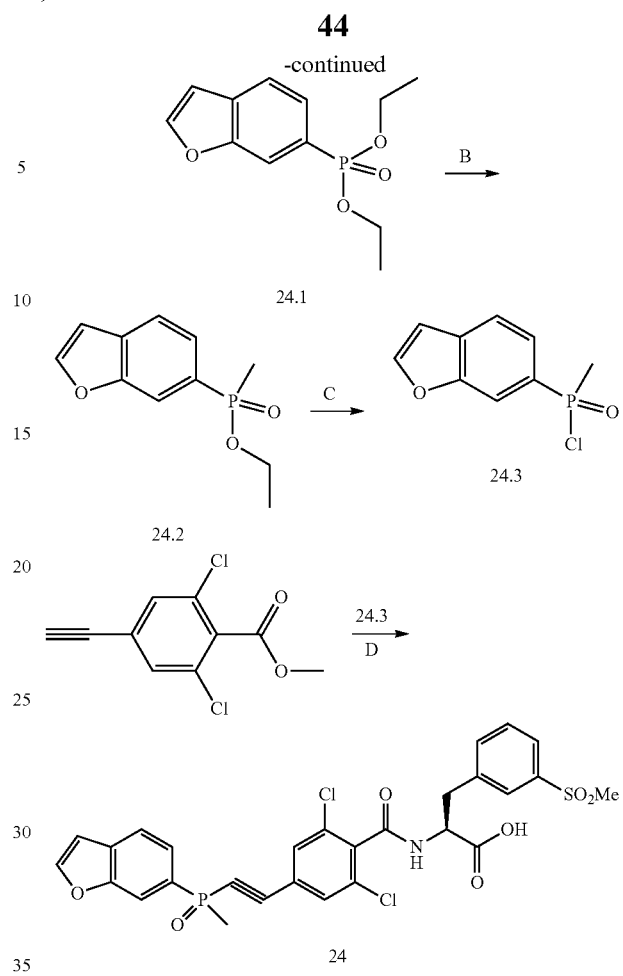

Step A: Diethyl benzofuran-6-yl phosphonate (Compound 24.1)

Compound 6-bromobenzofuran (2.0 g, 10 mmol) was dissolved in diethyl phosphite (6 mL). Pd(OAc)2 (200 mg) and TEA (1 ml) were added. The reaction was heated to 200° C. on a microwave reactor for 30 minutes. EtOAc (80 ml) was added, washed twice with water, dried, filtered and spun-dried. The crude product was separated on a silica gel column, 0-10% MeOH/DCM was mobile phase, and the target product 24.1 was obtained.

Step B: methyl(benzofuran-6-yl) phosphonoacetate (Compound 24.2)

Compound 24.1 (1.27 g) was dissolved in THF (20 mL). The solution was cooled to −78° C., and MeMgBr (1.0 M, 5 ml) was added. The reaction was gradually warmed to room temperature (the temperature rising process lasted for 2 hours), and quenched with saturated aqueous NH4Cl solution. EtOAc (100 mL) was added, and the reaction was washed once with water, dried over anhydrous MgSO4, filtered and spun-dried. The crude product was isolated on a silica gel column to give the target product.

Step C: methyl(benzofuran-6-yl)phosphoryl chloride (Compound 24.3)

Compound 24.2 was dissolved in thionyl chloride (5 ml), and the resulting solution was refluxed for 5 hours, and the reaction solution was spun-dried to give the target product for direct use in the further step.

Step D: (2s)-2-(2,6-dichloro-4-((methyl(benzofuran-6-yl)phosphoryl)ethynyl)benzylamino)-3-(3-(sulfonyl)phenyl)propionic Acid (Compound 24)

The exact same procedure for preparing Compound 2 was used to prepare Compound 24, wherein Compound 24.3 was used to replace Compound 2.1.

LCMS ESI (+) m/z: 619.4 (M+1).
$^1$H-NMR (400 MHz, DMSO) δ9.20 (d, J=8.4 Hz, 1H), 7.85-7.74 (m, 5H), 7.70-7.63 (m, 2H), 7.59-7.44 (m, 2H), 7.40-7.33 (m, 1H), 7.57-7.47 (m, 5H), 4.80 (m, 1H), 3.30 (dd, J=19 Hz, J=4.8 Hz, 1H), 3.14 (d, J=3.2 Hz, 3H), 3.02 (m, 1H), 2.16 (d, J=16 Hz, 3H).

Example 25

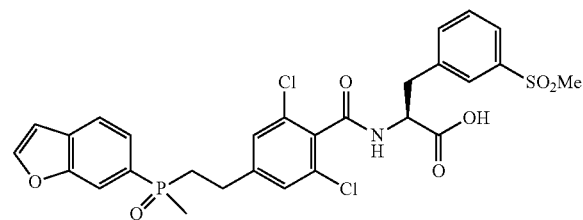 [SMILES: CP(=O)(CCc1cc(Cl)c(C(=O)N[C@@H](Cc2cccc(S(C)(=O)=O)c2)C(=O)O)c(Cl)c1)c1ccc2ccoc2c1]

(2s)-2-(2,6-dichloro-4-((methyl(benzofuran-6-yl)phosphoryl)ethyl)benzylamino)-3-(3-(methylsulfonyl)phenyl)propionic Acid The exact same procedure for preparing Example 3 was used to prepare Example 2, wherein Compound 24 was used to replace Compound 2.

LCMS ESI (+) m/z: 622.1 (M+1).
$^1$H-NMR (400 MHz, DMSO) δ9.04 (d, J=8 Hz, 1H), 8.16 (s, 1H), 8.03 (d, J=11 Hz, 1H) 7.87 (s, 1H), 7.83 (d, J=8 Hz, 1H), 7.78 (d, J=8 Hz, 1H), 7.67 (d, J=8 Hz, 1H), 7.57 (t, J=7.6 Hz, 1H), 7.42 (s, 1H), 7.32 (s, 2H), 7.07 (s, 1H), 4.75 (m, 1H), 3.29 (dd, J=14 Hz, J=4.4 Hz, 1H), 3.16 (s, 3H), 3.02 (dd, J=14 Hz, 10.4 Hz, 1H), 2.88 (m, 1H), 2.68 (m, 1H), 2.34 (m, 2H), 1.71 (d, J=13.2 Hz, 3H).

Example 26

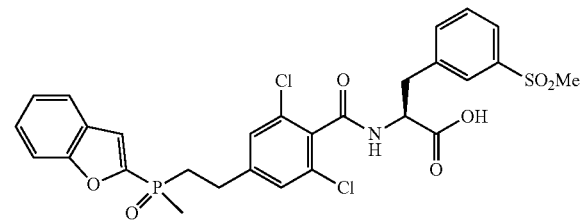 [SMILES: CP(=O)(CCc1cc(Cl)c(C(=O)N[C@@H](Cc2cccc(S(C)(=O)=O)c2)C(=O)O)c(Cl)c1)c1cc2ccccc2o1]

(2s)-2-(2,6-dichloro-4-((methyl(benzofuran-2-yl)phosphoryl)ethyl)benzamido)-3-(3-(methylsulfonyl))phenyl)propionic Acid The exact same procedure for preparing compound 25 was used to prepare compound 26, wherein 2-benzofuran was used to replace 6-benzofuran.

LCMS ESI (+) m/z: 623.6 (M+1). $^1$H-NMR (400 MHz, DMSO) δ9.03 (d, J=8 Hz, 1H), 7.86 (s, 1H), 7.76 (d, J=8 Hz, 2H), 7.67 (t, 2H), 7.60 (s, 1H), 7.56 (t, 1H), 7.45 (t, 1H), 7.38 (s, 2H), 7.34 (t, 1H), 4.75 (m, 1H), 3.29 (dd, J=18.4 Hz, J=4.4 Hz, 1H), 3.01 (dd, J=20.4 Hz, J=10.4 Hz 1H), 2.85 (m 2H), 2.39 (m, 2H), 1.84 (d, J=14 Hz, 3H).

Example 27

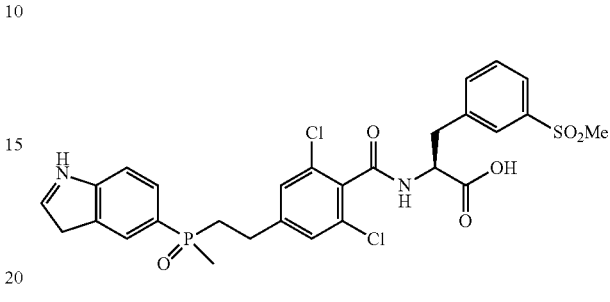

(2s)-2-(2,6-dichloro-4-((methyl(1H-indol-5-yl)phosphoryl)ethyl)benzylamino)-3-(3-(methylsulfonyl)phenyl)propionic Acid The exact same procedure for preparing Compound 25 was used to prepare Compound 26, wherein 1-Ms-5-Br-indole was used to replace 6-benzofuran.

Example 28

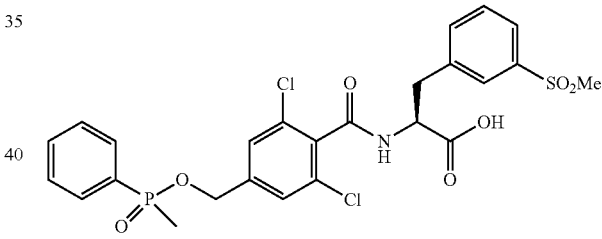

(2S)-2-(2,6-dichloro-4-(((methyl(phenyl)phosphoryl)oxy)methyl)benzamido)-3-(3-(methylsulfonyl)phenyl)propionic Acid The specific reaction equation is as follows:

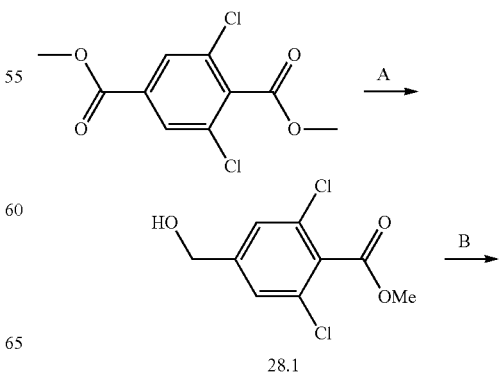

28.1

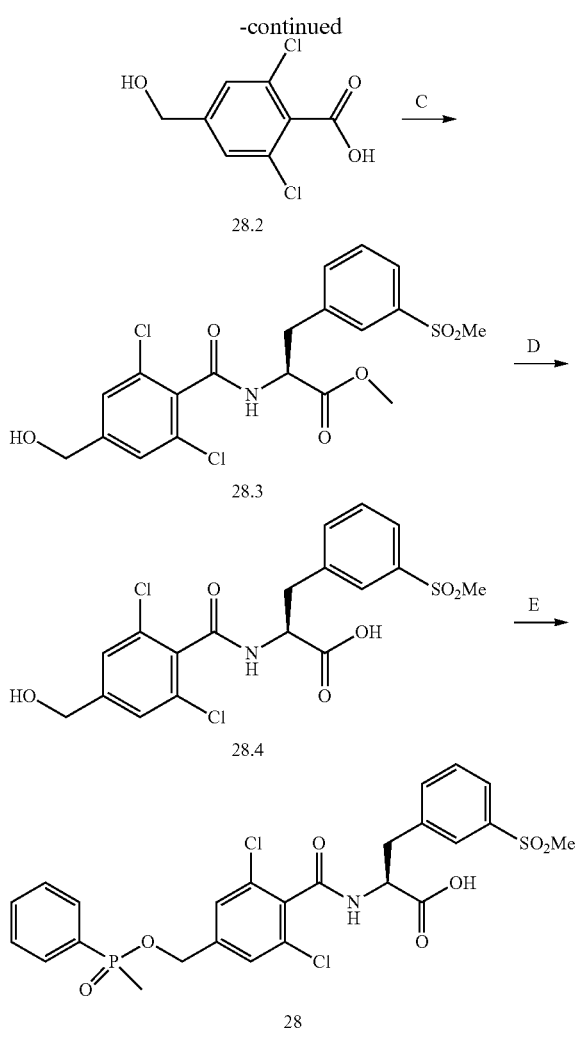

Step A: methyl 2,6-dichloro-(4-hydroxymethyl)benzoate (Compound 28.1)

Dimethyl 2,6-dichloroterephthalate (2.63 g, 10 mmol) was dissolved in THF (50 mL), lithium borohydride (12 mmml) was slowly added, and the reaction was stirred for 1 hour, then acetone (1 ml) and EtOAc (100 ml) were added. The resulting solution was washed twice with water, dried over anhydrous Na2SO4, filtered and spun-dried. The crude product was ready for direct use in the further step.

Step B: 2,6-dichloro-(4-hydroxymethyl)benzoic Acid (Compound 28.2)

Compound 28.1 was dissolved in pyridine (20 ml), lithium iodide (15 mmml) was added, and the reaction was stirred under reflux for 5 hours, then spun-dried, and the crude product was purified using silica gel column, and separated with the mobile phase 95/5/0.5 (v/v/v) DCM/MeOH/AcOH.

Step C: methyl (S)-2-(2,6-dichloro-4-(hydroxymethyl)benzamido)-3-(3-(3-(3-(methylsulfonyl)phenyl)propanoate (Compound 28.3)

Compound 28.2 was dissolved in DMF, and methyl (2s)-2-amino-3-(3-(methylsulfonyl)phenyl)propionate hydrochloride (2 eq), followed by DIPEA (10 eq) and HATU (2.5 Eq). After stirring at normal temperature for 4 hours, 10 ml of dilute hydrochloric acid solution was added, and extracted with EA three times, and the organic phases were combined and spun-dried. Purification was made by reverse phase, spun-dried under reduced pressure at 45° C. to obtain the target product.

Step D: (S)-2-(2,6-dichloro-4-(hydroxymethyl)benzamido)-3-(3-(3-(3-(methylsulfonyl)phenyl)propanoic Acid (Compound 28.4)

Compound 28.3 was dissolved in THF and LiOH (2 eq) was added. The reaction was stirred at room temperature for 4 hours, and the dilute hydrochloric acid solution was added to adjust pH value to about 2-3. It was extracted three times with EA, and the organic phases were combined, spun-dried to give the target product. The product was not purified and ready for direct use in the further step.

Step E: (2S)-2-(2,6-dichloro-4-(((methyl(phenyl)phosphoryl)oxy)methyl)benzamido)-3-(3-(methylsulfonyl)phenyl)propionic Acid (Compound 28)

Compound 28.4 was dissolved in DCM, cooled to 0° C., TEA (10 eq) was added, followed by methylphenylphosphinic chloride (5 eq). The reaction was stirred at room temperature for 5 h, quenched with water (20 eq) and spun-dried. The crude product was purified by reverse phase preparative HPLC to give the target product.

Example 29

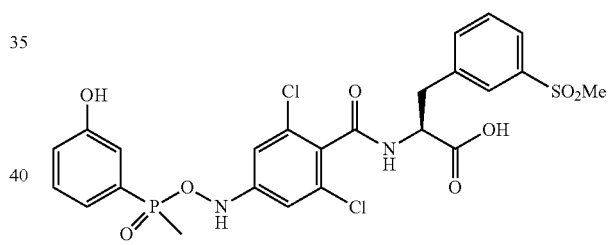

(2S)-2-(2,6-dichloro-4-(((3-hydroxyphenyl))(methyl)phosphoryl)methyl)amino) benzamido)-3-(3-(methylsulfonyl)phenyl)propionic Acid The specific reaction equation is as follows:

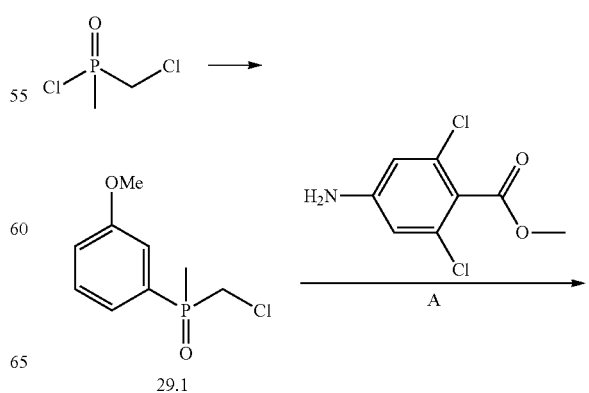

29.1

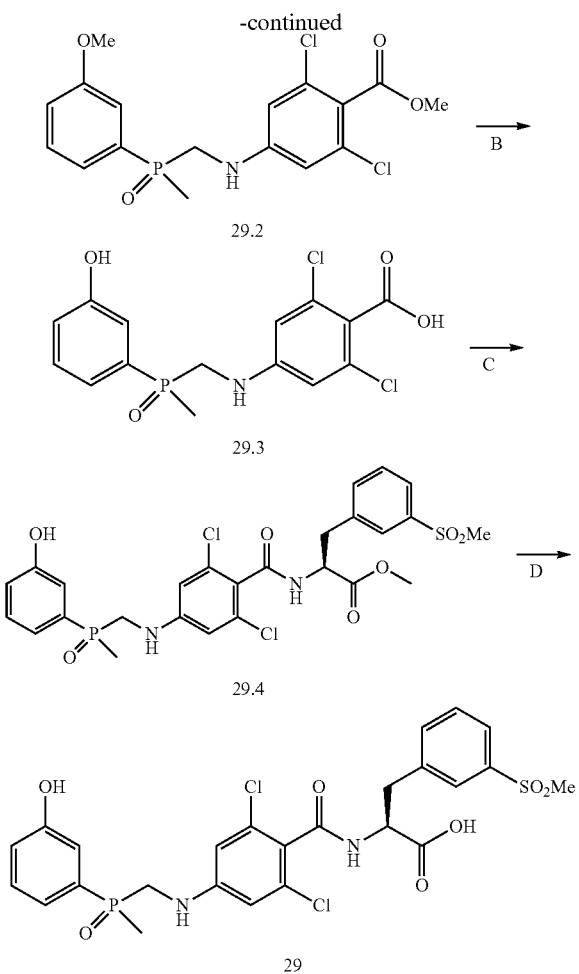

Step A: (chloromethyl)(3-methoxyphenyl)(methyl)phosphorus oxide (Compound 29.1)

Chloromethyl (methyl)phosphinyl chloride (10 mmol) was dissolved in anhydrous THF (30 mL), cooled to −78° C., and (3-methoxy)phenyl lithium (1.01 eq) was added. After the reaction was stirred for 1 hour, it was quenched with dilute hydrochloric acid at −78° C. After the reaction was returned to room temperature, EtOAc (80 ml) was added. The reaction mixture was washed with water, dried, filtered, and spun-dried. The crude product was purified on a silica gel column, and the mobile phase was 0-10% MeOH/DCM (v/v).

Step B: methyl 2,6-dichloro-4-((((3-methoxyphenyl)(methyl)phosphoryl)methyl)amino)benzoate (Compound 29.2)

Compound 29.1 (1 eq), methyl 4-amino-2,6-dichlorobenzoate (1.5 eq) was dissolved in anhydrous DMF (30 mL), sodium iodide (0.1 eq) was added and cooled to 0° C. and sodium hydrogen (3 eq) was added. The reaction was stirred at room temperature until Compound 29.1 disappeared and was quenched with saturated aqueous NH4Cl solution at −78° C. After the reaction was returned to room temperature, EtOAc (80 ml) was added, washed with water three times, dried, filtered and spun-dried. The crude product was purified on a silica gel column, and the mobile phase was 0-10% MeOH/DCM (v/v).

Step C: 2,6-dichloro-4-((((3-methoxyphenyl)(methyl)phosphoryl)methyl)amino)benzoic Acid (Compound 29.3)

Compound 29.2 was dissolved in DCM and 1 mol/L of boron tribromide (10 eq) was added at 0° C.
The reaction was stirred at 25° C. for 30 minutes, then quenched at −40° C., extracted with EA 3 times, the organic phases were combined and spun-dried. The obtained crude product was ready for direct use in the further step.

Step D: methyl (2S)-2-(2,6-dichloro-4-((((3-hydroxyphenyl)(methyl)phosphoryl)methyl)amino)benzamido)-3-(3-(methylsulfonyl)phenyl)propanoate (Compound 29.4)

Compound 11.4 was dissolved in DMF and methyl (2s)-2-amino-3-(3-(methylsulfonyl)phenyl)propionate hydrochloride (2 eq) was added, followed by DIPEA (10 eq) and HATU (2.5 eq). After stirring at normal temperature for 4 hours, 10 ml of dilute hydrochloric acid solution was added, and extracted with EA three times, and the organic phases were combined and spun-dried. Purification was made by reverse phase, and spun-dried under reduced pressure at 45° C. to obtain the target product.

Step E: (2S)-2-(2,6-dichloro-4-(((3-hydroxyphenyl)(methyl)phosphoryl)methyl)amino)benzamido)-3-(3-(methylsulfonyl)phenyl)propionic Acid (Compound 29)

Compound 29.4 was dissolved in THF and LiOH (3 eq) was added. After stirring at normal temperature for 4 hours, the dilute hydrochloric acid solution was added until pH was about 2-3, and extracted with EA 3 times, the organic phases were combined, and spun-dried. The crude product was purified by reverse phase HPLC to yield the pure target product.

Example 30 and Example 31

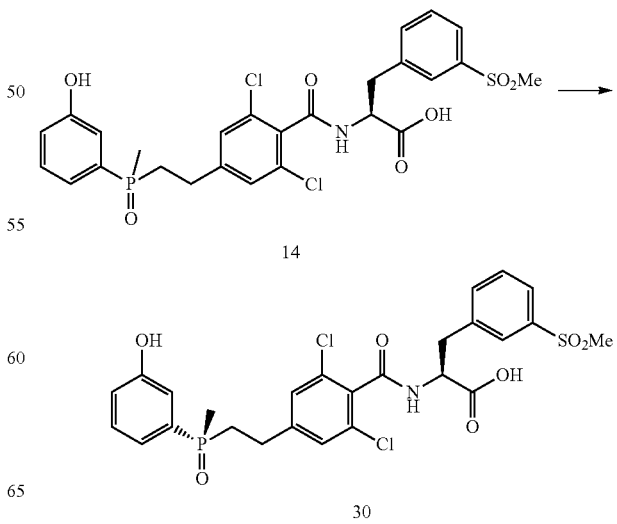

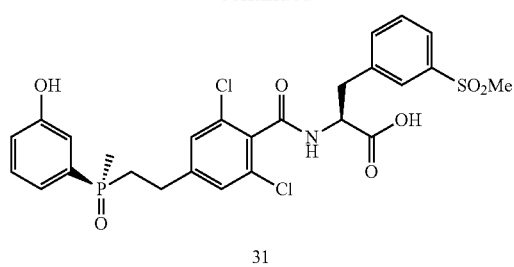

31

Chiral preparative HPLC was used to resolve the compound obtained in Example 14. The chiral column was Chiralcel OZ—H model, the mobile phase was Hexane/EtOH/TFA, and the ratio was 60/40/0.1 (V/V/V). The two isomers were well separated. LCMS and ¹HNMR data were the same as compound 14.

Example 32

(S,E)-2-(4-(2-(3-hydroxyphenyl)phosphonovinyl)-2,6-dichlorobenzamide)-3-(3-(methylsulfonyl)phenyl) propionic Acid The specific reaction equation is as follows:

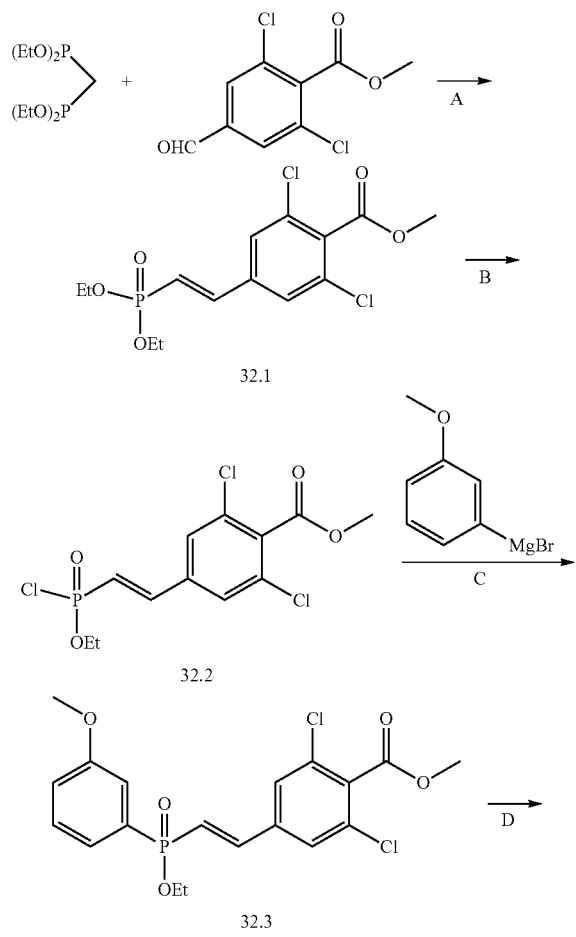

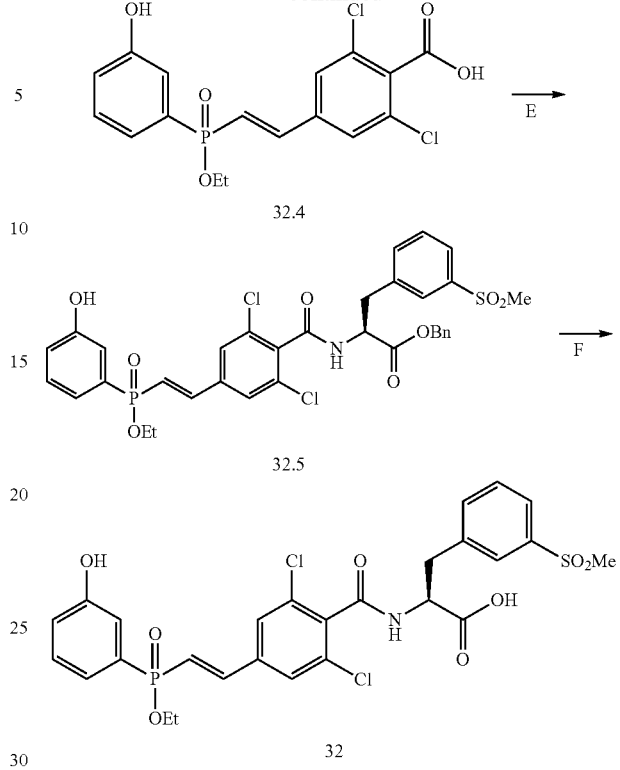

Step A: methyl (E)-2,6-dichloro-4-(2-(diethoxyphosphono)vinyl)benzoate (Compound 32.1)

1 g of methyl 2,6-dichloro-4-aldehyde benzoate and 2.1 g of tetraethyl methylene diphosphate were dissolved in 20 ml of DMF, 2 g of $K_2CO_3$ solid was added, stirred for 2 h, the solvent was removed, and the product was obtained after purification.

Step B: methyl (E)-2,6-dichloro-4-(2-(chloroethoxyphosphonyl)vinyl)benzoate (Compound 32.2)

1 g Compound 32.1 was dissolved in 10 ml of SOCl2, heated to 70° C. for 4 h, and the solvent was removed to yield the product.

Step C: methyl (E)-4-(2-(3-methoxyphenyl)phosphonovinyl)-2,6-dichlorobenzoate (Compound 32.3)

1 g Compound 32.2 was dissolved in 20 ml of THF, cooled to 0° C., and m-methoxyphenylmagnesium bromide was added, stirred at room temperature for 4 hours, THF was removed and the product was obtained after purification.

Step D: (E)-4-(2-(3-hydroxyphenyl)ethoxyphosphonovinyl)-2,6-dichlorobenzoate (Compound 32.4)

200 mg of Compound 32.3 was dissolved in 20 ml CH2Cl2, cooled to 0° C., and BBr3 was added, after 2 h of reaction, water was added, extracted with EA, and spun-dried to give the product.

Step E: benzyl (S,E)-2-(4-(2-(3-hydroxyphenyl)ethoxyphosphonylvinyl)-2,6-dichlorobenzamido)-3-(3-(methylsulfonyl)phenyl)propionate (Compound 32.5)

50 mg of Compound 32.4 and 40 mg of benzyl (2s)-2-amino-3-(3-(methylsulfonyl)phenyl)propionate hydrochloride and 40 mg of DIPEA were dissolved in 5 ml DMF, 60 mg HATU was added, stirred overnight, and DMF was removed, and the product was obtained after purification.

Step F: (S,E)-2-(4-(2-(3-hydroxyphenyl)ethoxyphosphonylvinyl)-2,6-dichlorobenzamido)-3-(3-(methylsulfonyl)phenyl)propionic Acid (Compound 32)

15 mg of Compound 32.5 was dissolved in 1 ml of THF, and 0.2 ml of aqueous LiOH solution was added thereto, and the mixture was stirred for 5 minutes. The solvent was removed and the product was obtained after purification.

LCMS ESI (+) m/z: 629.5 (M+1).

$^1$H-NMR (400 MHz, DMSO) δ9.18 (d, J=8.4 Hz, 1H), 7.85 (s, 1H), 7.82 (s, 2H), 7.78 (d, J=7.6 Hz, 1H), 7.68 (d, J=7.2 Hz, 1H), 7.58 (t, 1H), 7.37 (m, 2H), 7.18 (m, 3H) 7.01 (d, J=6 Hz, 1H), 4.80 (m, 1H), 3.92 (m, 2H), 3.3 (m, 2H), 3.14 (s, 1H), 1.24 (t, J=7.8 Hz, 3H).

Example 33

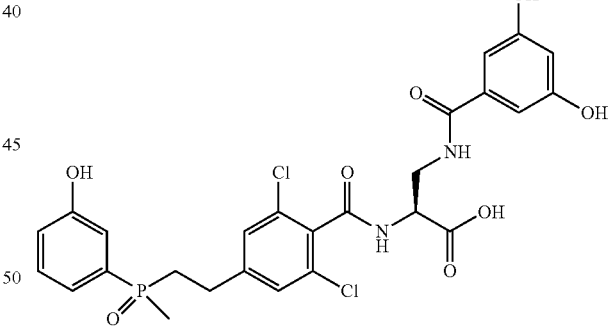

(2s)-2-(2,6-dichloro-4-(2-(hydroxy(4-hydroxyphenyl)phosphoryl)ethyl)benzamido)-3-(3-(methylsulfonyl)phenyl)propionic Acid "Example 16" was converted to Example 33 using the exact same procedure as in Example 14.

LCMS ESI (+) m/z: 597.6 (M+1).

$^1$H-NMR (400 MHz, DMSO) 10.05 (s, 1H), 9.04 (d, J=8 Hz, 1H), 7.86 (s, 1H), 7.77 (d, J=8 Hz, 1H), 7.67 (d, J=8 Hz, 1H), 7.56 (m, 3H), 7.31 (s, 2H), 6.88 (d, J=7.6 Hz, 1H), 4.75 (m, 1H), 3.29 (dd, J=14 Hz, J=4.4 Hz, 1H), 3.15 (s, 3H), 3.02 (dd, J=14 Hz, 10.4 Hz, 1H), 2.78 (m, 1H), 2.60 (m, 1H), 2.18 (m, 2H), 1.59 (d, J=13.2 Hz, 3H).

Example 34

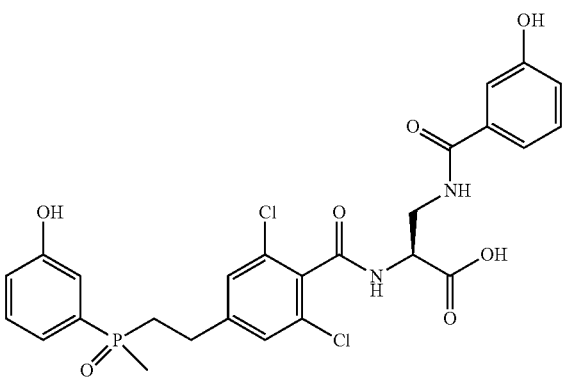 [SMILES: CP(=O)(CCc1cc(Cl)c(C(=O)N[C@@H](CNC(=O)c2cccc(O)c2)C(=O)O)c(Cl)c1)c1cccc(O)c1]

(2s)-2-(2,6-dichloro-4-(2-(methyl(3-hydroxyphenyl)phosphoryl)ethyl)benzamido)-3-(3-hydroxybenzamido)propionic Acid Example 34 was prepared by replacing 2-thiophenecarboxylic acid in Example 17 with 3-hydroxybenzoic acid.

LC-MS: m/z 579.2 (M+H)+

$^1$H NMR (400 MHz, CD3OD): δ 7.40-7.30 (m, 1H), 7.26-7.20 (m, 5H), 7.19-7.16 (m, 1H), 7.30 (d, J=8.8, 1H), 7.00 (d, J=4.8 Hz, 1H), 6.95-6.92 (m, 1H), 4.95 (t, J=4.0 Hz, 1H), 3.84 (d, J=4.4, 2H), 2.92-2.87 (m, 1H), 2.74-2.71 (m, 1H), 2.38-2.30 (m, 2H), 1.75 (d, J=8.4, 3H).

Example 35

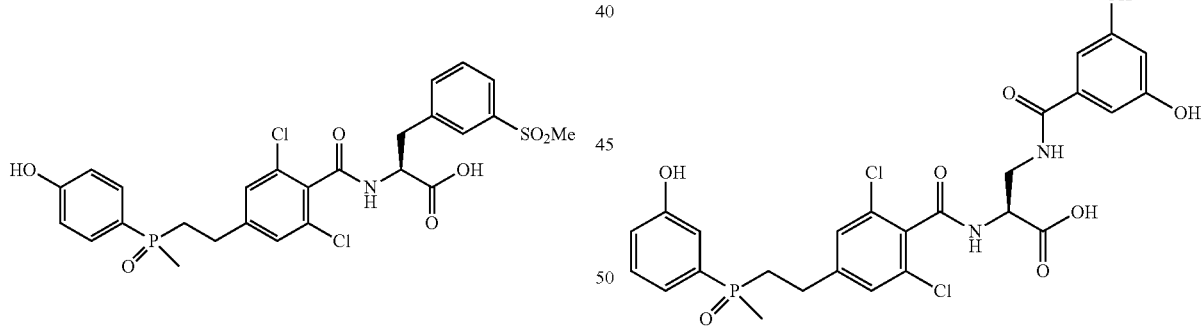

(2s)-2-(2,6-dichloro-4-(2-(methyl(3-hydroxyphenyl)phosphoryl)ethyl)benzamido)-3-(3,5-dihydroxybenzamido)propionic Acid Example 35 was prepared by replacing 2-thiophenecarboxylic acid in Example 17 with 3,5-dihydroxybenzoic acid.

LC-MS: m/z 595.2 (M+H)+

$^1$H NMR (400 MHz, CD$_3$OD): δ 7.41-7.37 (m, 1H), 7.27 (s, 2H), 7.22-7.14 (m, 2H), 7.04-7.01 (m, J=5.2 Hz, 1H), 6.73 (d, J=1.6 Hz, 2H), 6.45 (t, J=1.6 Hz, 1H), 4.97 (m, 1H), 3.80-3.87 (m, 2H), 2.95-2.88 (m, 1H), 2.78-2.71 (m, 1H), 2.43-2.29 (m, 2H) 1.78 (d, J=8.8 Hz, 3H).

Example 36

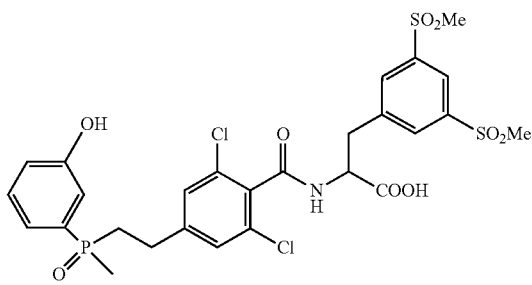 [SMILES: CP(=O)(CCc1cc(Cl)c(C(=O)NC(Cc2cc(S(C)(=O)=O)cc(S(C)(=O)=O)c2)C(=O)O)c(Cl)c1)c1cccc(O)c1]

2-(2,6-dichloro-4-(2-(methyl(3-hydroxyphenyl)phosphoryl)ethyl)benzylamino)-3-(3,5-(dimethylsulfonyl)phenyl)propionic Acid Benzyl (2s)-2-amino-3-(3-(methylsulfonyl)phenyl)propionate hydrochloride in Examples 14 and 11 was replaced by benzyl 2-amino-3-(3,5-(dimethylsulfonyl)phenyl)propionate hydrochloride to give Example 36. LCMS ESI (+) m/z: 583.6 (M+1).

¹H-NMR (400 MHz, DMSO) δ 9.78 (d, J=8 Hz, 1H), 8.25 (d, J=7.6 Hz, 2H), 7.34 (s, 2H), 7.18 (m, 2H), 6.95 (m, 2H), 4.89 (m, 1H), 3.45 (dd, J=15 Hz, J=4.4 Hz, 1H), 3.29 (s, 6H), 3.22 (dd, J=15.5 Hz, J=10.4 Hz, 1H), 2.70 (m, 2H), 2.11 (m, 2H), 1.65 (d, J=13.2, 3H).

Example 37

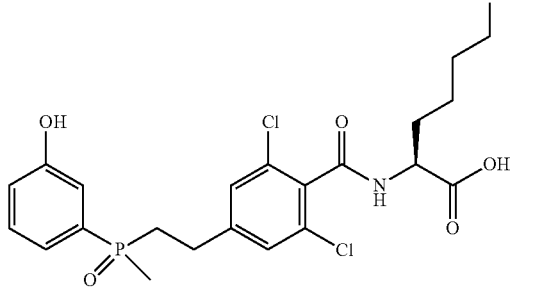

(2s)-2-(2,6-dichloro-4-(2-(methyl(3-hydroxyphenyl)phosphoryl)ethyl)benzylamino)-6-(methylsulfonylamide)hexanoic Acid Benzyl (2s)-2-amino-3-(3-(methylsulfonyl)phenyl)propanoate hydrochloride in Examples 14 and 11 was replaced by methyl (2s)-2-amino-6-(methylsulfonamide)hexanoate hydrochloride to give Example 37. LC-MS: m/z 578.1 (M+H)⁺ ¹H NMR (400 MHz, CD₃OD): δ 7.40 (m, 1H), 7.29 (s, 2H), 7.21-7.17 (s, 2H), 7.22 (m, 1H), 7.17 (m, J=8.8 Hz, 1H), 7.02 (d, J=5.2 Hz, 1H), 4.02 (m, 1H), 3.41 (t, J=4.4 Hz, 2H), 3.96-3.91 (m, 1H), 2.97 (s, 3H), 2.95-2.90 (m, 1H), 2.82-2.72 (m, 1H), 2.47-2.32 (m, 2H), 1.92-1.90 (m, 1H), 1.79 (d, J=8.8, 3H), 1.79 (m, 5H).

Example 38

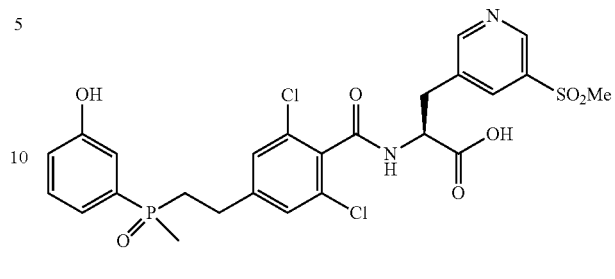

(2s)-2-(2,6-dichloro-4-(2-(methyl(3-hydroxyphenyl)phosphoryl)ethyl)benzylamino)-3-(5-(methylsulfonyl)pyridine-3-yl)propionic Acid Benzyl (2s)-2-amino-3-(3-(methylsulfonyl)phenyl)propionate hydrochloride in Examples 14 and 11 was replaced by (2s)-2-amino-3-(5-(methanesulfonyl)pyridin-3-yl)propionic acid hydrochloride to give Example 38. LCMS ESI (+) m/z: 600.4 (M+1).

¹H-NMR (400 MHz, MeOD) δ 8.96 (s, 1H), 8.83 (s, 1H), 8.39 (s, 1H), 7.38 (m, H), 7.24 (s, 2H), 7.17 (m, 2H), 7.02 (d, J=7.6 Hz, 1H), 5.08 (m, 1H), 3.52 (m, 1H), 3.20 (s, 1H), 2.88 (m, 1H), 2.74 (m, 1H), 2.33 (m, 2H), 1.79 (d, J=13.2 Hz, 3H).

Example 39

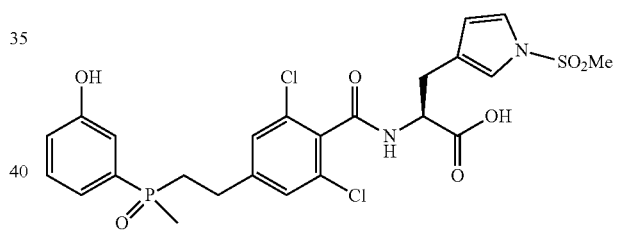

(2s)-2-(2,6-dichloro-4-(2-(methyl(3-hydroxyphenyl)phosphoryl)ethyl)benzylamino)-3-(1-(methylsulfonyl)-1H-pyrrol-3-yl)propionic Acid Benzyl (2s)-2-amino-3-(3-(methylsulfonyl)phenyl)propionate hydrochloride in Examples 14 and 11 was replaced by (2s)-2-amino-3-(1-(methanesulfonyl)-1H-pyrrol-3-yl)propionic acid hydrochloride to give Example 39.

Example 40

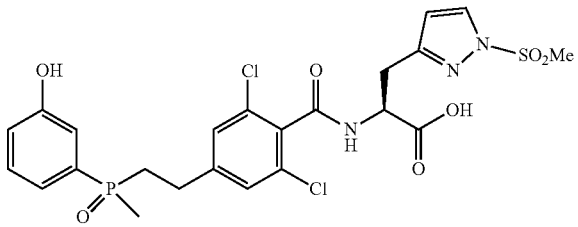 [SMILES: CP(=O)(CCc1cc(Cl)c(C(=O)N[C@@H](Cc2ccn(S(C)(=O)=O)n2)C(=O)O)c(Cl)c1)c1cccc(O)c1]

(2s)-2-(2,6-dichloro-4-(2-(methyl(3-hydroxyphenyl)phosphoryl)ethyl)benzylamino)-3-(1-(methylsulfonyl)-1H-pyrazol-3-yl)propionic Acid Benzyl (2s)-2-amino-3-(3-(methylsulfonyl)phenyl)propionate hydrochloride in Examples 14 and 11 was replaced by (2s)-2-amino-3-(1-(methanesulfonyl)-1H-pyrazol-3-yl)propionic acid hydrochloride to give Example 40.

Example 41

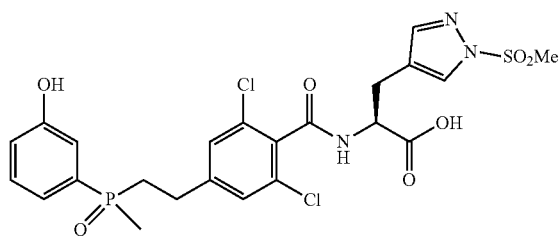 [SMILES: CP(=O)(CCc1cc(Cl)c(C(=O)N[C@@H](Cc2cnn(S(C)(=O)=O)c2)C(=O)O)c(Cl)c1)c1cccc(O)c1]

(2s)-2-(2,6-dichloro-4-(2-(methyl(3-hydroxyphenyl)phosphoryl)ethyl)benzylamino)-3-(1-(methylsulfonyl)-1H-pyrazol-4-yl)propionic Acid Benzyl (2s)-2-amino-3-(3-(methylsulfonyl)phenyl)propionate hydrochloride in Examples 14 and 11 was replaced by (2s)-2-amino-3-(1-(methanesulfonyl)-1H-pyrazol-4-yl)propionic acid hydrochloride to give Example 41.

Example 42

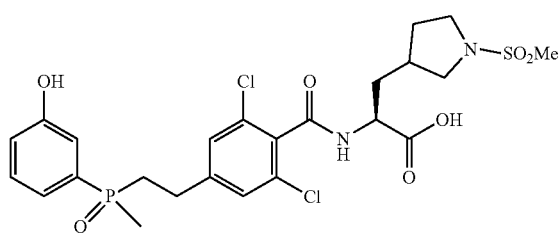 [SMILES: CP(=O)(CCc1cc(Cl)c(C(=O)N[C@@H](CC2CCN(S(C)(=O)=O)C2)C(=O)O)c(Cl)c1)c1cccc(O)c1]

(2s)-2-(2,6-dichloro-4-(2-(methyl(3-hydroxyphenyl)phosphoryl)ethyl)benzylamino)-3-(1-(methylsulfonyl)pyrrolidin-3-yl)propionic Acid Benzyl (2s)-2-amino-3-(3-(methylsulfonyl)phenyl)propionate hydrochloride in Examples 14 and 11 was replaced by (2s)-2-amino-3-(1-(methanesulfonyl)pyrrolidin-3-yl)propionic acid hydrochloride to give Example 42. LC-MS: m/z 591.1 (M+H)$^+$.

$^1$H NMR (400 MHz, CD$_3$OD): δ 7.43-7.37 (m, 1H), 7.30 (s, 2H), 7.25-7.20 (m, 2H), 7.04-7.01 (m, 1H), 4.71-4.63 (m, 1H), 3.68-3.55 (m, 1H), 3.50-3.44 (m, 1H), 3.30-3.28 (m, 1H), 3.05-2.90 (m, 2H), 2.89 (d, J=2.0 Hz, 3H), 2.88-2.75 (m, 1H), 2.52-2.50 (m, 1H), 2.50-2.10 (m, 3H), 2.09-1.82 (m, 2H), 1.79 (d, J=9.2 Hz, 3H), 1.69 (m, 1H).

Example 43

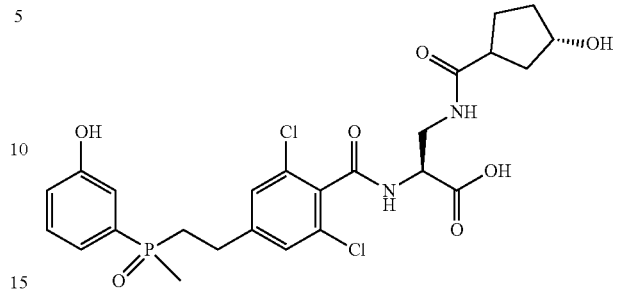

(2s)-2-(2,6-dichloro-4-(2-(methyl(3-hydroxyphenyl)phosphoryl)ethyl)benzamido)-3-((S)-3-hydroxylpyrrolidine-1-carboxamide)propionic Acid Example 43 was prepared by replacing 2-thiophenecarboxylic acid in Example 17 with (s)-3-hydroxypyrrolidine-1-carbonyl chloride.

LC-MS: m/z 595.7 (M+H)+.

$^1$HNMR (400 MHz, CD3OD): δ 7.39-7.35 (m, 1H), 7.26 (s, 2H), 7.19-7.12 (m, 2H), 7.01 (d, J=8.4, 1H), 4.78-4.74 (m, 1H), 4.36-4.40 (m, 1H), 3.66-3.64 (m, 2H), 3.45-3.41 (m, 3H), 3.27-3.25 (m, 1H), 2.95-2.85 (m, 1H), 2.79-2.69 (m, 1H), 2.39-2.27 (m, 2H), 2.05-1.92 (m, 2H), 1.77 (d, J=12.4, 1H).

Example 44

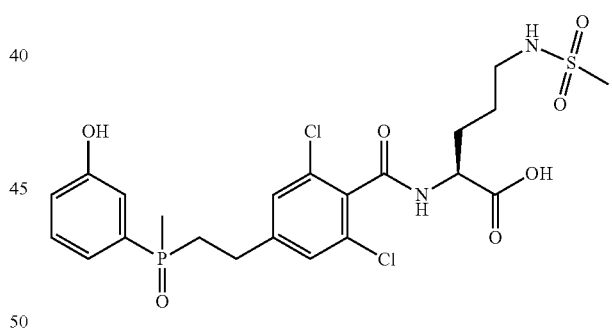

(2s)-2-(2,6-dichloro-4-(2-(methyl(3-hydroxyphenyl)phosphoryl)ethyl)benzylamino)-5(methylsulfonamide)pentanoic Acid Benzyl (2s)-2-amino-3-(3-(methylsulfonyl)phenyl)propionate hydrochloride in Examples 14 and 11 was replaced by methyl (2s)-2-amino-5 (methylsulfonamide)valerate hydrochloride to give Example 44.

LC-MS: m/z 565.1 (M+H)$^+$.

$^1$H NMR (400 MHz, CD$_3$OD): δ 7.39-7.36 (m, 1H), 7.27 (s, 2H), 7.21-7.17 (m, 1H), 7.14 (d, J=8.4 Hz, 1H) 7.00 (d, J=5.6 Hz, 1H), 4.05 (m, 1H), 3.42-3.40 (m, 2H), 2.95 (s, 3H), 2.91-2.87 (m, 1H), 2.74-2.72 (m, 1H), 2.39-2.28 (m, 2H), 2.04-2.02 (m, 1H), 1.81-1.74 (m, 6H).

Example 45

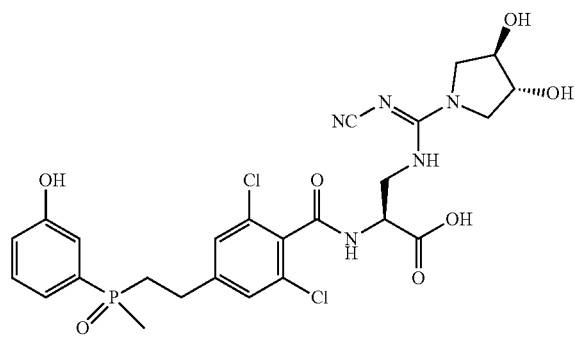 [SMILES: CP(=O)(CCc1cc(Cl)c(C(=O)N[C@@H](CN/C(=N\C#N)N2C[C@@H](O)[C@H](O)C2)C(=O)O)c(Cl)c1)c1cccc(O)c1]

(2s)-3-((trans)-N'-cyano-3,4-dihydroxypyrrolidine-1-formamidino)-2-(2,6-dichloro-4-(2-(methyl(3-hydroxyphenyl)phosphoryl)ethyl)benzamido)propionic Acid Example 45 was prepared by replacing (R)-3-pyrrolidinol in Example 19 with (trans)-3,4-pyrrolidine diol.

LC-MS: m/z 611.7 (M+H)$^+$.

$^1$H NMR (400 MHz, CD$_3$OD): δ 7.41-7.39 (m, 1H), 7.30-7.28 (m, 2H), 7.24-7.20 (m, 2H), 7.05-7.03 (m, 1H), 5.11 (dd, J=10.4, 4.4, 1H), 4.11-4.18 (m, 1H), 4.04-4.01 (m, 1H), 3.79-3.72 (m, 1H), 3.51-3.56 (m, 1H), 3.26-3.25 (m, 1H), 3.23-3.22 (m, 1H), 3.17-3.13 (m, 1H), 3.07-3.03 (m, 1H), 3.00-2.96 (m, 1H), 2.94-2.86 (m, 1H), 2.77-2.66 (m, 1H), 2.45-2.33 (m, 2H), 1.79-1.75 (m, 3H).

Example 46

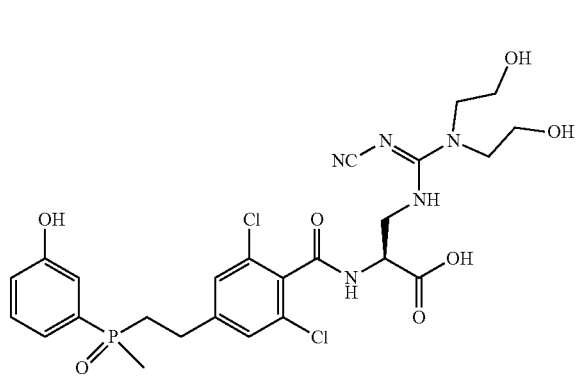 [SMILES: CP(=O)(CCc1cc(Cl)c(C(=O)N[C@@H](CN/C(=N\C#N)N(CCO)CCO)C(=O)O)c(Cl)c1)c1cccc(O)c1]

(2s)-3-(2-cyano-3,3-bis(2-hydroxyethyl)guanidino)-2-(2,6-dichloro-4-(2-(methyl(3-hydroxyphenyl)phosphoryl)ethyl)benzamido)propionic Acid Example 46 was prepared by replacing (R)-3-pyrrolidinol in Example 19 with diethanolamine.

LC-MS: m/z 595.6 (M-OH)$^+$.

$^1$H NMR (400 MHz, CD$_3$OD): δ 7.38-7.37 (m, 1H), 7.30-7.27 (m, 2H), 7.21-7.17 (m, 2H), 7.01-6.99 (m, 1H), 5.71 (dd, J=10.0, 4.0, 1H), 4.07-4.04 (m, 1H), 3.96-3.91 (m, 1H), 3.79-3.43 (m, 8H), 2.99-2.90 (m, 1H), 2.82-2.72 (m, 1H), 2.47-2.36 (m, 2H), 1.75 (d, J=12.8, 3H).

Example 47

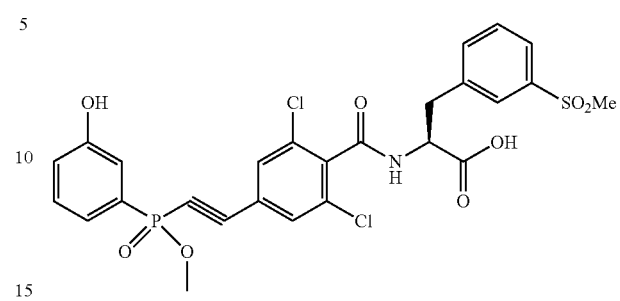

(2s)-2-(2,6-dichloro-4-((methoxy(2-hydroxyphenyl)phosphoryl)ethynyl)benzylamino)-3-(3-(methylsulfonyl)phenyl)propionic Acid The specific reaction equation is as follows:

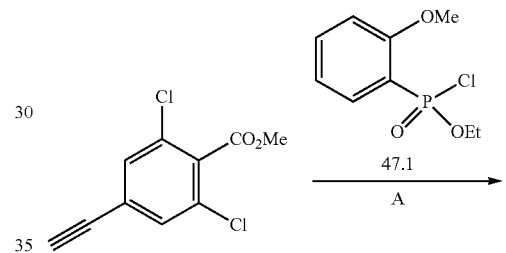

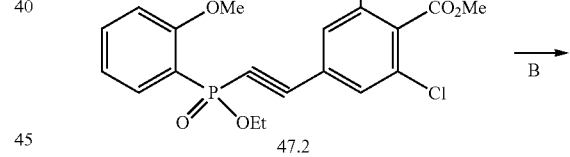

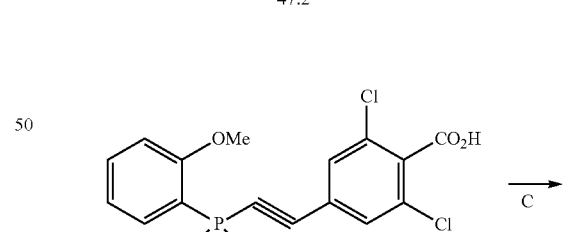

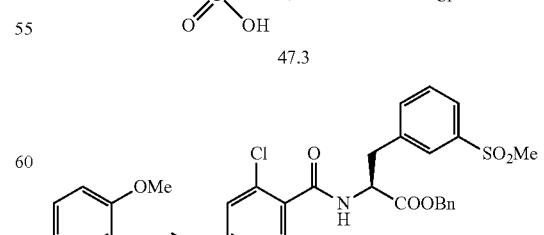

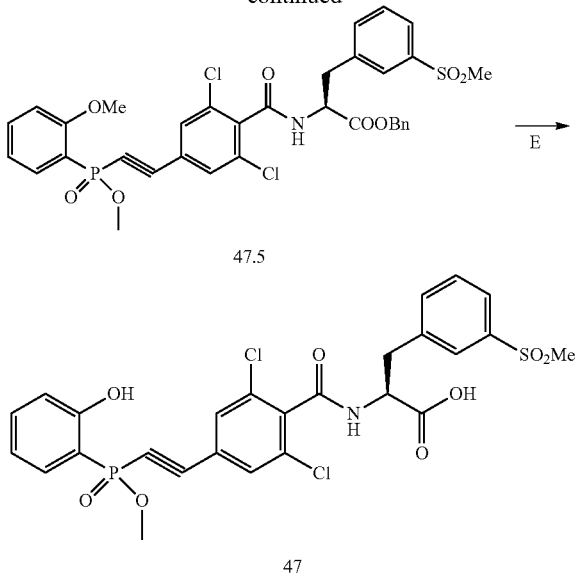

47.5

47

Step A: methyl 2,6-dichloro-4-(((o-methoxyphenyl)(ethoxy)phosphoryl)ethynyl)benzoate (Compound 47.2)

100 mg of methyl 2,6-dichloro-4-ethynylbenzoate was dissolved in 1.5 ml of tetrahydrofuran, protected with nitrogen, and 0.7 ml of 2 mol/L of isopropylmagnesium chloride was added at 0° C., and stirred for 20 minutes; Compound 47.1 was dissolved in 0.5 ml of tetrahydrofuran and reacted for 20 minutes. The reaction was quenched with 1 mol/L dilute hydrochloric acid solution, and extracted three times with 30 mL ethyl acetate, the organic phases were combined, spun-dried, and purified to yield the product (100 mg, 60%). LCMS ESI (+) m/z: 426.6 (M+1).

Step B: 2,6-dichloro-4-((hydroxy(o-methoxyphenyl)phosphoryl)ethynyl)benzoic Acid (Compound 47.3)

Compound 47.3 (100 mg) and lithium iodide (100 mg) were dissolved in 2 ml of pyridine, protected with nitrogen, stirred at 120° C. for 3 hours, cooled and spun-dried, and 10 ml of 1 mol/L dilute hydrochloric acid solution was added. It was extracted three times with 30 mL of ethyl acetate, and the organic phases were combined, and spun-dried without purification.
LCMS ESI (+) m/z: 384.6 (M+1).

Step C: benzyl (2s)-2-(2,6-dichloro-4-((hydroxy(o-methoxyphenyl)phosphoryl)ethynyl)benzamido)-3-(3-(methylsulfonyl)phenyl)propionate (Compound 47.4)

Compound 47.3 was dissolved in DMF and benzyl (2s)-2-amino-3-(3-(methylsulfonyl)phenyl)propionate hydrochloride (2 eq) was added, then followed by DIPEA (10 eq) and HATU (2.5 eq). After stirring at normal temperature for 4 h, 10 ml of dilute hydrochloric acid solution was added, and extracted with EA three times, and the organic phases were combined and spun-dried. Purification was made by reverse phase, and spun-dried at 45° C. under reduced pressure to give the target product, 85 mg.
LCMS ESI (+) m/z: 699.5 (M+1).

Step D: benzyl (2s)-2-(2,6-dichloro-4-((methoxy(2-methoxyphenyl)phosphoryl)ethynyl)benzylamino)-3-(3-(methylsulphonyl)phenyl)propionate (Compound 47.5)

Compound 47.4 (40 mg) was dissolved in 1 ml of methanol, and trimethylsilyldiazomethane (3 eq) was added and stirred at room temperature for 30 minutes. Appropriate amount of acetic acid was added for quenching, spun-dried, and 5 ml dilute hydrochloric acid solution was added. It was extracted 3 times with EA, and the organic phases were combined and spun-dried. LCMS ESI (+) m/z: 713.5 (M+1).

Step E: (2s)-2-(2,6-dichloro-4-((methoxy(2-hydroxyphenyl)phosphoryl)ethynyl)benzylamino)-3-(3-(methylsulfonyl)phenyl)propionic Acid (Compound 47)

Compound 47.5 (30 mg) was dissolved in DCM, and 1 mol/L of boron tribromide (10 eq) was added at −40° C., stirred at 0° C. for 30 minutes and then quenched with water at −40° C. It was extracted 3 times with EA, and the organic phases were combined, dried and spun-dried to give 15 mg of the target product. LCMS ESI (+) m/z: 609.5 (M+1).

$^1$H-NMR (400 MHz, DMSO), δ 10.57 (s, 1H), 9.21 (d, J=8.4 Hz, 1H), 7.88 (s, 1H), 7.78 (s, 2H), 7.67 (m, 2H), 7.57 (t, J=7.6 Hz, 1H), 5.96 (m, 2H), 4.80 (m, 1H), 3.77 (d, J=12.4 Hz, 3H), 3.30 (m, 1H), 3.15 (s, 3H), 3.03 (dd, J=14, J=9.4, 1H).

Example 48

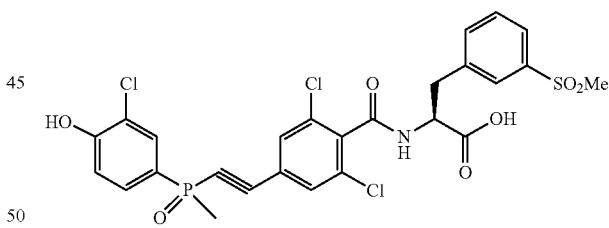

(2s)-2-(2,6-dichloro-4-((methyl(4-hydroxy-3-chlorophenyl)phosphoryl)ethynyl)benzylamino)-3-(3-(methylsulfonyl)phenyl)propionic Acid Example 48 was prepared by the same procedure as in Example 11 except that "diethyl m-methoxyphosphate" was replaced with "diethyl 4-methoxy-3-chlorophosphate". LCMS ESI (+) m/z: 628.1 (M+1).

$^1$H-NMR (400 MHz, DMSO) δ 11.15 (s, 1H), 9.21 (d, J=8 Hz, 1H), 7.86 (s, 1H), 7.79-7.82 (m, 4H), 7.68 (m, 2H), 7.57 (t, J=8 Hz, 1H), 7.15 (dd, J=7.6 Hz, 4.0 Hz, 1H), 4.79 (m, 1H), 3.30 (dd, J=14 Hz, J=4.4 Hz, 1H), 3.15 (s, 3H), 3.03 (dd, J=14 Hz, 10.4 Hz, 1H), 1.99 (d, J=13.2 Hz, 3H).

Example 49
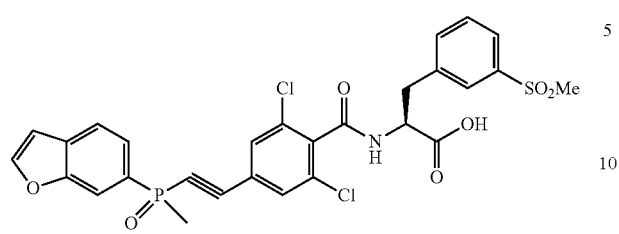
(2s)-2-(2,6-dichloro-4-((hydroxy(benzofuran-6-yl)phosphoryl)ethynyl)benzylamino)-3-(3-(methyl-sulfonyl)phenyl)propionic Acid
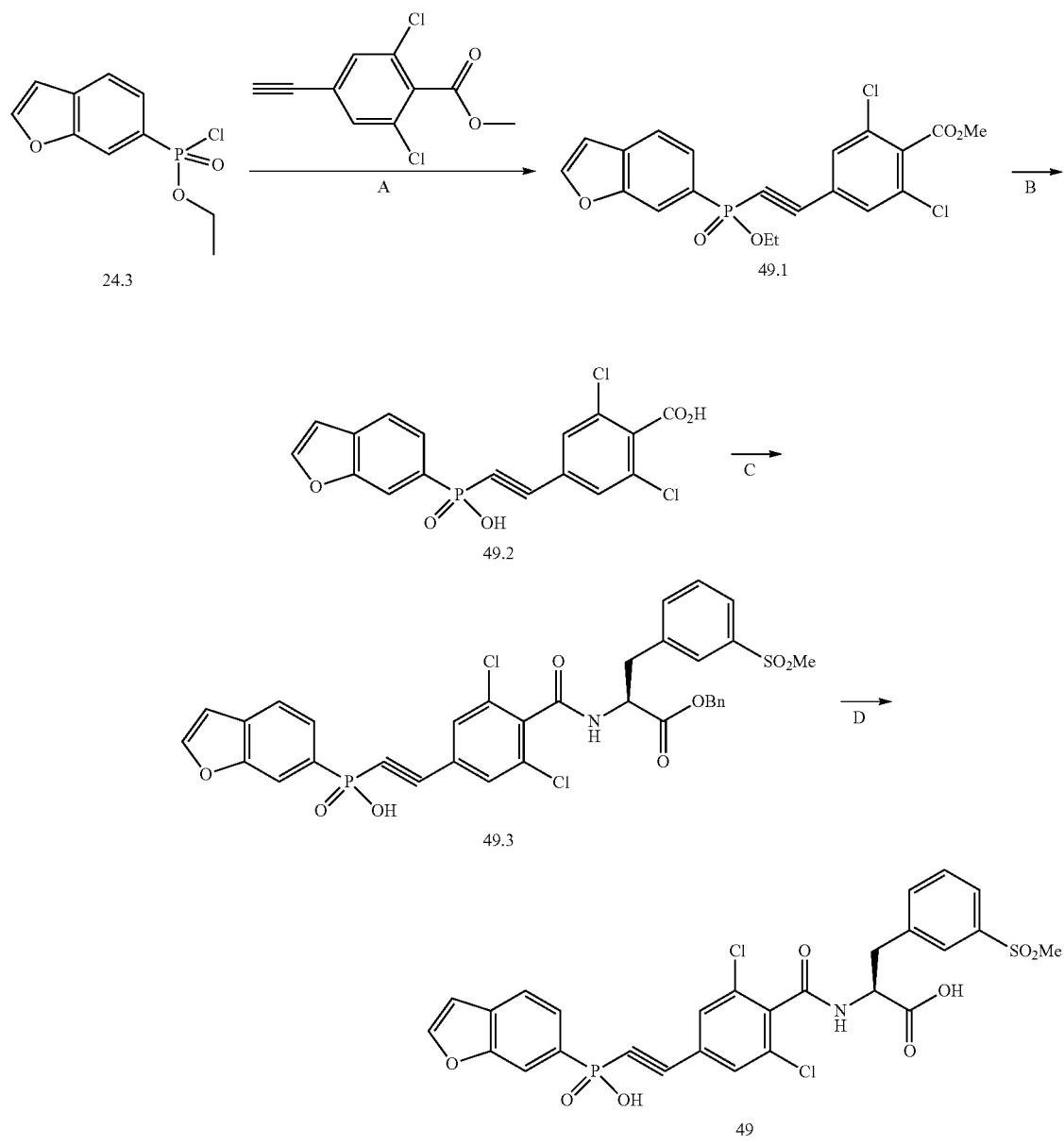

Step A: methyl 2,6-dichloro-4-(((benzofuran-6-yl)(ethoxy)phosphoryl)ethynyl)benzoate (Compound 49.1)

100 mg of methyl 2,6-dichloro-4-ethynylbenzoate was dissolved in 1.5 ml of tetrahydrofuran, protected with nitrogen, and 0.7 ml of 2 mol/L of isopropylmagnesium chloride was added at 0° C., and stirred for 20 minutes; Compound 24.3 was dissolved in 0.5 ml of tetrahydrofuran and reacted for 20 minutes. The reaction was quenched with 1 mol/L dilute hydrochloric acid solution, extracted three times with 30 mL of ethyl acetate, and the organic phases were combined, spun-dried, and purified to give the target product (100 mg, 60%). LCMS ESI (+) m/z: 437.1 (M+1).

Step B: 2,6-dichloro-4-((hydroxy(benzofuran-6-yl)phosphoryl)ethynyl)benzoic Acid (Compound 49.2)

Compound 49.1 (100 mg) and lithium iodide (100 mg) were dissolved in 2 ml of pyridine, protected under nitrogen, stirred at 120° C. for 3 hours, cooled and spun-dried, and 10 ml of 1 mol/L dilute hydrochloric acid solution was added. It was extracted three times with 30 ml ethyl acetate, and the organic phases were combined and spun-dried without further purification.

Step C: benzyl (2s)-2-(2,6-dichloro-4-((hydroxy(benzofuran-6-yl)phosphoryl)ethynyl)benzamido)-3-(3-(methylsulfonyl)phenyl)propionate (Compound 49.3)

Compound 49.2 was dissolved in DMF, and benzyl (2s)-2-amino-3-(3-(methylsulfonyl)phenyl)propionic acid hydrochloride (2 eq) was added, followed by DIPEA (10 eq) and HATU (2.5 eq). After stirring at normal temperature for 4 hours, 10 ml of dilute hydrochloric acid solution was added, and extracted with EA three times, and the organic phases were combined and spun-dried. Purification was made by reverse phase, and spun-dried at 45° C. under reduced pressure to give the target product, 85 mg. LCMS ESI (+) m/z: 710.1 (M+1).

Step D: (2s)-2-(2,6-dichloro-4-((hydroxy(benzofuran-6-yl)phosphoryl)ethynyl)benzylamino)-3-(3-(methylsulfonyl)phenyl)propionic Acid (Compound 49)

Compound 49.3 (30 mg) was dissolved in DCM, and 1 mol/L of boron tribromide (10 eq) was added at −40° C., stirred at 0° C. for 30 minutes and then quenched with water at −40° C. It was extracted 3 times with EA, and the organic phases were combined, dried and spun-dried to give 15 mg of the target product. LCMS ESI (+) m/z: 620.0 (M+1).

$^1$H-NMR (400 MHz, DMSO) δ 9.19 (d, J=8 Hz, 1H), 8.17 (s, 1H), 7.98 (d, J=248 Hz, 1H), 7.86 (s, 1H), 7.79-7.76 (m, 2H), 7.55-7.66 (m, 3H), 7.57 (t, J=8 Hz, 1H), 7.07 (s, 1H), 4.79 (m, 1H), 3.30 (dd, J=14 Hz, J=4.4 Hz, 1H), 3.15 (s, 3H), 3.02 (dd, J=14 Hz, 10.4 Hz, 1H).

Example 50

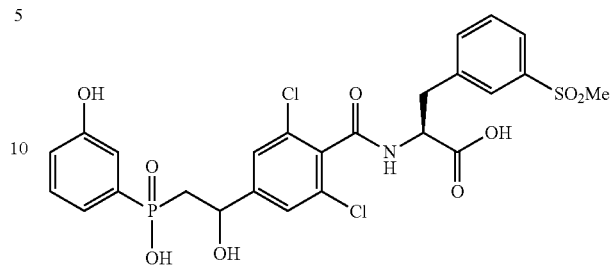

(2s)-2-(2,6-dichloro-4-(1-hydroxy 2-(hydroxy(3-hydroxyphenyl)phosphoryl)ethyl)benzamido)-3-(3-(methylsulfonyl)phenyl)propionic Acid The specific reaction equation is as follows:

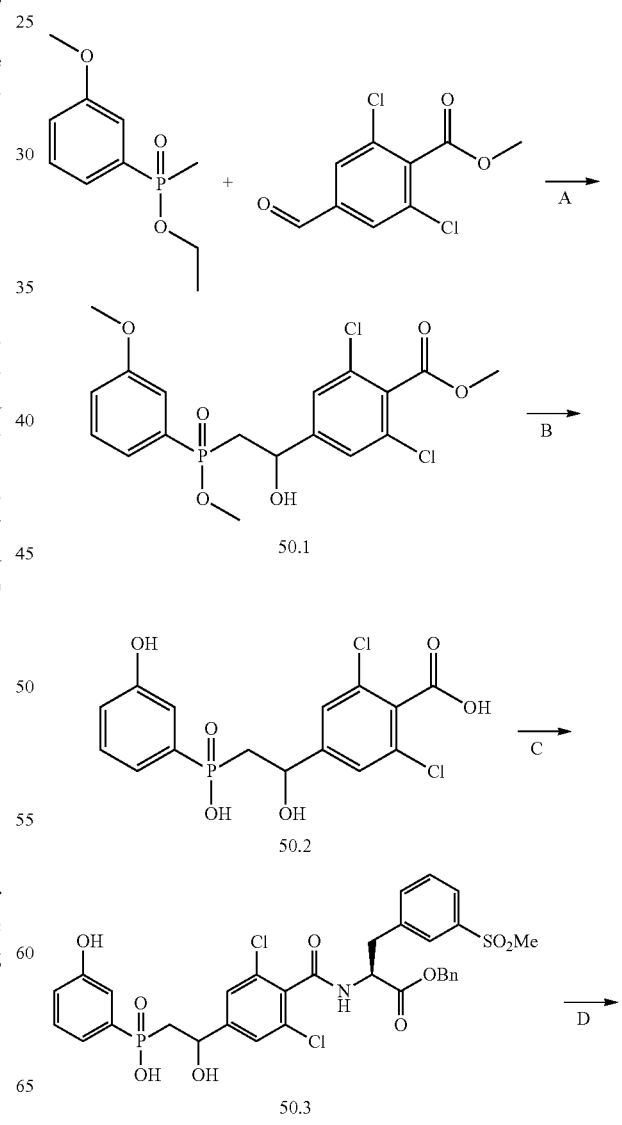

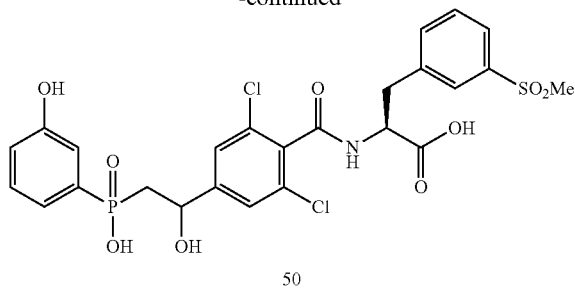

50

Step A: methyl 2,6-dichloro-4-(1-hydroxy 2-(methoxy(3-methoxyphenyl)phosphoryl)ethyl) benzoate (Compound 50.1)

300 mg of ethyl methyl(3-methoxyphenyl)phosphonate was weighed and dissolved in 10 ml of dry tetrahydrofuran under protection of nitrogen, and 1.1 mL (2M) of LDA was added thereto, stirred for 1 hour in an ice bath, 419 mg of methyl 2,6-dichloro-4-formylbenzoate was added, stirred at room temperature for 2 hours, quenched with the saturated NH$_4$Cl in an ice bath. It was extracted three times with 30 mL of ethyl acetate, and the organic phases were combined, spun-dried, and purified with columns to give the product (100 mg, 23%). LCMS ESI (+) m/z: 432.8.

Step B: 2,6-dichloro-4-(1-hydroxy 2-(hydroxy(3-hydroxyphenyl)phosphoryl)ethyl)benzoic Acid (Compound 50.2)

Compound 50.1 (100 mg) was dissolved in 8 ml of dichloromethane under protection with nitrogen. At −40° C., 1 mL of boron tribromide was added, stirred at −40° C. for 4 hours, quenched with 10 ml of water. It was extracted three times with 20 mL of ethyl acetate, and the organic phases were combined, spun-dried without purification to give 70 mg of the crude product. LCMS ESI (+) m/z: 390.8 (M+1).

Step C: benzyl (2s)-2-(2,6-dichloro-4-(1-hydroxy 2-(hydroxy(3-hydroxyphenyl)phosphoryl)ethyl)benzamido)-3-(3-(methanesulfonyl)phenyl)propanoic Acid (Compound 50.3)

Compound 50.2 was dissolved in DMF, and benzyl (2s)-2-amino-3-(3,5-(dimethylsulfonyl)phenyl)propanoic acid hydrochloride (2 eq) was added, followed by DIPEA (10 eq) and HATU (2.5 eq). After stirring at normal temperature for 4 hours, 10 ml of dilute hydrochloric acid solution was added, and extracted with EA three times, and the organic phases were combined and spun-dried. Purification was made by reverse phase, and spun-dried at 45° C. under reduced pressure to yield 40 mg of the target product. LCMS ESI (+) m/z: 705.7 (M+1).

Step D: (2s)-2-(2,6-dichloro-4-(1-hydroxy2-(hydroxy(3-hydroxyphenyl)phosphoryl)ethyl)benzamido)-3-(3-(methanesulfonyl)phenyl)propionic Acid (Compound 50)

Compound 1.3 was dissolved in 2 ml of methanol and 0.3 mL of water, 2 eq of lithium hydroxide monohydrate was added under ice bath, stirred at room temperature for 1 h, and pH was adjusted with 1N hydrochloric acid to pH=6, and 20 mL of ethyl acetate for extracting three times, washed with water, dried, rotary evaporated and prepared by reversed phase to yield 5 mg of the lyophilized product.

LCMS ESI (+) m/z: 583.6 (M+1);

$^1$H-NMR (400 MHz, CD$_3$OD-d$_4$) δ 7.95 (s, 1H), 7.86 (d, J=5.6 Hz, 1H), 7.73 (d, J=4.8 Hz, 1H), 7.62 (t, J=5.2 Hz, 1H), 7.31 (m, 2H), 7.26 (s, 2H), 7.21 (dd, J=5.2 Hz, J=5.2 Hz, 1H), 7.08 (d, J=8.4 Hz, 1H), 6.96 (t, J=5.2 Hz, 1H), 5.10 (m, 1H), 4.91 (m, 1H), 3.50 (dd, J=3.2 Hz, J=3.2 Hz, 1H), 3.22 (dd, J=2.8 Hz, J=3.2 Hz, 1H), 3.29 (s, 3H), 2.39 (m, 2H).

Example 51

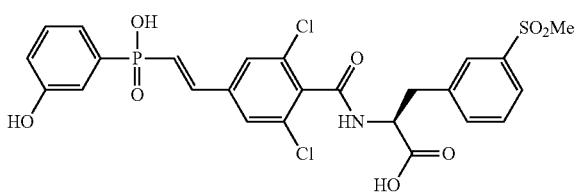 [SMILES: CS(=O)(=O)c1cccc(C[C@H](NC(=O)c2c(Cl)cc(/C=C/P(=O)(O)c3cccc(O)c3)cc2Cl)C(=O)O)c1]

(2s)-2-(2,6-dichloro-4-(2-(hydroxy(m-hydroxyphenyl)phosphoryl)vinyl)benzamido)-3-(3-(methylsulfonyl)phenyl)propionic Acid The specific reaction equation is as follows:

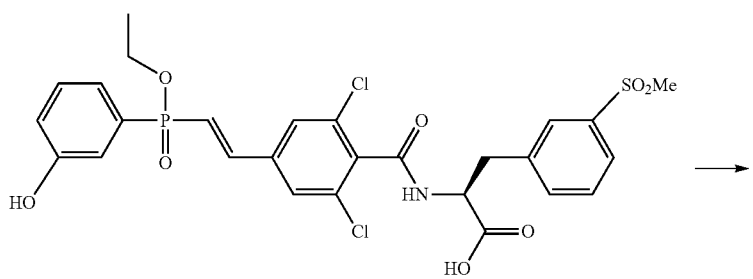

32

-continued

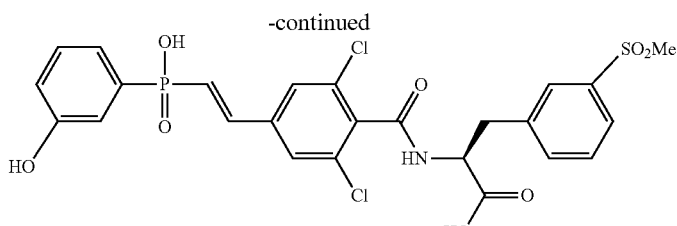
51

Compound 32 was dissolved in 5 ml of tetrahydrofuran, and 1 ml of aqueous LiOH solution was added thereto, stirred at room temperature for 5 hr, spun-dried and purified to obtain the product.

LCMS ESI (+) m/z: 599.4 (M+1).

$^1$H-NMR (400 MHz, DMSO) δ9.73 (s, 1H), 9.13 (d, J=8.8 Hz, 1H), 7.87 (s, 1H), 7.77 (d, J=8 Hz, 2H), 7.69 (d, J=7.6 Hz, 1H), 7.58 (t, J=7.6 Hz, 1H), 7.31 (m, 2H), 7.16 (m, 2H), 7.02 (m, 2H), 6.98 (m, 1H), 4.78 (m, 1H), 3.15 (s, 3H), 3.03 (m, 1H).

Example 52

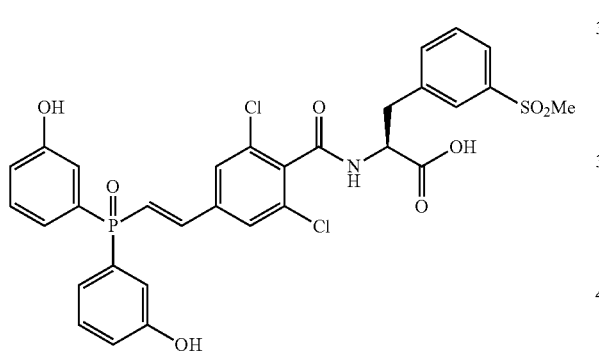

(S,E)-2-(4-(2-(bis(3-hydroxyphenyl)phosphonyl)vinyl)-2,6-dichlorobenzamido)-3-(3-(methylsulfonyl)phenyl)propionic Acid The specific reaction equation is as follows:

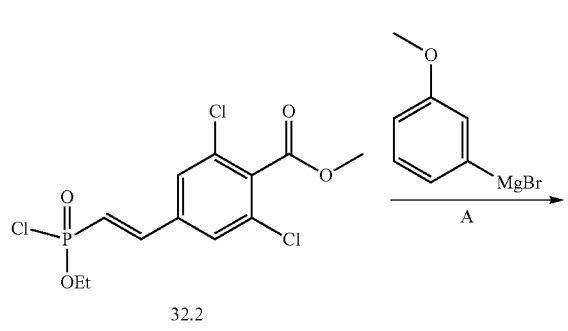
32.2

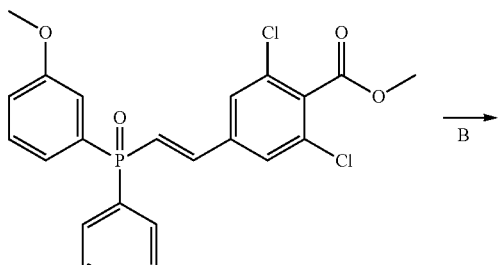
52.1

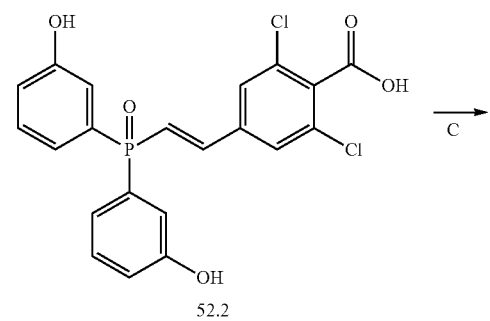
52.2

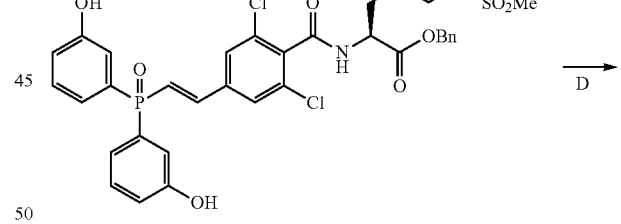
52.3

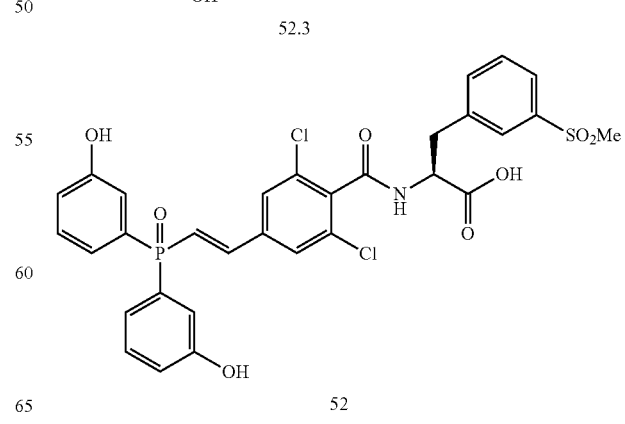
52

Step A: methyl (E)-4-(2-(bis(3-methoxyphenyl) phosphonyl)vinyl)-2,6-dichlorobenzoate (Compound 52.1)

1 g Compound 32.2 was dissolved in 20 ml of THF, cooled to 0° C., and 5 equivalents of m-methoxyphenyl-magnesium bromide solution was added, stirred at room temperature for 4 h, and THF was removed and the product was obtained after purification.

Step B: (E)-4-(2-(bis(3-hydroxyphenyl)phosphonyl) vinyl)-2,6-dichlorobenzoic Acid (Compound 52.2)

160 mg Compound 52.1, dissolved in 10 ml CH2Cl2, cooled to 0° C., and BBr3 was added, after 2 h of reaction, water was added, extracted with EA, then dried, and spun-dried to give the product.

Step C: benzyl (S,E)-2-(4-(2-(bis(3-hydroxyphenyl) phosphonyl)vinyl)-2,6-dichlorobenzamido)-3-(3-(methylsulfonyl)phenyl)propionate (Compound 52.3)

50 mg Compound 52.2, 40 mg of benzyl (2s)-2-amino-3-(3-(methylsulfonyl)phenyl)propanoic acid hydrochloride and 40 mg of DIPEA was dissolved in 5 ml DMF, 60 mg HATU was added, stirred overnight, and DMF was removed, and the product was obtained after purification.

Step D: (S,E)-2-(4-(2-(bis(3-hydroxyphenyl)phosphonyl)vinyl)-2,6-dichlorobenzamido)-3-(3-(methylsulfonyl)phenyl)propionic Acid (Compound 52)

15 mg Compound 52.3 was dissolved in 1 ml of THF, and 0.2 ml of aqueous LiOH solution was added thereto, stirred for 0.5 hour, and the solvent was removed to obtain a product.

LCMS ESI (+) m/z: 675.5 (M+1).

$^1$H-NMR (400 MHz, DMSO) δ 9.81 (s, 2H), 7.87 (s, 1H), 7.89 (s, 2H), 7.86 (s, 1H), 7.58 (t, 1H), 7.76 (d, J=4.6 Hz, 2H), 7.66 (m, 2H), 7.51 (t, 1H), 7.34 (m, 3H), 7.13 (m, 4H), 6.94 (d, J=4.4 Hz, 1H), 3.29 (dd, J=14 Hz, J=4.4 Hz, 1H), 3.15 (s, 3H), 3.01 (dd, J=14 Hz, 10.4 Hz, 1H).

Example 53

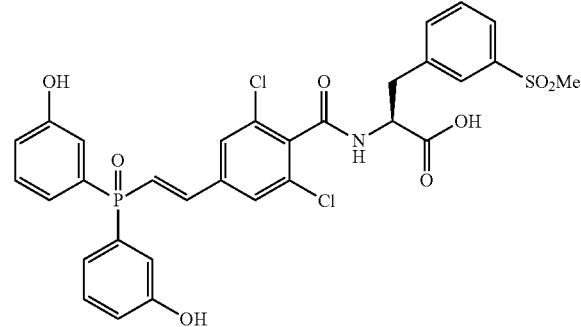 [SMILES: CS(=O)(=O)c1cccc(C[C@H](NC(=O)c2c(Cl)cc(/C=C/P(=O)(c3cccc(O)c3)c3cccc(O)c3)cc2Cl)C(=O)O)c1]

(S,E)-2-(4-(2-(bis(3-hydroxyphenyl)phosphonyl) ethyl)-2,6-dichlorobenzamido)-3-(3-(methylsulfonyl)phenyl)propionic Acid The specific reaction equation is as follows:

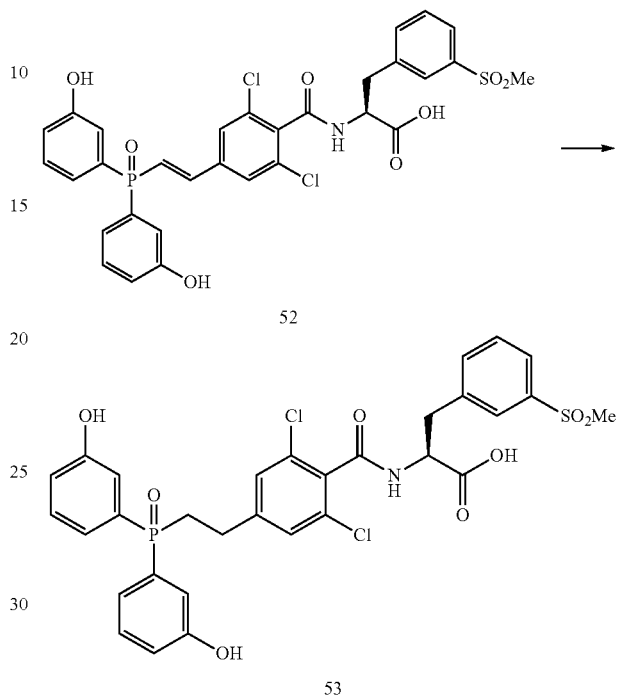

12 mg of Compound 52 was dissolved in 0.5 ml of MeOH, 1 mg of 10% palladium carbon was added, and H2 was added thereto, reacted for 3 hours, filtered, and the product was obtained after purification. LCMS ESI (+) m/z: 677.5 (M+1).

$^1$H-NMR (400 MHz, DMSO) δ 10.63 (s, 2H), 8.67 (s, 1H), 8.59 (d, J=8.4 Hz, 1H), 8.50 (d, J=8 Hz, 1H), 8.40 (t, 1H), 8.18 (s, 2H), 8.16 (m, 3H), 8.01 (m, 5H), 7.75 (dd, J=10 Hz, 2 Hz, 2H), 3.29 (dd, J=4 Hz, J=4.4 Hz, 1H), 3.15 (s, 3H), 3.01 (dd, J=14 Hz, 10.4 Hz, 1H), 2.81 (m, 2H), 2.11 (m, 2H).

Example 54

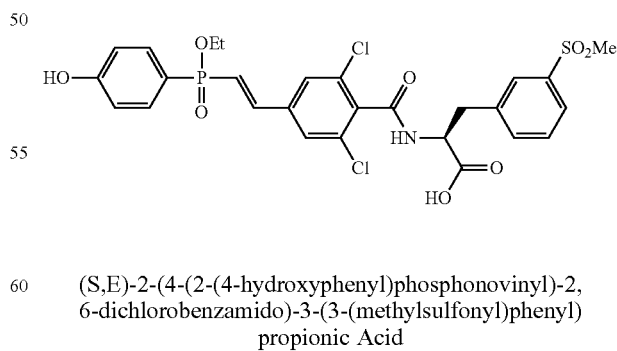

(S,E)-2-(4-(2-(4-hydroxyphenyl)phosphonovinyl)-2,6-dichlorobenzamido)-3-(3-(methylsulfonyl)phenyl) propionic Acid The exact same procedure as in Preparation Example 32 was used to prepare Example 54, wherein p-methoxymagnesium bromide was replaced by m-methoxymagnesium bromide. LCMS ESI (+) m/z: 629.5 (M+1).

¹H-NMR (400 MHz, DMSO) δ 9.15 (d, J=8 Hz, 1H), 7.87 (s, 1H), 7.73 (t, 3H), 7.60 (d, J=6 Hz, 1H), 7.58 (d, J=7.2 Hz, 1H), 7.58 (t, 1H), 7.18 (m, 3H), 6.91 (dd, J=10.4 Hz, 2 Hz, 2H), 4.80 (m, 1H), 3.92 (m, 2H), 3.3 (m, 2H), 3.12 (s, 1H), 1.26 (t, J=7.8 Hz, 3H).

Example 55

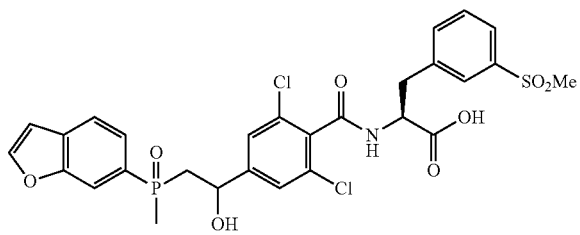 [SMILES: CP(=O)(CC(O)c1cc(Cl)c(C(=O)N[C@@H](Cc2cccc(S(C)(=O)=O)c2)C(=O)O)c(Cl)c1)c1ccc2ccoc2c1]

(2s)-2-(2,6-dichloro-4-(1-hydroxy2-(methyl(benzofuran-3-yl)phosphoryl)ethyl)benzamido)-3-(3-(methylsulphonyl)phenyl)propionic Acid The specific reaction equation is as follows:

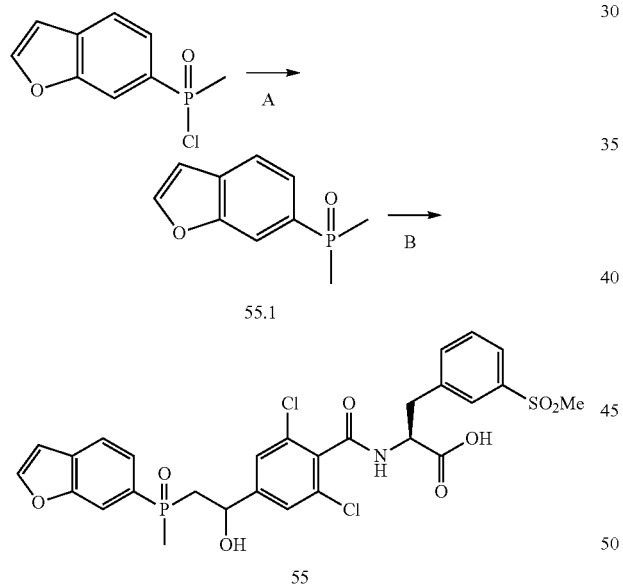

Step A: dimethyl (benzofuran-3-yl)phosphine oxide (Compound 55.1)

100 mg of methyl (benzofuran-3-yl)phosphonyl chloride was dissolved in 2 ml of tetrahydrofuran, protected with nitrogen, and 0.7 ml of 3 mol/L methyl magnesium bromide was added at 0° C. and stirred for 20 minutes. The reaction was quenched with 1 mol/L dilute hydrochloric acid solution. It was extracted three times with 30 mL of ethyl acetate, and the organic phases were combined, spun-dried, and purified to give the target product.

LCMS ESI (+) m/z: 195.1 (M+1).

Step B: (2s)-2-(2,6-dichloro-4-(1-hydroxy2-(methyl(benzofuran-3-yl)phosphoryl)ethyl)benzamido)-3-(3-(methylsulfonyl)phenyl)propionic Acid (Compound 55)

Using the exact same procedure as in Example 50, replacing "methyl (3-methoxyphenyl)phosphonate" with "dimethyl(benzofuran-3-yl)phosphine oxide" to prepare Compound 55.

LCMS ESI (+) m/z: 638.1 (M+1).

¹H-NMR (400 MHz, DMSO) δ 9.09 (d, J=8 Hz, 1H), 8.16 (s, 1H), 8.01 (t, J=8 Hz, 1H) 7.87 (s, 1H), 7.77-7.82 (m, 2H), 7.68 (m, 2H), 7.57 (t, J=8 Hz, 1H), 7.38 (s, 2H), 7.05 (dd, J=7.6 Hz, 4.0 Hz, 1H), 4.90 (m, 1H), 4.77 (m, 1H), 3.30 (dd, J=14 Hz, J=4.4 Hz, 1H), 3.15 (s, 3H), 3.03 (dd, J=14 Hz, 10.4 Hz, 1H), 2.40 (m, 2H), 1.80 (d, J=13.2 Hz, 3H).

Example 56

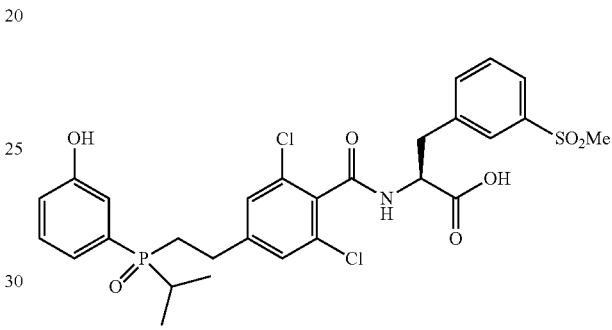

(2s)-2-(2,6-dichloro-4-(isopropyl(3-hydroxyphenyl)phosphoryl)ethyl)benzamido)-3-(3-(methylsulfonyl)phenyl)propionic Acid The exact same procedure as in Preparation Example 21 was used to prepare Example 56, wherein the ethyl Grignard reagent was replaced by the isopropyl Grignard reagent.

LCMS ESI (+) m/z: 626.1 (M+1).

¹H-NMR (400 MHz, DMSO) δ 9.76 (s, 1H), 9.03 (d, J=8 Hz, 1H), 7.86 (s, 1H), 7.77 (d, J=8 Hz, 1H), 7.67 (d, J=8 Hz, 1H), 7.57 (t, J=7.6 Hz, 1H), 7.31-7.35 (m, 3H), 7.12-7.17 (m, 2H), 6.94 (d, J=7.6 Hz, 1H), 4.75 (m, 1H), 3.29 (dd, J=14 Hz, J=4.4 Hz, 1H), 3.15 (s, 3H), 3.01 (dd, J=14 Hz, 10.4 Hz, 1H), 2.74 (m, 1H), 2.50 (m, 1H), 2.29 (m, 2H), 2.07 (m, 1H), 1.10 (dd, J=16 Hz, 7.0 Hz, 3H), 0.88 (dd, J=16 Hz, 7.0 Hz, 3H).

Example 57

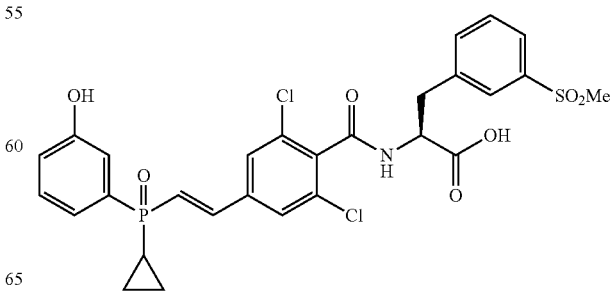

75

(2s)-2-(2,6-dichloro-4-(cyclopropyl(3-hydroxyphenyl)phosphoryl)vinyl)benzamido)-3-(3-(methylsulfonyl)phenyl)propionic Acid The specific reaction equation is as follows:

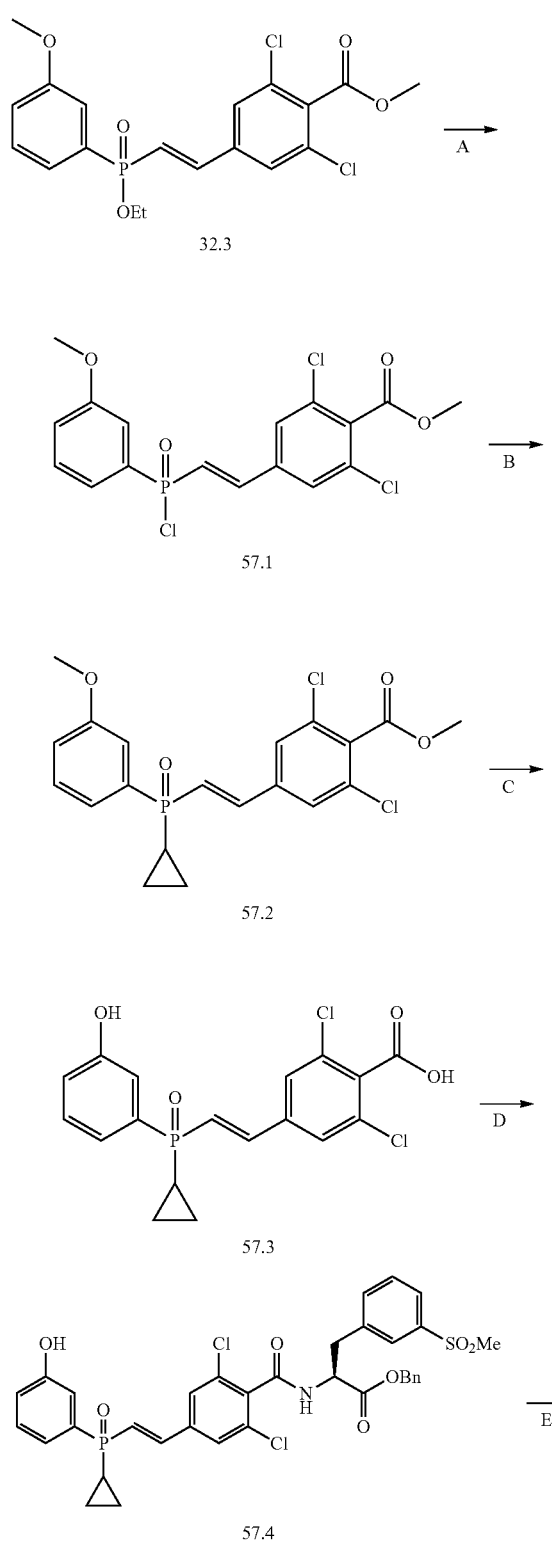

76

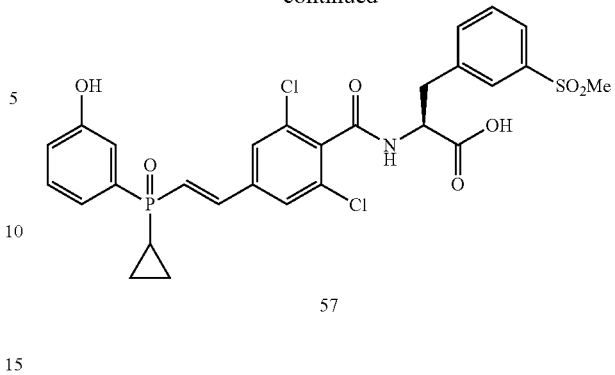

Step A: methyl (E)-4-(2-(3-methoxyphenyl)chlorophosphonylvinyl)-2,6-dichlorobenzoate (Compound 57.1)

1 g Compound 32.3 was dissolved in 20 ml of SOCl2, heated at 80° C. for 3 hours, concentrated to give the product.

Step B: methyl (E)-4-(2-(3-methoxyphenyl)cyclopropylphosphorylvinyl)-2,6-dichlorobenzoate (Compound 57.2)

10 ml of 1 M cyclopropylmagnesium chloride solution in THF, 0.5 g of cesium chloride was added, and 1 g of Compound 57.1 was added thereto, and reacted at room temperature for 1 hour, and then quenched with ammonium chloride solution to obtain a product after extraction and purification.

Step C: (E)-4-(2-((3-hydroxyphenyl)cyclopropylphosphonyl)vinyl)-2,6-dichlorobenzoic Acid (Compound 57.3)

160 mg Compound 57.2 was dissolved in 10 ml CH2Cl2, cooled to 0° C., BBr3 was added, after 2 h of reaction, water was added, extracted with EA, dried, and spun-dried to give the product.

Step D: benzyl (S,E)-2-(4-(2-(3-hydroxyphenyl)cyclopropylphosphonyl)vinyl)-2,6-dichlorobenzamido)-3-(3-(methylsulphonyl)phenyl)propanoate (Compound 57.4)

50 mg Compound 57.3, benzyl (2s)-2-amino-3-(3-(methylsulfonyl)phenyl)propanoic acid hydrochloride and 40 mg of DIPEA were dissolved in 5 ml DMF, 60 mg HATU was added, stirred overnight to remove DMF, and the product was obtained after purification.

Step E: (S,E)-2-(4-(2-(3-hydroxyphenyl)cyclopropylphosphonyl)vinyl)-2,6-dichlorobenzamido)-3-(3-(methanesulfonyl)phenyl)propionic Acid (Compound 57)

15 mg Compound 57.4 was dissolved in 1 ml of THF, and 0.2 ml of aqueous LiOH solution was added thereto, stirred for 0.5 hour, and the solvent was removed, the product was obtained after purification.

LCMS ESI (+) m/z: 6221. (M+1).

$^1$H-NMR (400 MHz, DMSO) δ 9.80 (s, 1H), 9.13 (d, J=8.8 Hz, 1H), 7.87 (s, 1H), 7.82 (s, 2H), 7.78 (d, J=8 Hz, 2H), 7.69 (d, J=7.6 Hz, 1H), 7.58 (t, J=7.6 Hz, 1H), 7.17-7.37 (m, 5H), 6.96 (m, 1H), 4.79 (m, 1H), 3.30 (dd, J=4 Hz, J=4.4 Hz, 1H), 3.15 (s, 3H), 3.04 (dd, J=4 Hz, 10.4 Hz, 1H), 1.25 (m, 1H), 0.66-0.89 (m, 4H).

Example 58

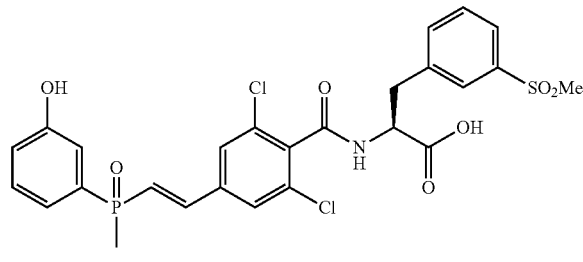 [SMILES: CP(=O)(/C=C/c1cc(Cl)c(C(=O)N[C@@H](Cc2cccc(S(C)(=O)=O)c2)C(=O)O)c(Cl)c1)c1cccc(O)c1]

(2s)-2-(2,6-dichloro-4-(methyl(3-hydroxyphenyl) phosphoryl)vinyl)benzamido)-3-(3-(methylsulfonyl) phenyl)propionic Acid The exact same procedure as in Preparation Example 57 was used to prepare Example 58, wherein the cyclopropyl Grignard reagent was replaced by the methyl Grignard reagent. LCMS ESI (+) m/z: 596.1 (M+1).

$^1$H-NMR (400 MHz, DMSO) δ 9.80 (s, 1H), 9.14 (d, J=8.8 Hz, 1H), 7.87 (s, 1H), 7.78 (m, 3H), 7.69 (d, J=7.6 Hz, 1H), 7.58 (t, J=7.6 Hz, 1H), 7.38 (m, 1H), 7.25 (d, J=20 Hz, 2H), 7.15-7.18 (m, 2H), 6.96 (m, 1H), 4.79 (m, 1H), 3.30 (dd, J=14 Hz, J=4.4 Hz, 1H), 3.15 (s, 3H), 3.04 (dd, J=14 Hz, 10.4 Hz, 1H), 1.73 (d, J=13.2 Hz 3H).

Cell Adhesion Inhibition Experiments:

T-cell adhesion assay was performed using human T lymphocyte strain Jurkat (ATCC TIB-152): goat Anti-Human IgG (Fc specific) (Sigma 18885) was diluted to 10 μg/ml in PBS, incubated 100 μL per well/96 well plate at 4° C. for 12 hours. Liquid in the well plate was poured off, blocked with 200 μL of 1% BSA at 37° C. for 90 minutes, and washed three times with PBS. 50 μL of 1 μg/mL ICAM-1 (containing 0.1% BSA, 0.01% Tween 20) was added to each well and incubated at 37° C. for 3 hours. The plate was washed 3 times with assay buffer (20 mM HEPES pH 7.6, 140 mM NaCl, 1 mM $MgCl_2$, 1 mM $MnCl_2$, 0.2% glucose).

The Jurkat cytometer was centrifuged at 100-G, and cells were resuspended in an assay buffer (20 mM HEPES pH 7.6, 140 mM NaCl, 1 mM $MgCl_2$, 1 mM $MnCl_2$, 0.2% glucose) at 37° C.

2 μl of 1 mM of BCECF-AM per mL of the cell suspension was added. Incubated at 37° C. for 30 minutes, stirred up every 10 minutes during the incubation. After the incubation, the cells were washed with assay buffer at 37° C. The cells were suspended to a concentration of $6\times10^6$/mL.

The inhibitor was diluted to a final concentration of 2× in assay buffer, and 50 μL of the compound solution and 60 μL of Jurkat cells were mixed at room temperature, and incubated at 37° C. for 30 minutes. 100 μL/well of cells and inhibitors were added to the plate and incubated for 1 hour at room temperature. The total fluorescence was measured by a fluorometer: ex: 485; em: 530; cutoff: 530 to measure the total fluorescence. The plate was washed once with the assay buffer and the fluorescence was measured with a fluorometer: ex: 485; em: 530; cutoff. The results are plotted as inhibition-concentration plots and $EC_{50}$ is calculated using standard methods.

Table 1 shows the $EC_{50}$ values of selected compounds measured by this method.

TABLE 1

| Example | $EC_{50}$ of cell adhesion and inhibition $EC_{50}$ (nM) |
|---|---|
| 1 | 30 |
| 2 | 9.4 |
| 3 | 8.5 |
| 4 | 11 |
| 5 | 22 |
| 6 | 17 |
| 7 | 7.2 |
| 8 | 6.2 |
| 9 | 11.8 |
| 10 | 78 |
| 11 | 13.5 |
| 12 | 29 |
| 13 | 29 |
| 14 | 8.5 |
| 15 | 1.8 |
| 16 | 7.2 |
| 17 | 15 |
| 18 | NA* |
| 19 | 230 |
| 20 | NA* |
| 21 | 7.3 |
| 22 | 22 |
| 23 | 61 |
| 24 | 10.2 |
| 25 | 63 |
| 26 | 23 |
| 27 | NA* |
| 28 | NA* |
| 29 | NA* |
| 30 | 7.2 |
| 31 | 7.1 |
| 32 | 3.7 |
| 33 | 10.8 |
| 34 | 12.5 |
| 35 | 3.8 |
| 36 | 30 |
| 37 | >1000 |
| 38 | 24 |
| 39 | NA* |
| 40 | NA* |
| 41 | NA |
| 42 | 150 |
| 43 | 69 |
| 44 | NA* |
| 45 | >1000 |
| 46 | >1000 |
| 47 | 340 |
| 48 | 6.8 |
| 49 | 10.8 |
| 50 | 16 |
| 51 | 4.2 |
| 52 | 74 |
| 53 | 22 |
| 54 | 9.6 |
| 55 | 19 |
| 56 | 63 |
| 57 | 5.3 |
| 58 | 1.9 |

*NA: No Data

Example: Formulation Preparation 5.0 g compound obtained by Example 11 was added to 90 mL of sterile physiological saline, and 0.7 g of NaOH was added thereto, then stirred to obtain a transparent solution; and a saturated aqueous solution of $NaH_2PO_4$ was added to the solution obtained above until the pH of the solution was 6.75-7.25 between. Sterile physiological saline was added to the obtained aqueous solution until the total volume reached 100.0 mL. The above solution was purged with nitrogen, and bubbled for 1 hour. The resulting solution was sealed and stored at 5° C. protected from light. The mixture was dispensed into disposable eye drops bags, each containing 60 mL of formulation solution. The method and specific ratio of the formulation can also be adjusted as needed, depending on the nature of the particular compound and the requirements of the application.

What is claimed is:

1. A phosphorus-containing compound, wherein the compound represented by the following structure:

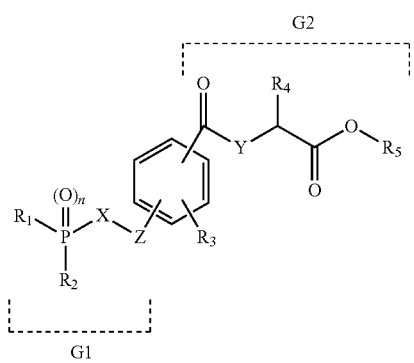

$R_1$ is selected from alkyl, aryl, benzyl and aryl derivatives;
$R_2$ is selected from hydroxy, alkyl, hydrogen, and alkoxy;
n is selected from 0 or 1;
X is selected from carbon, oxygen, and nitrogen; when X is carbon, it is —CH$_2$—, —C(R1R2)-, —CH═ or —C≡, wherein R1, R2 are the same or different alkyl, aromatic group, hydroxy, alkoxy or halogen; when X is nitrogen, it is —NH— or —N(R$_N$)—, wherein R$_N$ is alkyl or aromatic group;
Z is selected from —C(R1R2)-, —CH$_2$—, —CH═, and —C≡, wherein R1, R2 are the same or different alkyl, aromatic group, hydroxy, alkoxy or halogen; when X is —CH═, then Z is also —CH═; when X is —C≡, then Z is also —C≡;
$R_3$ is one or more substituents on the benzene ring independently selected from hydrogen, alkyl, alkoxy, halogen, amino, cyano, hydroxy, nitro and aryl;
Y is selected from oxygen and nitrogen;
$R_4$ is selected from alkyl, alkyl derivatives, aryl, benzyl and benzyl derivatives;
$R_5$ is selected from hydrogen, alkyl, aryl, and benzyl;
the substituent groups represented by G1 and G2 are disposed on the benzene ring in meta, para or ortho position.

2. The phosphorus-containing compound according to claim 1, wherein the $R_1$ is selected from the group consisting of phenyl and derivatives thereof, naphthyl and derivatives thereof, N— or O-heterophenyl and derivatives thereof, N- or O-heteronaphthyl and derivatives thereof;
wherein the derivatives refer to one or more independently substituted hydrogen, alkyl, alkoxy, halogen, amino, cyano, hydroxy; nitro, aryl, alkylsulfonyl and phenylsulfonyl on the benzene ring.

3. The phosphorus-containing compound according to claim 1, wherein $R_4$ is selected from the groups represented by the following structure:

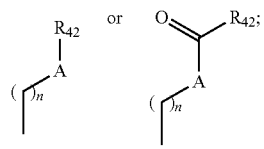

n is selected from an integer of 0 to 5;
the A is selected from —CH$_2$— and —NH—, wherein when n is 0, the A is —CH$_2$—;
the $R_{42}$ is selected from aryl, alkyl, alkylamino, alkylsulfonamide, cycloalkyl, substituted cycloalkyl, heterocycloalkyl, substituted heterocycloalkyl;
wherein the aryl group is selected from 6-12 membered aromatic groups and derivatives thereof, and heteroaryl with one or more carbon atoms on a 5-12 membered aromatic ring substituted by oxygen, nitrogen or sulfur;
wherein the derivatives refer to the aromatic ring having one or more substituted hydrogen, alkyl, alkoxy, halogen, amino, cyano, hydroxy, nitro, sulfonyl, alkylsulfonyl or phenylsulfonyl thereon;
the heteroaryl group further have a structure of —N—$R_{422}$ on it;
the $R_{422}$ is sulfonyl, alkylsulfonyl, alkyl, or hydroxy;
the cycloalkyl is a 3-12 membered cycloalkyl group;
the substituted cycloalkyl refers to the ring group having one or more independently substituted sulfonyl, alkylsulfonyl, alkyl, alkoxy, hydroxy, amino or nitro;
the heterocycloalkyl is a 3-12 membered heterocycloalkyl group having one or more carbon atoms substituted by oxygen, nitrogen and sulfur;
the carbon atoms on the heterocycloalkyl can also be substituted by C═O and/or SO and/or SO$_2$;
the substituted heterocycloalkyl is aza-, oxa- or thiacycloalkyl having a four, five, six or seven membered ring, by which the ring is independently substituted by one or more sulfonyl, alkylsulfonyl, alkyl, alkoxy, hydroxy, amino, nitro, carbonyl;
the substituted heterocycloalkyl group further have a structure of —N—$R_{422}$ on it;
the $R_{422}$ is sulfonyl, alkylsulfonyl, alkyl, or hydroxy;
the $R_{42}$ also be selected from the groups represented by the following structures:

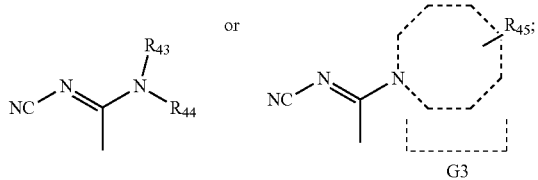

the $R_{43}$ and $R_{44}$ are the same or different alkyl, hydroxy, hydroxy substituted alkyl having not more than 5 carbon atoms;
G3 is a 3-12 membered ring;
the carbon atom on the ring of G3 also be partially replaced by oxygen, sulfur, nitrogen, C═O or SO$_2$;
the $R_{45}$ is one or more substituents on G3 ring selected from alkyl, hydroxy, alkoxy and amino.

4. The phosphorus-containing compound according to claim 1, wherein the compound is represented by the following structure:

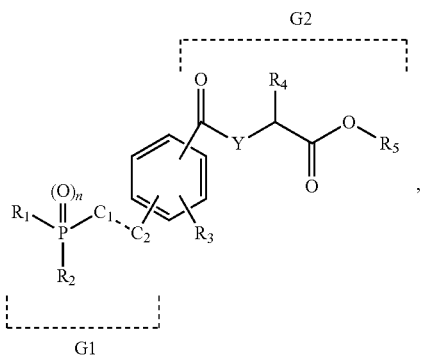

wherein C1 ... C2 is CH$_2$—CH$_2$, CH=CH or C≡C.

5. The phosphorus-containing compound according to claim 4, wherein the compound is represented by the following structure:

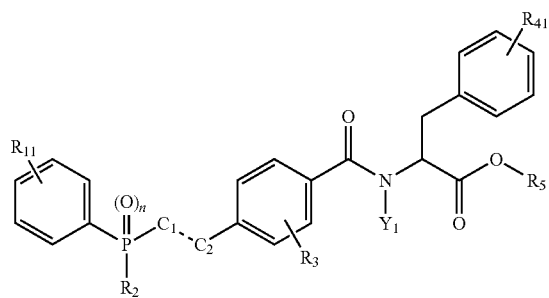

$R_{11}$ is one or more substituents on the benzene ring independently selected from hydrogen, alkyl, alkoxy, halogen, amino, cyano, hydroxy, and nitro;

$R_2$ is selected from hydroxy, alkyl, and alkoxy;

$R_3$ is one or more substituents on the benzene ring independently selected from hydrogen, alkyl, alkoxy, halogen, amino, cyano, hydroxy, nitro, and aryl;

$Y_1$ is selected from hydrogen and alkyl;

$R_{41}$ is one or more substituents on the benzene ring independently selected from hydrogen, alkyl, alkoxy, alkylsulfonyl, arylsulfonyl, halogen, amino, cyano, hydroxy, and nitro;

$R_5$ is selected from hydrogen, alkyl, aryl, and benzyl.

6. A phosphorus-containing compound, wherein the compound is represented by the following structure:

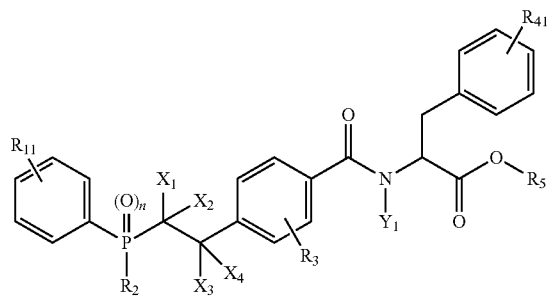

wherein, $X_1$, $X_2$, $X_3$ and $X_4$ are selected from hydrogen, alkyl, halogen, hydroxy and alkoxy, and the other substituents are as defined in claim 5.

7. A method for preparing the phosphorus-containing compound according to claim 1, wherein Compound A and Compound C are sequentially reacted with an active site on Compound B;

wherein Compound A is a compound represented by the following structure:

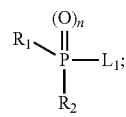

Compound C is a compound represented by the following structure:

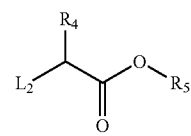

Compound B is a compound represented by the following structure:

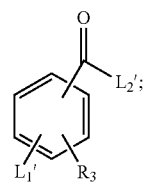

wherein, $L_1$ and $L_1'$ as well as $L_2$ and $L_2'$ are respectively a pair of active groups which can react with each other, during the reaction, a target product was obtained through the reaction between $L_1$ and $L_1'$, and the reaction between $L_2$ and $L_2'$, wherein the $L_1$ is selected from halogen, amino, cyano, thio, hydroxy, and alkoxyl; the $L_1'$ is selected from halogen, alkynyl, carboxyl, amino, cyano, ester group, alkoxy, sulfonylamino, and alkoxysulfonyl;

the $L_2$ is selected from halogen, carboxyl, amino, cyano, ester group, alkoxy, sulfonamido, and alkoxysulfonyl;

the $L_2'$ is selected from halogen, amino, thio, hydroxy and alkoxy.

8. The method for preparing the phosphorus-containing compound according to claim 7, wherein a substitution reaction, an addition reaction, an elimination reaction or a replacement reaction can be carried out between the $L_1$ and $L_1'$ as well as between $L_2$ and $L_2'$.

9. The method for preparing the phosphorus-containing compound according to claim 7, wherein a molar ratio of the Compound A to Compound C is 1:0.1-10; a molar ratio of the Compound C to Compound B is 1:0.1-10.

10. The method for preparing the phosphorus-containing compound according to claim 7, wherein the specific process steps are as follows:

Step 1, adding a halogenating reagent to a phosphodiester derivative, reacting at a temperature of 50-100° C. for 1-5 hours, and directly spinning dry to obtain a substrate 1;

Step 2: sequentially adding a Grignard reagent and the substrate 1 to a derivative of methyl ethynylbenzoate at a temperature below 0° C., reacting for 0.1-2 hours, quenching the reaction with an acid solution, extracting an organic phase and spinning dry to obtain an intermediate product 1;

Step 3, reacting the intermediate product 1 with a de-esterification reagent at a temperature of 100-150° C. for 2-5 hours, adding the acid solution, extracting the organic phase to spin dry, and obtaining an intermediate product 2;

Step 4, in the intermediate product 2, sequentially adding compound C in which $L_2$ is amino, and a basic catalyst, reacting at a temperature of 20-50° C. for 1-10 hours, quenching the reaction with the acid solution, and extracting the organic phase to spin dry, and obtaining a phosphorus-containing compound containing alkynyl group.

11. The method for preparing the phosphorus-containing compound according to claim 10, wherein a corresponding phosphorus-containing product can be obtained after the phosphorus-containing compound containing alkynyl group is subjected to one or more reactions selected from reduction reaction, esterification reaction, amidation reaction, substitution reaction and addition reaction.

12. An eyedrop containing the phosphorus-containing compound according to claim 1.

13. A method for preparing the eyedrop according to claim 12, comprising:
adding the phosphorus-containing compound to a sterile physiological saline solution, and then adding sodium hydroxide to obtain a transparent solution;
adding a saturated aqueous solution of $NaH_2PO_4$ to the transparent solution obtained above until pH of the solution is between 6.75 and 7.25;
adding sterile physiological saline to adjust the final volume; and
bubbling the nitrogen gas to the above solution for 0.1-5 hours, and sealing the resulting solution, and storing at 5° C. protected from the light for use;
wherein the sodium hydroxide and the saturated aqueous solution of $NaH_2PO_4$ can be replaced by other buffer solutions.

* * * * *

UNITED STATES PATENT AND TRADEMARK OFFICE
CERTIFICATE OF CORRECTION

PATENT NO. : 11,325,929 B2
APPLICATION NO. : 16/606774
DATED : May 10, 2022
INVENTOR(S) : Wang Shen et al.

Page 1 of 1

It is certified that error appears in the above-identified patent and that said Letters Patent is hereby corrected as shown below:

In the Specification

Please replace " 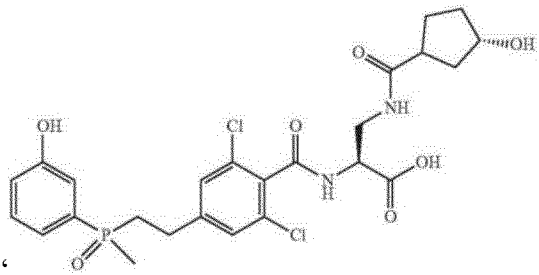 " with

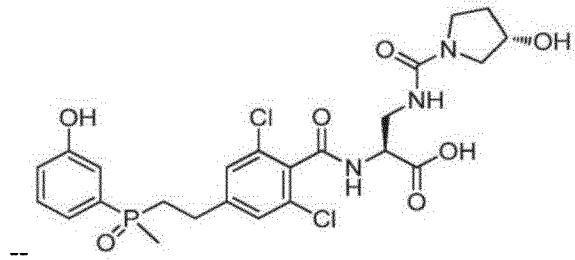

-- -- (Column 58, Lines 5-15).

Signed and Sealed this
Twenty-eighth Day of June, 2022

Katherine Kelly Vidal
Katherine Kelly Vidal
*Director of the United States Patent and Trademark Office*